(12) United States Patent
Stevenson et al.

(10) Patent No.: US 10,912,945 B2
(45) Date of Patent: *Feb. 9, 2021

(54) HERMETIC TERMINAL FOR AN ACTIVE IMPLANTABLE MEDICAL DEVICE HAVING A FEEDTHROUGH CAPACITOR PARTIALLY OVERHANGING A FERRULE FOR HIGH EFFECTIVE CAPACITANCE AREA

(71) Applicant: Greatbatch Ltd., Clarence, NY (US)

(72) Inventors: Robert A. Stevenson, Canyon Country, CA (US); Christine A. Frysz, Orchard Park, NY (US); Jason Woods, Carson City, NV (US)

(73) Assignee: Greatbatch Ltd., Clarence, NY (US)

( * ) Notice: Subject to any disclaimer, the term of this patent is extended or adjusted under 35 U.S.C. 154(b) by 32 days.

This patent is subject to a terminal disclaimer.

(21) Appl. No.: 16/360,372

(22) Filed: Mar. 21, 2019

(65) Prior Publication Data

US 2019/0290920 A1 Sep. 26, 2019

Related U.S. Application Data

(63) Continuation-in-part of application No. 16/121,716, filed on Sep. 5, 2018, now Pat. No. 10,596,369, which
(Continued)

(51) Int. Cl.
*A61N 1/375* (2006.01)
*H01R 13/26* (2006.01)
(Continued)

(52) U.S. Cl.
CPC .......... *A61N 1/3754* (2013.01); *A61N 1/378* (2013.01); *H01R 4/58* (2013.01); *H01R 13/26* (2013.01);
(Continued)

(58) Field of Classification Search
CPC .. A61N 1/3754; A61N 1/378; A61N 1/37512; H01R 4/58; H01R 13/26;
(Continued)

(56) References Cited

U.S. PATENT DOCUMENTS 3,681,612 A 8/1972 Kinzler et al.
3,745,430 A 7/1973 Kerr et al.
(Continued)

FOREIGN PATENT DOCUMENTS

EP 0243573 11/1987
EP 0145430 5/1991
(Continued)

OTHER PUBLICATIONS

Olenick, "Ultrathin Flexible Ceramics for Electronics Applications", www.ceramicindustry.com—Product Profile, Oct. 2016, pp. 30 and 31.
(Continued)

*Primary Examiner* — Lindsey G Wehrheim
(74) *Attorney, Agent, or Firm* — Michael F. Scalise

(57) ABSTRACT

A filter feedthrough for an AIMD includes an electrically conductive ferrule. An insulator hermetically seals a ferrule opening with either a first gold braze, a ceramic seal, a glass seal or a glass-ceramic seal. At least one conductive pathway is hermetically sealed to and disposed through the insulator body in non-conductive relationship with the ferrule. A feedthrough capacitor includes at least one active and ground electrode plate disposed within a capacitor dielectric and electrically connected to a capacitor active metallization and a capacitor ground metallization, respectively. At least a first edge of the feedthrough capacitor extends beyond a first outermost edge of the ferrule. At least a second edge of the feedthrough capacitor does not extend beyond a second outermost edge of the ferrule, or said differently, the second
(Continued)

edge is either aligned with or setback from the second outermost edge of the ferrule.

29 Claims, 46 Drawing Sheets

Related U.S. Application Data is a continuation of application No. 15/943,998, filed on Apr. 3, 2018, now Pat. No. 10,350,421.

(60) Provisional application No. 62/646,552, filed on Mar. 22, 2018.

(51) Int. Cl.
  *A61N 1/378* (2006.01)
  *H01R 13/52* (2006.01)
  *H01R 4/58* (2006.01)
  *H03H 1/00* (2006.01)

(52) U.S. Cl.
  CPC ..... *H01R 13/5221* (2013.01); *H01R 13/5224* (2013.01); *A61N 1/37512* (2017.08); *H01R 2201/12* (2013.01); *H03H 2001/0014* (2013.01); *H03H 2001/0021* (2013.01); *H03H 2001/0042* (2013.01)

(58) Field of Classification Search
  CPC ............ H01R 13/5221; H01R 13/5224; H01R 2201/12; H03H 2001/0014; H03H 2001/0021; H03H 2001/0042
  See application file for complete search history.

(56) References Cited

U.S. PATENT DOCUMENTS

| | | |
|---|---|---|
| 3,871,382 A | 3/1975 | Mann |
| 3,961,294 A | 6/1976 | Hollyday |
| 3,968,802 A | 7/1976 | Ballis |
| 3,980,975 A | 9/1976 | Maxon et al. |
| 4,188,598 A | 2/1980 | Hunt |
| 4,236,127 A | 11/1980 | Scherba |
| 4,295,467 A | 10/1981 | Mann et al. |
| 4,320,763 A | 3/1982 | Money |
| 4,424,551 A | 1/1984 | Stevenson et al. |
| 4,431,005 A | 2/1984 | McCormick |
| 4,437,474 A | 3/1984 | Peers-Trevarton et al. |
| 4,445,501 A | 5/1984 | Bresler |
| 4,572,198 A | 2/1986 | Codrington |
| 4,585,001 A | 4/1986 | Belt |
| 4,633,181 A | 12/1986 | Murphy-Boesch et al. |
| 4,643,186 A | 2/1987 | Rosen et al. |
| 4,654,880 A | 3/1987 | Sontag |
| 4,672,972 A | 6/1987 | Berke |
| 4,689,621 A | 8/1987 | Kleinberg |
| 4,712,555 A | 12/1987 | Thornander et al. |
| 4,746,864 A | 5/1988 | Satoh et al. |
| 4,754,752 A | 7/1988 | Ginsburg et al. |
| 4,757,820 A | 7/1988 | Itoh |
| 4,766,381 A | 8/1988 | Conturo et al. |
| 4,788,980 A | 12/1988 | Mann et al. |
| 4,799,499 A | 1/1989 | Bisping |
| 4,813,429 A | 3/1989 | Eshel et al. |
| 4,823,812 A | 4/1989 | Eshel et al. |
| 4,832,023 A | 5/1989 | Murphy-Chutorian et al. |
| 4,858,064 A | 8/1989 | Segawa et al. |
| 4,858,623 A | 8/1989 | Bradshaw et al. |
| 4,859,950 A | 8/1989 | Keren |
| 4,932,411 A | 6/1990 | Fritschy et al. |
| 4,940,052 A | 7/1990 | Mann et al. |
| 4,944,298 A | 7/1990 | Sholder |
| 4,960,106 A | 10/1990 | Kubokawa et al. |
| 4,989,608 A | 2/1991 | Ratner |
| 4,991,580 A | 2/1991 | Moore |
| 5,019,075 A | 5/1991 | Spears et al. |
| 5,039,965 A | 8/1991 | Higgins |
| 5,044,375 A | 9/1991 | Bach et al. |
| 5,052,404 A | 10/1991 | Hodgson et al. |
| 5,063,348 A | 11/1991 | Kuhara et al. |
| 5,095,911 A | 3/1992 | Pomeranz |
| 5,099,208 A | 3/1992 | Fitzpatrick et al. |
| 5,167,233 A | 12/1992 | Eberle et al. |
| 5,178,618 A | 1/1993 | Kandarpa |
| 5,190,046 A | 3/1993 | Shturman |
| 5,197,468 A | 3/1993 | Proctor et al. |
| 5,209,233 A | 5/1993 | Holland et al. |
| 5,211,165 A | 5/1993 | Dumoulin et al. |
| 5,217,010 A | 6/1993 | Tsitlik et al. |
| 5,222,506 A | 6/1993 | Patrick et al. |
| 5,246,438 A | 9/1993 | Langberg |
| 5,251,120 A | 10/1993 | Smith |
| 5,268,810 A | 12/1993 | Dimarco et al. |
| 5,271,400 A | 12/1993 | Dumoulin et al. |
| 5,300,108 A | 4/1994 | Rebell et al. |
| 5,306,291 A | 4/1994 | Kroll et al. |
| 5,307,808 A | 5/1994 | Dumoulin et al. |
| 5,307,814 A | 5/1994 | Kressel et al. |
| 5,318,025 A | 6/1994 | Dumoulin et al. |
| 5,323,776 A | 6/1994 | Blakeley et al. |
| 5,323,778 A | 6/1994 | Kandarpa et al. |
| 5,331,505 A | 7/1994 | Wilheim |
| 5,333,095 A | 7/1994 | Stevenson et al. |
| 5,334,045 A | 8/1994 | Cappa et al. |
| 5,334,193 A | 8/1994 | Nardella |
| 5,348,010 A | 9/1994 | Schnall et al. |
| 5,352,979 A | 10/1994 | Conturo |
| 5,358,515 A | 10/1994 | Hurter et al. |
| 5,363,845 A | 11/1994 | Chowdhury et al. |
| 5,365,928 A | 11/1994 | Rhinehart et al. |
| 5,370,644 A | 12/1994 | Langberg |
| 5,398,683 A | 3/1995 | Edwards et al. |
| 5,400,787 A | 3/1995 | Marandos |
| 5,404,880 A | 4/1995 | Throne |
| 5,413,104 A | 5/1995 | Buijs et al. |
| 5,419,325 A | 5/1995 | Dumoulin et al. |
| 5,428,337 A | 6/1995 | Vinclarelli et al. |
| 5,433,717 A | 7/1995 | Rubinsky et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,447,156 A | 9/1995 | Dumoulin et al. |
| 5,450,090 A | 9/1995 | Gels et al. |
| 5,451,232 A | 9/1995 | Rfiinehart et al. |
| 5,462,055 A | 10/1995 | Casey et al. |
| 5,466,254 A | 11/1995 | Helland |
| 5,476,095 A | 12/1995 | Schnall et al. |
| 5,476,483 A | 12/1995 | Bornzin et al. |
| 5,491,300 A | 2/1996 | Huppenthal et al. |
| 5,493,259 A | 2/1996 | Blalock et al. |
| 5,498,261 A | 3/1996 | Strul |
| 5,507,743 A | 4/1996 | Edwards et al. |
| 5,512,825 A | 4/1996 | Atalar et al. |
| 5,514,173 A | 5/1996 | Rebell et al. |
| 5,540,679 A | 7/1996 | Fram et al. |
| 5,545,201 A | 8/1996 | Helland et al. |
| 5,558,093 A | 9/1996 | Pomeranz |
| 5,578,008 A | 11/1996 | Hara |
| 5,588,432 A | 12/1996 | Crowley |
| 5,590,657 A | 1/1997 | Cain et al. |
| 5,591,218 A | 1/1997 | Jacobson |
| 5,620,476 A | 4/1997 | Truex et al. |
| 5,623,241 A | 4/1997 | Minkoff |
| 5,623,724 A | 4/1997 | Gurkovich et al. |
| 5,629,622 A | 5/1997 | Scampini |
| 5,650,759 A | 7/1997 | Hittman et al. |
| 5,662,108 A | 9/1997 | Budd et al. |
| 5,682,897 A | 11/1997 | Pomeranz |
| 5,683,435 A | 11/1997 | Truex et al. |
| 5,685,878 A | 11/1997 | Falwell et al. |
| 5,697,958 A | 12/1997 | Paul et al. |
| 5,699,801 A | 12/1997 | Atalar et al. |
| 5,700,548 A | 12/1997 | Warnier et al. |

(56) References Cited

U.S. PATENT DOCUMENTS

| | | |
|---|---|---|
| 5,706,810 A | 1/1998 | Rubinsky et al. |
| 5,715,825 A | 2/1998 | Crowley |
| 5,716,390 A | 2/1998 | Li |
| 5,722,998 A | 3/1998 | Prutchi et al. |
| 5,735,884 A | 4/1998 | Thompson et al. |
| 5,735,887 A | 4/1998 | Barreras et al. |
| 5,741,321 A | 4/1998 | Brennen |
| 5,751,539 A | 5/1998 | Stevenson et al. |
| 5,757,252 A | 5/1998 | Cho et al. |
| 5,759,202 A | 6/1998 | Schroeppel |
| 5,765,779 A | 6/1998 | Hancock et al. |
| 5,769,800 A | 6/1998 | Gelfand et al. |
| 5,772,693 A | 6/1998 | Brownlee |
| 5,775,338 A | 7/1998 | Hastings |
| 5,779,669 A | 7/1998 | Haissaguerre et al. |
| 5,782,891 A | 7/1998 | Hassler et al. |
| 5,792,055 A | 8/1998 | McKinnon |
| 5,800,467 A | 9/1998 | Park et al. |
| 5,822,174 A | 10/1998 | Yamate et al. |
| 5,824,026 A | 10/1998 | Diaz et al. |
| 5,824,029 A | 10/1998 | Weijand et al. |
| 5,833,608 A | 11/1998 | Acker |
| 5,836,992 A | 11/1998 | Thompson et al. |
| 5,840,031 A | 11/1998 | Crowley |
| 5,851,226 A | 12/1998 | Skubitz et al. |
| 5,855,995 A | 1/1999 | Haq et al. |
| 5,864,234 A | 1/1999 | Luedeke |
| 5,867,361 A | 2/1999 | Seifried et al. |
| 5,868,674 A | 2/1999 | Glowinski et al. |
| 5,879,347 A | 3/1999 | Saadat |
| 5,891,134 A | 4/1999 | Goble et al. |
| 5,896,267 A | 4/1999 | Hittman et al. |
| 5,905,627 A | 5/1999 | Brendel et al. |
| 5,916,162 A | 6/1999 | Snelten et al. |
| 5,928,145 A | 7/1999 | Ocali et al. |
| 5,928,159 A | 7/1999 | Eggers et al. |
| 5,929,729 A | 7/1999 | Swarup |
| 5,938,609 A | 8/1999 | Pomeranz |
| 5,938,692 A | 8/1999 | Rudie |
| 5,959,336 A | 9/1999 | Barsan |
| 5,959,829 A | 9/1999 | Stevenson et al. |
| 5,964,705 A | 10/1999 | Truwit et al. |
| 5,973,906 A | 10/1999 | Stevenson et al. |
| 5,973,907 A | 10/1999 | Reed |
| 5,978,204 A | 11/1999 | Stevenson |
| 6,004,269 A | 12/1999 | Crowley et al. |
| 6,008,980 A | 12/1999 | Stevenson et al. |
| 6,011,995 A | 1/2000 | Guglielmi et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,031,710 A | 2/2000 | Wolf et al. |
| 6,041,496 A | 3/2000 | Haq et al. |
| 6,045,532 A | 4/2000 | Eggers et al. |
| 6,052,614 A | 4/2000 | Morris et al. |
| 6,055,457 A | 4/2000 | Bonner |
| 6,066,136 A | 5/2000 | Geistert |
| 6,099,524 A | 8/2000 | Lipson et al. |
| 6,101,417 A | 8/2000 | Vogel et al. |
| 6,128,522 A | 10/2000 | Acker et al. |
| 6,129,670 A | 10/2000 | Burdette et al. |
| 6,137,161 A | 10/2000 | Gilliland et al. |
| 6,141,594 A | 10/2000 | Flynn et al. |
| 6,146,743 A | 11/2000 | Haq et al. |
| 6,159,560 A | 12/2000 | Stevenson et al. |
| 6,171,240 B1 | 1/2001 | Young et al. |
| 6,171,241 B1 | 1/2001 | McVeigh et al. |
| 6,188,219 B1 | 2/2001 | Reeder et al. |
| 6,198,972 B1 | 3/2001 | Hartlaub et al. |
| 6,209,764 B1 | 4/2001 | Hartlaub et al. |
| 6,226,545 B1 | 5/2001 | Gilderdale |
| 6,236,205 B1 | 5/2001 | Lüdeke et al. |
| 6,238,390 B1 | 5/2001 | Tu et al. |
| 6,252,761 B1 | 6/2001 | Branchevsky |
| 6,263,229 B1 | 7/2001 | Atalar et al. |
| 6,272,370 B1 | 8/2001 | Gillies et al. |
| 6,275,369 B1 | 8/2001 | Stevenson et al. |
| 6,275,379 B1 | 8/2001 | Sleboda et al. |
| 6,280,385 B1 | 8/2001 | Melzer et al. |
| 6,284,080 B1 | 9/2001 | Haq et al. |
| 6,284,971 B1 | 9/2001 | Atalar et al. |
| 6,332,089 B1 | 12/2001 | Acker et al. |
| 6,370,427 B1 | 4/2002 | Alt et al. |
| 6,373,673 B1 | 4/2002 | Anthony |
| 6,390,996 B1 | 5/2002 | Halperin et al. |
| 6,395,637 B1 | 5/2002 | Park et al. |
| 6,408,202 B1 | 6/2002 | Lima et al. |
| 6,414,835 B1 | 7/2002 | Wolf et al. |
| 6,424,234 B1 | 7/2002 | Stevenson |
| 6,428,537 B1 | 8/2002 | Swanson et al. |
| 6,433,653 B1 | 8/2002 | Matsumura et al. |
| 6,456,481 B1 | 9/2002 | Stevenson |
| 6,459,935 B1 | 10/2002 | Piersma |
| 6,470,545 B1 | 10/2002 | Branchevsky |
| 6,473,291 B1 | 10/2002 | Stevenson |
| 6,473,314 B1 | 10/2002 | Custer et al. |
| 6,486,529 B2 | 11/2002 | Chi et al. |
| 6,493,591 B1 | 12/2002 | Stokes |
| 6,512,666 B1 | 1/2003 | Duva |
| 6,529,103 B1 | 3/2003 | Brendel et al. |
| 6,535,766 B1 | 3/2003 | Thompson et al. |
| 6,539,253 B2 | 3/2003 | Thompson et al. |
| 6,539,261 B2 | 3/2003 | Dal Molin |
| 6,549,800 B1 | 4/2003 | Atalar et al. |
| 6,556,009 B2 | 4/2003 | Kellman et al. |
| 6,566,978 B2 | 5/2003 | Stevenson et al. |
| 6,567,259 B2 | 5/2003 | Stevenson et al. |
| 6,567,703 B1 | 5/2003 | Thompson et al. |
| 6,593,884 B1 | 7/2003 | Gilboa et al. |
| 6,606,513 B2 | 8/2003 | Lardo et al. |
| 6,615,483 B2 | 9/2003 | Lindegren |
| 6,628,980 B2 | 9/2003 | Atalar et al. |
| 6,633,780 B1 | 10/2003 | Berger |
| 6,643,903 B2 | 11/2003 | Stevenson et al. |
| 6,654,628 B1 | 11/2003 | Silber et al. |
| 6,660,116 B2 | 12/2003 | Wolf |
| 6,675,033 B1 | 1/2004 | Lardo et al. |
| 6,675,036 B2 | 1/2004 | Kreger et al. |
| 6,675,779 B2 | 1/2004 | King et al. |
| 6,675,780 B1 | 1/2004 | Wendels et al. |
| 6,687,550 B1 | 2/2004 | Doan |
| 6,690,963 B2 | 2/2004 | Ben-Haim et al. |
| 6,694,583 B2 | 2/2004 | Branchevsky |
| 6,697,675 B1 | 2/2004 | Safarevich et al. |
| 6,701,176 B1 | 3/2004 | Halperin et al. |
| 6,714,809 B2 | 3/2004 | Lee et al. |
| 6,728,575 B2 | 4/2004 | Hedberg |
| 6,728,579 B1 | 4/2004 | Lindgren et al. |
| 6,759,388 B1 | 7/2004 | Marchant et al. |
| 6,765,779 B2 | 7/2004 | Stevenson et al. |
| 6,765,780 B2 | 7/2004 | Brendel et al. |
| 6,768,630 B2 | 7/2004 | Togashi |
| 6,771,067 B2 | 8/2004 | Kellman et al. |
| 6,795,730 B2 | 9/2004 | Connelly et al. |
| 6,806,806 B2 | 10/2004 | Anthony |
| 6,823,215 B2 | 11/2004 | Obel et al. |
| 6,829,509 B1 | 12/2004 | MacDonald et al. |
| 6,847,837 B1 | 1/2005 | Melzer et al. |
| 6,868,288 B2 | 3/2005 | Thompson |
| 6,871,091 B2 | 3/2005 | Wilkinson et al. |
| 6,876,885 B2 | 4/2005 | Swoyer et al. |
| 6,882,248 B2 | 4/2005 | Stevenson et al. |
| 6,888,715 B2 | 5/2005 | Stevenson et al. |
| 6,898,454 B2 | 5/2005 | Atalar et al. |
| 6,901,292 B2 | 5/2005 | Hrdlicka et al. |
| 6,904,307 B2 | 6/2005 | Karmarkar et al. |
| 6,925,328 B2 | 8/2005 | Foster et al. |
| 6,930,242 B1 | 8/2005 | Helfer et al. |
| 6,931,283 B1 | 8/2005 | Magnusson |
| 6,931,286 B2 | 8/2005 | Sigg et al. |
| 6,934,588 B1 | 8/2005 | Brand et al. |
| 6,944,489 B2 | 9/2005 | Zeijlemaker et al. |
| 6,944,507 B2 | 9/2005 | Fröberg et al. |
| 6,949,929 B2 | 9/2005 | Gray et al. |

(56) References Cited

U.S. PATENT DOCUMENTS

| | | |
|---|---|---|
| 6,950,696 B2 | 9/2005 | Björling et al. |
| 6,952,613 B2 | 10/2005 | Swoyer et al. |
| 6,971,391 B1 | 12/2005 | Wang et al. |
| 6,985,347 B2 | 1/2006 | Stevenson et al. |
| 6,985,775 B2 | 1/2006 | Reinke et al. |
| 6,987,660 B2 | 1/2006 | Stevenson et al. |
| 6,999,818 B2 | 2/2006 | Stevenson et al. |
| 7,012,192 B2 | 3/2006 | Stevenson et al. |
| 7,013,180 B2 | 3/2006 | Dougherty et al. |
| 7,015,393 B2 | 3/2006 | Weiner et al. |
| 7,035,076 B1 | 4/2006 | Stevenson |
| 7,038,900 B2 | 5/2006 | Stevenson et al. |
| 7,039,455 B1 | 5/2006 | Brosovich et al. |
| 7,046,499 B1 | 5/2006 | Imani et al. |
| 7,047,073 B2 | 5/2006 | Höijer et al. |
| 7,050,855 B2 | 5/2006 | Zeijlemaker et al. |
| 7,068,491 B1 | 6/2006 | Burdon et al. |
| 7,091,412 B2 | 8/2006 | Wang et al. |
| 7,092,766 B1 | 8/2006 | Salys et al. |
| 7,110,227 B2 | 9/2006 | Anthony et al. |
| 7,113,387 B2 | 9/2006 | Stevenson et al. |
| 7,123,013 B2 | 10/2006 | Gray |
| 7,127,294 B1 | 10/2006 | Wang et al. |
| 7,136,273 B2 | 11/2006 | Stevenson et al. |
| 7,148,783 B2 | 12/2006 | Parsche et al. |
| 7,149,578 B2 | 12/2006 | Edvardsson |
| 7,149,773 B2 | 12/2006 | Haller et al. |
| 7,155,271 B2 | 12/2006 | Halperin et al. |
| 7,162,302 B2 | 1/2007 | Wang et al. |
| 7,164,572 B1 | 1/2007 | Burdon et al. |
| 7,164,950 B2 | 1/2007 | Kroll et al. |
| 7,174,219 B2 | 2/2007 | Wahlstrand et al. |
| 7,174,223 B2 | 2/2007 | Money et al. |
| 7,199,995 B2 | 4/2007 | Stevenson |
| 7,211,103 B2 | 5/2007 | Greenberg et al. |
| 7,236,816 B2 | 6/2007 | Kumar et al. |
| 7,236,834 B2 | 6/2007 | Christopherson et al. |
| 7,276,474 B2 | 10/2007 | Marchant et al. |
| 7,301,748 B2 | 11/2007 | Anthony et al. |
| 7,310,216 B2 | 12/2007 | Stevenson et al. |
| 7,319,905 B1 | 1/2008 | Morgan et al. |
| 7,322,832 B2 | 1/2008 | Kronich et al. |
| 7,327,553 B2 | 2/2008 | Brendel |
| 7,363,090 B2 | 4/2008 | Halperin et al. |
| 7,369,898 B1 | 5/2008 | Kroll et al. |
| 7,387,928 B2 | 6/2008 | Cheung |
| 7,388,378 B2 | 6/2008 | Gray et al. |
| 7,422,568 B2 | 9/2008 | Yang et al. |
| 7,423,860 B2 | 9/2008 | Anthony et al. |
| 7,428,136 B2 | 9/2008 | Barnett |
| 7,433,168 B2 | 10/2008 | Anthony |
| 7,436,672 B2 | 10/2008 | Ushijima et al. |
| 7,439,449 B1 | 10/2008 | Kumar et al. |
| 7,446,996 B2 | 11/2008 | Togashi |
| 7,450,396 B2 | 11/2008 | Ye et al. |
| 7,480,988 B2 | 1/2009 | Ok et al. |
| 7,489,495 B2 | 2/2009 | Stevenson |
| 7,495,884 B2 | 2/2009 | Togashi |
| 7,517,769 B2 | 4/2009 | Van Schuylenbergh et al. |
| 7,529,590 B2 | 5/2009 | MacDonald |
| 7,535,693 B2 | 5/2009 | Stevenson et al. |
| 7,551,963 B2 | 6/2009 | Rusin et al. |
| 7,561,906 B2 | 7/2009 | Atalar et al. |
| 7,586,728 B2 | 9/2009 | Anthony |
| 7,593,208 B2 | 9/2009 | Anthony et al. |
| 7,623,335 B2 | 11/2009 | Stevenson et al. |
| 7,675,729 B2 | 3/2010 | Anthony et al. |
| 7,679,926 B2 | 3/2010 | Hsu et al. |
| 7,689,288 B2 | 3/2010 | Stevenson et al. |
| 7,693,576 B1 | 4/2010 | Lavie et al. |
| 7,702,387 B2 | 4/2010 | Stevenson et al. |
| 7,719,854 B2 | 5/2010 | Youker et al. |
| 7,729,770 B2 | 6/2010 | Cabelka et al. |
| 7,733,621 B2 | 6/2010 | Anthony et al. |
| 7,797,048 B2 | 9/2010 | Stevenson et al. |
| 7,812,691 B1 | 10/2010 | Fisk et al. |
| 7,839,146 B2 | 11/2010 | Gray |
| 7,844,319 B2 | 11/2010 | Susil et al. |
| 7,844,343 B2 | 11/2010 | Wahlstrand et al. |
| 7,853,324 B2 | 12/2010 | Stevenson et al. |
| 7,899,551 B2 | 3/2011 | Westlund et al. |
| 7,901,761 B1 | 3/2011 | Jiang et al. |
| 7,957,806 B2 | 6/2011 | Stevenson et al. |
| 7,989,080 B2 | 8/2011 | Greenberg et al. |
| 8,000,804 B1 | 8/2011 | Wessendorf et al. |
| 8,043,454 B1 | 10/2011 | Jiang et al. |
| 8,095,224 B2 | 1/2012 | Truex et al. |
| 8,131,376 B1 | 3/2012 | Greenberg et al. |
| 8,163,397 B2 | 4/2012 | Ok et al. |
| 8,179,658 B2 | 5/2012 | Stevenson et al. |
| 8,219,208 B2 | 7/2012 | Stevenson et al. |
| 8,301,249 B2 | 10/2012 | Min |
| 8,494,635 B2 | 7/2013 | Guebler et al. |
| 8,528,201 B2 | 9/2013 | Guebler et al. |
| 8,588,916 B2 | 11/2013 | Satou et al. |
| 8,604,341 B2 | 12/2013 | Barry et al. |
| 8,653,384 B2 | 2/2014 | Tang et al. |
| 8,659,870 B2 | 2/2014 | Brendel et al. |
| 8,670,829 B2 | 3/2014 | Satou et al. |
| 8,755,887 B2 | 6/2014 | Troetzschel et al. |
| 8,763,245 B1 | 7/2014 | Lucisano et al. |
| 8,841,558 B2 | 9/2014 | Satou et al. |
| 8,855,768 B1 | 10/2014 | Dabney et al. |
| 8,872,035 B2 | 10/2014 | Satou et al. |
| 8,874,206 B2 | 10/2014 | Malinowski et al. |
| 8,886,320 B2 | 11/2014 | Wollenberg et al. |
| 8,927,862 B2 | 1/2015 | Barry et al. |
| 8,929,987 B2 | 1/2015 | Troetzschel et al. |
| 8,938,309 B2 | 1/2015 | Marzano et al. |
| 9,008,779 B2 | 4/2015 | Satou et al. |
| 9,032,614 B2 | 5/2015 | Specht |
| 9,108,066 B2 | 8/2015 | Woods et al. |
| 9,233,253 B2 | 1/2016 | Stevenson et al. |
| 9,407,076 B2 | 8/2016 | Troetzschel et al. |
| 9,418,778 B2 | 8/2016 | Makino et al. |
| 9,427,596 B2 | 8/2016 | Brendel et al. |
| 9,431,814 B2 | 8/2016 | Blilie et al. |
| 9,480,168 B2 | 10/2016 | Troetzschel et al. |
| 9,492,659 B2 | 11/2016 | Brendel et al. |
| 9,552,899 B2 | 1/2017 | Glynn et al. |
| 10,596,369 B2 * | 3/2020 | Stevenson .............. H01G 4/236 |
| 2002/0055678 A1 | 5/2002 | Scott et al. |
| 2002/0095197 A1 | 7/2002 | Lardo et al. |
| 2002/0177771 A1 | 11/2002 | Guttman et al. |
| 2002/0192688 A1 | 12/2002 | Yang et al. |
| 2003/0013928 A1 | 1/2003 | Saruwatari |
| 2003/0013948 A1 | 1/2003 | Russell |
| 2003/0028094 A1 | 2/2003 | Kumar et al. |
| 2003/0028095 A1 | 2/2003 | Tulley et al. |
| 2003/0050557 A1 | 3/2003 | Susil et al. |
| 2003/0053284 A1 | 3/2003 | Stevenson et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0171792 A1 | 9/2003 | Zarinetchi et al. |
| 2003/0179536 A1 | 9/2003 | Stevenson et al. |
| 2003/0204217 A1 | 10/2003 | Greatbatch |
| 2003/0208252 A1 | 11/2003 | O'Boyle et al. |
| 2003/0212373 A1 | 11/2003 | Hall et al. |
| 2003/0213605 A1 | 11/2003 | Brendel et al. |
| 2004/0015079 A1 | 1/2004 | Berger et al. |
| 2004/0034338 A1 | 2/2004 | Thierfelder et al. |
| 2004/0088012 A1 | 5/2004 | Kroll et al. |
| 2004/0167392 A1 | 8/2004 | Halperin et al. |
| 2004/0210289 A1 | 10/2004 | Wang et al. |

(56) References Cited

U.S. PATENT DOCUMENTS

| | | |
|---|---|---|
| 2004/0230271 A1 | 11/2004 | Wang et al. |
| 2004/0249428 A1 | 12/2004 | Wang et al. |
| 2004/0263173 A1 | 12/2004 | Gray |
| 2004/0263174 A1 | 12/2004 | Gray et al. |
| 2005/0007718 A1 | 1/2005 | Stevenson et al. |
| 2005/0070972 A1 | 3/2005 | Wahlstrand et al. |
| 2005/0113669 A1 | 5/2005 | Helfer et al. |
| 2005/0113676 A1 | 5/2005 | Weiner et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0197677 A1 | 9/2005 | Stevenson |
| 2005/0201039 A1 | 9/2005 | Stevenson et al. |
| 2005/0215914 A1 | 9/2005 | Bornzin et al. |
| 2005/0222642 A1 | 10/2005 | Przybyszewski et al. |
| 2005/0222647 A1 | 10/2005 | Wahlstrand et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0247472 A1 | 11/2005 | Helfer et al. |
| 2005/0248340 A1 | 11/2005 | Berkcan et al. |
| 2005/0248907 A1 | 11/2005 | Stevenson et al. |
| 2006/0009819 A1 | 1/2006 | Przybyszewski |
| 2006/0025820 A1 | 2/2006 | Phillips et al. |
| 2006/0028784 A1 | 2/2006 | Brendel |
| 2006/0030774 A1 | 2/2006 | Gray et al. |
| 2006/0032665 A1 | 2/2006 | Ice |
| 2006/0041294 A1 | 2/2006 | Gray |
| 2006/0085043 A1 | 4/2006 | Stevenson |
| 2006/0100506 A1 | 5/2006 | Halperin et al. |
| 2006/0119361 A1 | 6/2006 | Karmarkar et al. |
| 2006/0200218 A1 | 9/2006 | Wahlstrand |
| 2006/0211979 A1 | 9/2006 | Smith et al. |
| 2006/0212096 A1 | 9/2006 | Stevenson |
| 2006/0221543 A1 | 10/2006 | Stevenson et al. |
| 2006/0229693 A1 | 10/2006 | Bauer et al. |
| 2006/0247684 A1 | 11/2006 | Halperin et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0259093 A1 | 11/2006 | Stevenson et al. |
| 2006/0271138 A1 | 11/2006 | MacDonald |
| 2007/0035910 A1 | 2/2007 | Stevenson |
| 2007/0043399 A1 | 2/2007 | Stevenson et al. |
| 2007/0083244 A1 | 4/2007 | Stevenson et al. |
| 2007/0088416 A1 | 4/2007 | Atalar et al. |
| 2007/0093142 A1 | 4/2007 | MacDonald et al. |
| 2007/0106332 A1 | 5/2007 | Denker et al. |
| 2007/0112398 A1 | 5/2007 | Stevenson et al. |
| 2007/0123949 A1 | 5/2007 | Dabney et al. |
| 2007/0167867 A1 | 7/2007 | Wolf |
| 2007/0168005 A1 | 7/2007 | Gray |
| 2007/0168006 A1 | 7/2007 | Gray |
| 2007/0179554 A1 | 8/2007 | Iyer et al. |
| 2007/0179577 A1 | 8/2007 | Marshall et al. |
| 2007/0203529 A1 | 8/2007 | Iyer et al. |
| 2007/0208383 A1 | 9/2007 | Williams |
| 2007/0250143 A1 | 10/2007 | Sommer et al. |
| 2007/0255332 A1 | 11/2007 | Cabelka et al. |
| 2007/0255377 A1 | 11/2007 | Marshall et al. |
| 2007/0288058 A1 | 12/2007 | Halperin et al. |
| 2007/0299490 A1 | 12/2007 | Yang et al. |
| 2008/0004670 A1 | 1/2008 | McVenes et al. |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0049410 A1 | 2/2008 | Kawaguchi et al. |
| 2008/0051854 A1 | 2/2008 | Bulkes et al. |
| 2008/0071313 A1 | 3/2008 | Stevenson et al. |
| 2008/0116997 A1 | 5/2008 | Dabney et al. |
| 2008/0132986 A1 | 6/2008 | Gray et al. |
| 2008/0132987 A1 | 6/2008 | Westlund et al. |
| 2008/0140149 A1 | 6/2008 | John et al. |
| 2008/0158746 A1 | 7/2008 | Anthony et al. |
| 2008/0161886 A1 | 7/2008 | Stevenson et al. |
| 2008/0195180 A1 | 8/2008 | Stevenson et al. |
| 2008/0195186 A1 | 8/2008 | Li et al. |
| 2008/0195187 A1 | 8/2008 | Li et al. |
| 2008/0221638 A1 | 9/2008 | Wedan et al. |
| 2008/0239622 A1 | 10/2008 | Hsu et al. |
| 2008/0243218 A1 | 10/2008 | Bottomley et al. |
| 2008/0247111 A1 | 10/2008 | Anthony et al. |
| 2008/0247116 A1 | 10/2008 | Kawano et al. |
| 2008/0247117 A1 | 10/2008 | Elam et al. |
| 2008/0262584 A1 | 10/2008 | Bottomley et al. |
| 2008/0262592 A1 | 10/2008 | Jordan et al. |
| 2008/0264685 A1 | 10/2008 | Park et al. |
| 2008/0269591 A1 | 10/2008 | Halperin et al. |
| 2008/0277153 A1 | 11/2008 | Teshome et al. |
| 2009/0036944 A1 | 2/2009 | Fonte |
| 2009/0097219 A1 | 4/2009 | Cho et al. |
| 2009/0099440 A1 | 4/2009 | Viohl |
| 2009/0099555 A1 | 4/2009 | Viohl et al. |
| 2009/0107717 A1 | 4/2009 | Hsu et al. |
| 2009/0116167 A1 | 5/2009 | Stevenson et al. |
| 2009/0128976 A1 | 5/2009 | Anthony |
| 2009/0139760 A1 | 6/2009 | Tanaka |
| 2009/0163974 A1 | 6/2009 | Taylor et al. |
| 2009/0163980 A1 | 6/2009 | Stevenson |
| 2009/0180237 A1 | 7/2009 | Hou et al. |
| 2009/0187229 A1 | 7/2009 | Lavie |
| 2009/0236141 A1 | 9/2009 | Kim et al. |
| 2009/0243756 A1 | 10/2009 | Stevenson et al. |
| 2009/0270948 A1 | 10/2009 | Nghiem et al. |
| 2009/0281592 A1 | 11/2009 | Vase |
| 2009/0312835 A1 | 12/2009 | Stevenson |
| 2010/0010602 A1 | 1/2010 | Wedan et al. |
| 2010/0016936 A1 | 1/2010 | Stevenson et al. |
| 2010/0023000 A1 | 1/2010 | Stevenson et al. |
| 2010/0023095 A1 | 1/2010 | Stevenson et al. |
| 2010/0046135 A1 | 2/2010 | Niki et al. |
| 2010/0046137 A1 | 2/2010 | Adachi |
| 2010/0076538 A1 | 3/2010 | Desai et al. |
| 2010/0109958 A1 | 5/2010 | Haubrich et al. |
| 2010/0109966 A1 | 5/2010 | Mateychuk et al. |
| 2010/0114246 A1 | 5/2010 | Hill et al. |
| 2010/0114276 A1 | 5/2010 | Min et al. |
| 2010/0114277 A1 | 5/2010 | Zhao et al. |
| 2010/0138192 A1 | 6/2010 | Min |
| 2010/0149042 A1 | 6/2010 | Utsi et al. |
| 2010/0151113 A1 | 6/2010 | Shelton |
| 2010/0160989 A1 | 6/2010 | Legay |
| 2010/0174348 A1 | 7/2010 | Bulkes et al. |
| 2010/0174349 A1 | 7/2010 | Stevenson et al. |
| 2010/0198312 A1 | 8/2010 | Stevenson et al. |
| 2010/0217262 A1 | 8/2010 | Stevenson et al. |
| 2010/0217264 A1 | 8/2010 | Odom et al. |
| 2010/0217341 A1 | 8/2010 | John et al. |
| 2010/0234907 A1 | 9/2010 | Dobak |
| 2010/0241206 A1 | 9/2010 | Truex et al. |
| 2011/0043297 A1 | 2/2011 | Stevenson et al. |
| 2011/0248184 A1 | 10/2011 | Shah |
| 2012/0006576 A1 | 1/2012 | Barry et al. |
| 2012/0197335 A1 | 8/2012 | Reisinger |
| 2013/0032378 A1 | 2/2013 | Morioka et al. |
| 2013/0058003 A1 | 3/2013 | Iyer et al. |
| 2013/0138186 A1 | 5/2013 | Iyer et al. |
| 2013/0184796 A1 | 7/2013 | Marzano et al. |
| 2014/0151114 A1 | 6/2014 | Morioka et al. |
| 2014/0168850 A1 | 6/2014 | Stevenson et al. |
| 2014/0168917 A1 | 6/2014 | Marzano et al. |
| 2014/0243944 A1 | 8/2014 | Stevenson et al. |
| 2015/0004359 A1 | 1/2015 | Shahbazi et al. |
| 2015/0217111 A1 | 8/2015 | Stevenson et al. |
| 2015/0245468 A1 | 8/2015 | Barry et al. |
| 2015/0283374 A1 | 10/2015 | Kronmueller et al. |
| 2015/0314131 A1 | 11/2015 | Marzano et al. |
| 2015/0343224 A1 | 12/2015 | Woods et al. |
| 2016/0151635 A1 | 6/2016 | Frysz et al. |

(56) References Cited

U.S. PATENT DOCUMENTS

| | | | |
|---|---|---|---|
| 2016/0287883 A1 | 10/2016 | Barry et al. | |
| 2018/0126175 A1 | 5/2018 | Seitz et al. | |

FOREIGN PATENT DOCUMENTS

| | | |
|---|---|---|
| EP | 0466424 | 1/1992 |
| EP | 0557127 | 8/1993 |
| EP | 0673621 | 9/1995 |
| EP | 0498996 | 3/1997 |
| EP | 1021730 | 4/2003 |
| EP | 0930509 | 3/2004 |
| EP | 1469910 | 12/2006 |
| EP | 1883449 | 1/2009 |
| EP | 2025361 | 2/2009 |
| FR | 2811900 B1 | 2/2003 |
| JP | 60141034 | 7/1985 |
| JP | 61181925 | 8/1986 |
| JP | 62233905 | 10/1987 |
| JP | 4071536 | 3/1992 |
| JP | 6054823 | 3/1994 |
| JP | 06070902 | 3/1994 |
| JP | 6176962 | 6/1994 |
| JP | 7272975 | 10/1995 |
| JP | 9094238 | 4/1997 |
| JP | 11239572 | 9/1999 |
| JP | 2004254257 | 9/2004 |
| JP | 2004289760 | 10/2004 |
| JP | 2005117606 | 4/2005 |
| JP | 2007129565 | 5/2007 |
| WO | 8704080 | 7/1987 |
| WO | 9210213 | 6/1992 |
| WO | 9423782 | 10/1994 |
| WO | 9740396 | 10/1997 |
| WO | 9852461 | 11/1998 |
| WO | 9919739 | 4/1999 |
| WO | 0010456 | 3/2000 |
| WO | 0025672 | 5/2000 |
| WO | 02083016 | 10/2002 |
| WO | 2003037424 | 5/2003 |
| WO | 2003063946 | 8/2003 |
| WO | 2003063952 | 8/2003 |
| WO | 2003063953 | 8/2003 |
| WO | 2003063955 | 8/2003 |
| WO | 2003063956 | 8/2003 |
| WO | 2003063957 | 8/2003 |
| WO | 2005081784 | 9/2005 |
| WO | 2005102445 | 11/2005 |
| WO | 2005102446 | 11/2005 |
| WO | 2005102447 | 11/2005 |
| WO | 2005115531 | 12/2005 |
| WO | 2006093685 | 9/2006 |
| WO | 2007047966 | 4/2007 |
| WO | 2007089988 | 8/2007 |
| WO | 2007102893 | 9/2007 |
| WO | 2007145671 | 12/2007 |
| WO | 2008077037 | 6/2008 |
| WO | 2008111986 | 9/2008 |
| WO | 2010008833 | 1/2010 |
| WO | 2013/158552 | 10/2013 |

OTHER PUBLICATIONS

Roguin, et al., "Modem Pacemaker and Implantable Cardioverter/Defibrillator systems Can Be Magnetic Resonance Imaging Safe", Journal of the American Heart Association, Aug. 4, 2004, 475-482.

Sakabe, et al., "High Frequency Performance of Multilayer Ceramic Capacitors", Electronic Components and Technology Confrence, 1995, Proceedings 45TH, May 21, 1995, 234-240.

Sarda, et al., "Ceramic EMI Filters—A Review", American Ceramic Society Bulletin; vol. 67, No. 4, 1988, 737-746.

Shellock, et al., "Comparative Analyses of MR-Induced Distal Heating in Novel Filtered Cardiac Pacing Leads UsingTwo Geometric Configurations", 17th Scientific Meeting & Exhibition of the International Society for Magnetic Resonance in Medicine, Honolulu, Hawaii, Apr. 2009, 3014.

(56) References Cited

OTHER PUBLICATIONS

Shellock, "MRI Issues for Neuromodulation Devices", Institute for Magnetic Resonance Safety Education, and Research (IMRSER).

Susil, et al., "Multifunctional Interventional Devices for MRI: A Combined Electrophysiology/MRI Catheter", 2002, 594-600.

Susil, et al., "U.S. Appl. No. 60/283,725", Multifunctional Interventional Devices for Use in MRI, Apr. 13, 2001.

Weiner, et al., "U.S. Appl. No. 60/269,817", Electromagnetic Interference immune Cardiac Assist System, Feb. 20, 2001.

Wilk, et al., "High-K Gate Dielectrics: Current Status and Materials Properties Considerations", Journal of Applied Physi s, vol. 89, No. 10, May 15, 2001, 5243-5275.

European Search Report, Application 10167031.3, dated Sep. 19, 2012.

Gabriel, et al., "The Dielectric Properties of Biological Tissues: II", Measurements in the Frequency Range 10 Hz to 20 GHz, Apr. 2, 1996, 2251-2269.

Gabriel, et al., "The Dielectric Properties of Biological Tissues: Parametric Models for the Dielectric Spectrum of Tissues", Parametric Models for the Dielectric Spectrum of Tissues, Phys. Med. Bio. 41, 1996, 2271-2291.

Johnson, et al., "Characterization of the Relationship between MR-Induced Distal Tip Heating in Cardiac Pacing Leads and Electrical Performance of Novel Filtered Tip Assemblies", 17th Scientific Meeting & Exhibition of the International Society for Magnetic Resonance in Medicine, Honolulu, Hawaii, Apr. 2009, 307.

Karbasi, "Developing a High Density PT/Alumina Hermetic Feedthrough", Florida International University, FIU Digital Commons, FIU Electronic Theses and Dissertations, University Graduate School, Published Jun. 15, 2012.

Kingery, et al., "Atom Mobility in Introduction to Ceramics, 2nd Edition", Published in New York, Wiley, copyright 1976, pp. 217-263.

Kingery, et al., "Surfaces, Interfaces, and Grain Boundaries in Introduction to Ceramics", 2nd Edition, Published in New York, Wiley, copyright 1976, pp. 177-215.

Konings, et al., "Heating Around Intravascular Guidewires by Resonating RF Waves", Journal of Magnetic Resonance Imaging, 2000, 79-85.

Lamouri, et al., "Control of the a-alumina to a-alumina phase transformation for an optimized alumina densification", Boletin de la Sociedad Espanola De Ceramica Y Vidrio 56 (2017) pp. 47-54.

Luchinger, "Safety Aspects of Cardiac Pacemakers in Magnetic Resonance Imaging", A dissertation submitted to the Swiss Federal Institute of Technology Zurich, Switzerland, 2002.

European Search Report, Application No. 15165863.0, dated Sep. 12, 2016.

European Search Report, Application No. 18150642.9, dated Jun. 6, 2018.

European Search Report, Application No. 12157697.9, dated Jul. 5, 2012.

Extended European Search Report, Application 17201160.3, dated Apr. 16, 2018.

Extended European Search Report, Application No. 16175505.3, dated Nov. 15, 2016.

Extended European Search Report, Application No. 18177098.3, dated Aug. 8, 2018.

"Holy Stone Enterprise", Ceramic Capacitor Catalog 2008-2009, May 2008.

"Wikipedia article", EIA Class 1 dielectric., Sep. 13, 2006.

Balanis, "Advanced Engineering Electromagnetics", 1989.

Becker, "Die Keimbildung Bei Der Ausscheidung in Metallischen Mischkristallen", Published in Annalen der Physik, Issue 5, vol. 32, 1938, pp. 128-140.

Boser, et al., "High Frequency Behavior of Ceramic Multilayer Capacitors", IEEE Transactions on Components, Hybrids, and Manufacturing Technology, vol. CHMT-10, No. 3, Sep. 1987, 437-439.

Clement, et al., "Estimation of Effective Lead Loop Area for Implantable Pulse Generators and Cardioverter/ Defibrillators for Determination of Susceptibility to Radiated Electromagnetic Interference", AAMI EMC Task Force, Apr. 12, 2004, 10 pages.

Ennis, et al., "Cautions About the Use of Equivalent Series Resistance (ESR) in Specifying Capacitors", Mar. 8, 1993, 58-64.

European Search Report, Application No. 10167031.3, dated Sep. 19, 2012.

\* cited by examiner 132
(CAPACITOR)
112
(FERRULE)

BODY FLUID SIDE

HERMETIC TERMINAL FOR AN ACTIVE IMPLANTABLE MEDICAL DEVICE HAVING A FEEDTHROUGH CAPACITOR PARTIALLY OVERHANGING A FERRULE FOR HIGH EFFECTIVE CAPACITANCE AREA

CROSS REFERENCE TO RELATED APPLICATIONS

This application is a continuation-in-part of U.S. application Ser. No. 16/121,716, filed on Sep. 5, 2018, now U.S. Pat. No. 10,596,369, which is a continuation of U.S. application Ser. No. 15/943,998, filed on Apr. 3, 2018, now U.S. Pat. No. 10,350,421, which claims priority to U.S. provisional application Ser. No. 62/646,552, filed on Mar. 22, 2018, the contents of which are fully incorporated herein by reference.

FIELD OF THE INVENTION

The present invention generally relates to active implantable medical devices and hermetic terminal subassemblies. More particularly, the present invention relates to a hermetic terminal for an active implantable medical device having a capacitor that overhangs the ferrule on at least one side and then also does not overhang the ferrule on another side.

BACKGROUND OF THE INVENTION

FIG. 1 illustrates various types of active implantable and external medical devices 100 that are currently in use. FIG. 1 is a wire formed diagram of a generic human body showing a number of implanted medical devices. 100A is a family of external and implantable hearing devices which can include the group of hearing aids, cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of a seizure and also providing electrical stimulation to brain tissue to prevent the seizure from actually happening. The leadwires that come from a deep brain stimulator are often placed using real time imaging. Most commonly such leadwires are placed during real time MRI. 100C shows a cardiac pacemaker, which is well-known in the art, and which may have endocardial or epicardial leads. Implantable pacemakers may also be leadless. The family of cardiac pacemakers 100C includes the cardiac resynchronization therapy devices (CRT-D pacemakers) and leadless pacemakers. CRT-D pacemakers are unique in that they provide electrical stimulation therapy to pace both the right and the left sides of the heart. The family also includes all types of implantable loop recorders or biologic monitors, such as cardiac monitors. Referring once again to element 100C, the cardiac pacemaker could also be any type of biologic monitoring and/or data recording device, including loop recorders or the like. 100D includes the family of left ventricular assist devices (LVADs) and artificial hearts. 100E includes an entire family of drug pumps which can be used for dispensing of insulin, chemotherapy drugs, pain medications and the like. Insulin pumps are evolving from passive devices to ones that have sensors and closed loop systems, which permit real time monitoring of blood sugar levels. These devices tend to be more sensitive to EMI than passive pumps that have no sense circuitry or externally implanted leadwires. 100F includes a variety of external or implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillator (ICD) devices and also includes the family of congestive heart failure devices (CHF). CHF devices are also known in the art as cardio resynchronization therapy devices or CRT devices. Although 100I is described as an implantable defibrillator, it is noted that, like pacemakers, these implantable cardioverter defibrillators can have either endocardial or epicardial leads. Additionally, implantable defibrillators also includes a new family of subcutaneous defibrillators. As used herein, ICDs include subcutaneous defibrillators, CHF, CRT and CRT-D devices. CRT devices of the ICD family are cardiac resynchronization therapy devices that not only provides electrical stimulation therapy to pace the heart but is also capable of providing high-voltage defibrillation therapy when required. 100J illustrates an externally worn pack. This pack could be an external insulin pump, an external drug pump, an external neurostimulator, a Holter monitor with skin electrodes or even a ventricular assist device power pack. As used herein, the term AIMD includes any device implanted in the human body that has at least one electronic component.

FIG. 2 illustrates a side view of prior art cardiac pacemaker 100C. The pacemaker electronics are housed in a hermetically sealed and conductive electromagnetic shield 116 (typically titanium). There is a header block assembly 101 generally made of thermal-setting non-conductive plastic, such as Tecothane®. This header block assembly 101 houses one or more connector assemblies generally in accordance with ISO Standards IS-1, IS-2, or more modern standards, such as IS4 or DF4. These header block connector port assemblies are shown as 103 and 103'. Implantable leadwires 107, 107' have proximal plugs 105, 105' and are designed to insert into and mate with these header block connector cavities 103 and 103', or, in devices that do not have header block assemblies, are built directly into the pulse generator itself.

As used herein, the term "lead" refers to an implantable lead containing a lead body and one or more internal lead conductors. A "lead conductor" refers to the conductor that is inside of an implanted lead body. The term "leadwire" or "lead wire" refers to wiring that is either inside of the active implantable medical device (AIMD) housing or inside of the AIMD header block assembly or both. Furthermore, as used herein, in general, the terms lead, leadwire and pin are all used interchangeably. Importantly, they are all electrical conductors. This is why, in the broad sense of the term, lead, leadwire or pin can all be used interchangeably since they are all conductors. The term "conductive pathway" can also be used to be synonymous with lead conductor, lead, leadwire or pin or even a circuit trace. As described herein, composite conductive sintered paste filled vias passing through an insulator in nonconductive relation with a ferrule electrically acts the same as a leadwire, lead wire, or pin. These sintered-paste filled vias (conductive pathway) may also incorporate co-fired solid leadwires (conductive pathway). As used herein, the term paste generally refers to pastes, inks, gels, paints, cermets, and other such metal and/or metal/ceramic sinterable material combinations that can be flowable, injectable, pressed, pulled, pushed or otherwise movable into an orifice or via. Post-sintering, the solvents and binders are baked out and, after sintering, the paste becomes a densified solid with monolithic structure. For example, see FIGS. 44A-46 herein.

Referring now back to FIG. 2, one will appreciate that the active implantable medical device 100C, in this case, would be a cardiac pacemaker, an implantable cardioverter defibrillator (ICD) or a cardiac resynchronization device, such as cardiac resynchronization pacemakers (CRT-P) or cardiac resynchronization defibrillators (CRT-D) devices. It will be further appreciated that the pulse generator 100C illustrated in FIG. 2, could be various types of neurostimulators, which may or may not have a Tecothane® header block, as illustrated. Some neurostimulators have their own plugs and connectors and others, such as cochlear implants, may be directly wired from the active implantable medical device or pulse generator (PG), for example, to the cochlear nerve bundle.

Additionally, AIMD, as defined herein, includes electronic circuits disposed within the human body that have a primary or secondary battery, or have an alternative energy source, such as energy induced by motion, thermal or chemical effects or through external induction. As used herein, the term "header block" is the biocompatible material that attaches between the AIMD housing and the lead. The term "header block connector assembly" refers to the header block including the connector ports for the leads and the wiring connecting the lead connector ports to the hermetic terminal subassemblies which allow electrical connections to hermetically pass inside the device housing. It is also understood by those skilled in the art that the present invention can be applicable to active implantable medical devices that do not have a header block or header block connector assemblies such as pulse generators. Referring once again to FIG. 2, one can see that EMI (or electromagnetic interference) is showing undesirably coupling to implanted leads 107 and 107'. Electromagnetic interference is very common in a patient environment and includes signals from cellular telephones, microwave ovens, airport radars and the like.

FIG. 2A shows the wire man of FIG. 1 (a human patient) with an implanted active implantable medical device 100C and implanted leadwires 107, as shown. The patient, in this case, is holding a cellular telephone, which is producing a very strong radio frequency (RF) field. One can see that as this field propagates, it cuts across the implanted leadwires 107 where this electromagnetic interference energy (RF), otherwise known as EMI, is couple onto the leads.

The generally titanium conductive housing 116 of the AIMD forms an electromagnetic shield and protects internal electronics from radiated interference. Once electromagnetic interference is coupled to leadwires, it can be undesirably conductively coupled through the header block 101 and through the hermetic terminal feedthrough assembly 120 to device electronics, such as those indicated by device circuit board 122. In the prior art, it is very common that a feedthrough filter capacitor 132 be disposed at the point of leadwire entry into the shielded housing 116. The purpose of the feedthrough is to decouple the unwanted high frequency electromagnetic interference and divert it harmlessly to the overall electromagnetic shield 116. In this way, the conductive EMI cannot reach the sensitive AIMD electronic circuits. For example, in a cardiac pacemaker, electromagnetic interference can be interpreted by the device electronics as a normal heartbeat and thereby, cause the pacemaker to inhibit. This means that the pacing pulses would cease, which would become immediately life-threatening for a pacemaker dependent patient.

FIG. 3 illustrates a prior art unipolar feedthrough capacitor 132. A quadpolar feedthrough capacitor 132 was previously illustrated in prior art FIG. 2. However now referring back to FIG. 3, one can see that there is an external metallization 142 and a passageway or feedthrough hole metallization 144. This metallization can be applied by electroplating or by applying a metal fritted glass, which is then fired. In one embodiment, the fritted glass may comprise a silver or palladium silver glass matrix. In any event, after application of the metallization layers 142 and 144, one can make electrical contact to the feedthrough capacitor either by soldering or using thermal-setting conductive adhesives or the like. As shown, the feedthrough capacitor comprises active electrode plates 148 and ground electrode plates 146. The reason the electrode plates 146 are called ground electrode plates and as will be further explained herein, is because the perimeter or outside diameter metallization 142 is configured to be attached to a ferrule 112 and in turn, to the conductive housing 116 of an AIMD, which forms an equipotential surface for energy dissipation (aka ground). Referring once again to FIG. 2, one can see that the housing 116, for an active implantable medical device, is generally metallic (titanium). One can also see that the feedthrough capacitor 132 is attached to a hermetically sealed subassembly 120 of the AIMD, which acts as an equipotential surface (ground).

FIG. 3A is taken generally from section 3A-3A from FIG. 3. Shown in exploded view, are ceramic cover sheets 147, active electrodes 148 that are disposed on ceramic layers 149 and ground electrode plates 146 that are disposed on ceramic layers 149. These are stacked up with cover sheets on the opposite end 147 and then pressed and laminated. It will be appreciated that blank cover sheets 147 can be disposed between the active layers 148 and the ground layers 146 thereby, increasing the dielectric thickness and increasing the voltage rating of the device. The electrode layers 148 and 146 are typically applied by silk-screening or equivalent waterfall processes.

FIG. 4 is a cross-sectional view showing the unipolar capacitor 132 of FIG. 3 mounted to a ferrule 112 of a hermetic seal subassembly 120 for an AIMD. As can be seen, the ground metallization 142 of the feedthrough capacitor 132 is electrically connected 152 to the ferrule 112 of the hermetic seal. The hermetic seal is accomplished generally by gold brazing 162 between an alumina insulator 160. There is an outside diameter gold braze 150 between the insulator and the ferrule 112. There is also a gold braze 162 between leadwires 114, 111 and the inside diameter of an insulator 160 passageway as illustrated. In order for gold braze material 150, 162 to wet to the insulator surfaces 160, there must first be an adhesion layer 153 and then a wetting layer 151, as illustrated. In one embodiment, the adhesion layer can be a sputtered layer of titanium, followed by a sputtered layer of molybdenum or niobium (the wetting layer). In some manufacturing agent operations, the adhesion and wetting layers can be combined into a single layer. Throughout the present invention, sometimes in order to simplify the drawings, the adhesion layer 153 and wetting layer 151 are not shown or at least not described. But it will be understood that anywhere that a gold braze 150, 162 is described herein to an insulator 160, that an adhesion/wetting layer is required.

Referring once again to FIG. 4, shown is a prior art unipolar discoidal. In the case where this unipolar discoidal was intended for use in an AIMD known as an implantable cardioverter defibrillator, this would mean that the capacitor 132 would have to handle high-voltage pulses when the implantable defibrillator delivers its high-voltage cardioversion shock to heart tissues. When the high-voltage wave front travels to the heart, the feedthrough capacitor 132, which is sitting there uncharged, must suddenly charge up to the full defibrillator pulse voltage, which can be on the order of 700 to 850 volts. Studies by the inventors have shown that this voltage can conductively ring up to as high as 1200 volts. Looking carefully at the unipolar capacitor 132 of FIG. 4, one can see that there is a ground electrode plate 146 oriented on the bottom of the unipolar feedthrough capacitor towards the AIMD electronics and that on the top of the feedthrough capacitor, there is a second ground electrode plate 146 disposed towards the body fluid side. In other words, the side of the capacitor that is mounted to at least one of the ferrule 112 and the insulator 160. These upper and lower ground electrode plates can also be seen in the partial section of FIG. 3. One can see that there is a ground electrode plate connected to the capacitor's diameter metallization 142, which is its ground metallization, which is connected to the ferrule. Again, there is a ground electrode plate 146 oriented up and down. When one performs equipotential high-voltage modeling of the stresses both inside and outside the capacitor, having a ground electrode plate disposed both upwardly and downwardly constrains the high-voltage fields to the inside of the capacitor. This prevents high-voltage fields from occurring between the bottom of the capacitor and the conductive ferrule 112 or, on the top of the capacitors to other structures inside of the AIMD, such as a circuit board or a battery housing or any of the other conductive objects. Accordingly, there is an advantage to having a ground plate up and a ground plate down to manage the electric fields in and around a feedthrough capacitor.

As defined herein, what is referred to as the insulator is generally disposed between or inside a ferrule opening and has either lead conductors or conductive passageways or vias that pass through the hermetic terminal subassembly 120. The ceramic capacitor 132 also uses insulative materials, which are dielectrics. As previously described in FIG. 3A, these dielectric sheets 147,149 are referred to as dielectrics although it is appreciated that they are also insulative. In summary, as used herein, insulators are the insulators that are gold brazed to a ferrule of the AIMD, whereas capacitor dielectric insulators are referred to as dielectric layers. Referring once again to FIG. 4, it will also be appreciated that instead of alumina insulator with corresponding gold brazes 150 and 162, the hermetic seal insulator could comprise glass or glass ceramics, which would either be directly fused or compressed to the corresponding ferrule 42 and leadwire 111 thereby, eliminating the need for gold brazes. Throughout the drawings showing in the patent, it will be appreciated that hermetic seal insulators could be replaced by glass or glass ceramic insulators. The insulator 160 partially resides inside of a hole that passes through the ferrule 112. This is from a body fluid side to the device side, as shown. It will be appreciated that the insulator 160 need not be disposed inside of a ferrule opening. Instead, the insulator 160 could be disposed on top of the ferrule and gold braze 150 could connect the insulator 160 to the top ferrule surface 112.

Referring once again to FIG. 4, one can see that the ferrule 112 of the hermetic seal has been laser welded 154 into the overall housing 116 of the AIMD. This is very important in that the feedthrough capacitor ground metallization 142 becomes part of the overall electromagnetic shield of the AIMD housing. This forms in the industry what is known as a Faraday cage and provides an effective electromagnetic interference shield and energy dissipating surface. Referring back to FIG. 4, lead 114 on the body fluid side is generally connected to implanted leadwires and tissue stimulating electrodes (not shown). Referring back to FIG. 2 for a prior art pacemaker, one can see these leadwires 107 and 107' that are connected to electrodes 109 that are located within the human heart. Again, referring to FIGS. 2 and 2A, undesirably, electromagnetic interference (EMI) can be coupled to these implanted leads and in turn, to the interior of the AIMD housing. It has been shown in numerous articles that EMI can disrupt the proper operation of the AIMD, such as a cardiac pacemaker and lead to improper therapy or even complete inhibition of therapy. Inhibition of therapy, for a cardiac pacemaker, can be immediately life-threatening to a pacemaker dependent patient.

Referring once again to FIG. 4, electromagnetic interference signals therefore, may be conducted along leadwire 114 to terminal 1 of the feedthrough capacitor. It is the purpose of the feedthrough capacitor 132 to divert unwanted high-frequency EMI signals from the leadwire 114, 111 so that by the time the signals reach terminal 2 (the AIMD electronics or device side), that the electromagnetic interference has been greatly attenuated or diverted through the feedthrough capacitor, harmlessly to the AIMD housing 116. Referring back to FIG. 4, one will appreciate that the leadwire coming from the body fluid side 114 passes through the insulator 160 and the feedthrough capacitor 132. The leadwire is a continuous conductor but is labeled 111 on the device side. In other words, the leadwire has a body fluid portion 114 and a device side portion 111.

This is further appreciated by looking at the schematic diagram of FIG. 4A. Electromagnetic interference signals enter terminal 1 of the 3-terminal feedthrough capacitor and are diverted harmlessly to the ground terminal 3 (116) before they can reach the device side 111, terminal 2. The feedthrough capacitors ground electrode plate 146, when properly installed, acts electrically as a continuous part of the titanium shield 116, which houses the active implantable medical device (AIMD). The feedthrough capacitor is a 3-terminal coaxial device whose internal electrode plates "plug the insulator hole" and both reflect and absorb EMI fields. Referring back to FIG. 4 and imagining that the feedthrough capacitor 132 has been removed, the insulator 160 acts as a wave guide. At certain frequencies, radiated electromagnetic interference may pass right through the insulator just like light passes through a window. This can be very problematic for a closely held emitter, such as a cellular telephone, which may even be placed in a shirt pocket right over the implant. Importantly, the feedthrough capacitor 132, when properly installed, plugs this RF hole or window (wave guide), such that its active and ground electrode plates form a continuous part of the shield. The feedthrough capacitor is novel in that, it is a broadband low pass filter, which allows desirable frequencies (like pacing pulses) to pass. Because it is a unique 3-terminal coaxial device, it provides effective attenuation to undesired signals (EMI) over a very broad band (10 MHz to 10 GHz frequency range). When designed and installed properly, feedthrough capacitors are very low inductance devices, which do not series resonate. It is very important that feedthrough capacitors be installed in such a way that undesirable resistances, for example, due to titanium oxides, cannot occur in the ground connection.

FIG. 5A illustrates a quadpolar feedthrough capacitor (meaning four passageways), such as previously illustrated in FIG. 2. It will be appreciated that any number of feedthrough holes 134 can be produced. As previously described for the unipolar capacitor of FIG. 3, the quadpolar capacitor of FIG. 5A, has ground metallization 142 and four passageways 134, each having their own active metallization 144. As used herein, the term active means an electrically active lead or passageway as opposed to a grounded connection. Active passageways may conduct therapeutic pacing pulses, biological sensing signals or even high-voltage therapeutic shocks. For a neurostimulator application, active passageways may include AC, pulse, triangular or many other different types of waveforms; for example, for a spinal cord stimulator to create paresthesia.

FIG. 5B is taken generally from FIG. 5B-5B from FIG. 5A, which illustrates the quadpolar feedthrough capacitor in cross-section. One can see that there are ground electrode plates 146, which are disposed through the feedthrough capacitor structure and connected to the ground metallization 142. One can also see that each of the four quadpolar passages 134 are associated with its own active electrode plates 148, which are electrically connected through active metallization 144. One can also appreciate that each of the feedthrough holes 134, 144 has its own set of active electrodes 148 that are disposed and overlapping or sandwich-type construction between the ground electrode plates 146. It is the overlapping of the active and ground electrode plates in the dielectric that create the individual feedthrough capacitors. Each of the four feedthrough capacitors are associated with its own passageway metallization 144.

FIG. 6 is an exploded view of the unipolar capacitor previously illustrated in FIGS. 5A and 5B. There are cover sheets 147 and then an active layer showing four active electrodes 148 that are each individually associated with one of the four passageways. As one can see, the ground electrode layer 146 extends in non-conductive relationship with the active passageways to the feedthrough capacitors outside diameter. As before, these are stacked up in interleave relationship to form a quadpolar feedthrough capacitor. It is the overlapping of each one of the pie-shaped active electrode segments 148 over the ground electrode 146 that comprises each one of the capacitor's effective capacitance area (ECA). Referring once again to FIG. 6, one will appreciate that all four of the pie-shaped active electrode segments are of the same size. This means that the resulting feedthrough capacitance for all four of the holes will be equal. It is not necessary that this be the case. For example, some of the pie-shaped segments 148 could be larger than others, such that they could have different capacitance values as well.

Referring back to FIG. 6, one will also appreciate that the effective capacitance area, of say $C_1$ goes up with a number of interleaved layers. For example, shown are two interleaved triangular areas, which doubles the ECA. It will be appreciated that one, two, thirty, one hundred or even hundreds of overlapping areas can be used to greatly increase the ECA or n number.

FIG. 7 is the schematic drawing of the quadpolar feedthrough capacitor ($C_1$, $C_2$, $C_3$, $C_4$) of FIG. 6, but in this case, this is after the feedthrough capacitor has been installed to a hermetic seal ferrule and insulator with pins, as previously described. It is assumed that the feedthrough capacitor outside diameter metallization 142 has been connected directly to either the titanium ferrule 112 or the AIMD housing 116. In both cases, the ferrule and/or the housing would be of titanium and would be subject to oxidation. Accordingly, in the schematic drawing of FIG. 7, one can see that there is an undesirable $R_{oxide}$ shown between each of the feedthrough capacitors 132 and ground 116 (AIMD housing). Referring once again to FIG. 7, one can see that each of the feedthrough capacitors 132 is labeled with terminals 1, 2 and 3. At DC or direct current, there is no difference between terminals 1 and 2 as that is a solid through-pin or leadwire or passageway. However, at RF frequencies, the feedthrough capacitor 132 substantially attenuates frequencies coming from the body fluid side from terminal 1 into the inside of the AIMD housing or device side to terminal 2. As previously stated, these undesirable EMI signals that are entering at terminal 1, are diverted by capacitive reactance through the feedthrough capacitor to ground terminal 3. Referring once again to FIG. 7, the presence of $R_{oxide}$ is very undesirable, as will be explained further throughout this specification.

FIG. 8 illustrates a prior art rectangular feedthrough capacitor 132, which has the same number of poles (that is 4 poles or quadpolar) as previously illustrated in FIG. 5A. Referring once again to FIG. 8, one will see that the quadpolar feedthrough capacitor, in this case, is rectangular. It will be appreciated throughout this invention, that the feedthrough capacitors may be rectangular, square, have rounded corners, comprised an oval or oblong shape, ovular or even elliptical shapes. As previously mentioned, the feedthrough capacitor can be quadpolar, as illustrated, or any other number of feedthrough holes 134. Referring once again to FIG. 8, the ground metallization 142 is brought out to both of the long sides of the feedthrough capacitor 132. This is best understood by referring to FIGS. 11 and 13, which is taken generally from section 13-13 from FIG. 12. This illustrates the ground electrode plates and the fact that they are only exposed along the capacitor's long sides where metallization 142 can be applied. Also shown as FIG. 10, which is taken generally from section 10-10 from FIG. 8, illustrating four active electrodes 148. Each of these active electrodes is associated with one of the active terminal pins 111, 114. The feedthrough capacitor, as illustrated in FIG. 8, is shown ready for installation on top of a hermetic seal subassembly 120 that's illustrated in FIG. 9. Referring to FIG. 9, one can see that there is a metallic ferrule 112, which is typically of titanium and an insulator 160, which is typically of alumina and four pins or leadwires 111, 114. A hermetic and mechanical seal is made between each of the pins 111, 114 and the insulator 160 by gold brazes 162. Also, the rectangular perimeter of the alumina insulator 160 is shown gold brazed 150 to the ferrule 112.

FIG. 12 illustrates the feedthrough capacitor 111 installed to the hermetic seal assembly 120, as previously described in FIGS. 8 and 9. As can be seen, there is an electrical connection material 152, which connects from the capacitor's ground metallization 142 directly to the ferrule 112.

FIG. 13 is taken generally from section 13-13 from FIG. 12. In this section, one can see that there is a gold braze 150 that forms a mechanical and hermetic seal between the insulator 160 and ferrule 112. There is also a hermetic seal gold braze 162 between the insulator 160 and leadwire 111, 114. In this case, the feedthrough capacitor 132 is generally larger in diameter than the gold braze hermetic seal area 150. In this case, one can see the electrical attachment material 152 connecting between the capacitor 132 ground metallization 142 into the ferrule 112. Layer 164 illustrates a highly undesirable oxide layer on the titanium surface of ferrule 112. Oxide layer 164 would appear all over the surfaces of the titanium ferrule 112 but is shown disposed only between the electrical attachment material 152 and the ferrule ½ for simplicity. Referring once again to FIGS. 12 and 13, one can see that the ferrule 112 has an h-flange type shape 163. This is for capturing and subsequent laser welding of AIMD housing halves 116.

FIG. 14 is a schematic diagram illustrating the undesirable presence of $R_{oxide}$ in the ground path of the quadpolar feedthrough capacitor. This $R_{oxide}$ results from the oxide layer 164 previously described in FIG. 13. The presence of $R_{oxide}$ can seriously compromise the proper filtering performance of each one of the quadpolar capacitors. $R_{oxide}$ appears in series with the capacitive reactance. When $R_{oxide}$ becomes significant (on the order of 400 milliohms or higher), this can seriously degrade filtered performance.

FIG. 15 shows the use of novel gold braze bond pads 165 that are one embodiment of a novel feature of U.S. Pat. No. 6,765,779, the contents of which are herein are incorporated fully by this reference. This is best understood by referring to FIG. 16 showing that the feedthrough capacitor 132 ground metallization 142 is electrically attached 152 by a thermal-setting conductive adhesive or a solder or the like directly to this gold bond pad area 165. It is well known that gold is a very noble material and does not oxidize. FIG. 17 is taken from FIG. 22 of the '779 patent. This electrical connection material is labeled 332 in the '779 patent. When sufficiently thick, a layer of gold will effectively block titanium oxides from interfering with the high-frequency electrical connection material 152. This is best understood by referring to FIG. 17, which is taken from section 17-17 from FIG. 16. In the cross-section, one can see the electrical connection material 152 that effects a very low impedance and low resistant electrical connection between the feedthrough capacitor ground metallization 142 and the gold braze pad area 165. During gold brazing, the gold braze pad 165 forms a continuous part of the hermetic seal 150 that effects a mechanical and hermetic joint to the insulator 160. In other words, an essential feature of the '779 patent, is that the low impedance, low resistance ground attach area is continuous with and one of the same width, as the same hermetic seal 150 that forms the hermetic seal gold braze. By electrical attachment 152 to this gold braze 150, one virtually eliminates $R_{oxide}$, as illustrated in schematic FIG. 14.

FIGS. 18 and 19 herein are taken from FIGS. 23 and 24 of the '779 patent. FIG. 18 illustrates that the electrical connection material 152 contacts between, in this case, a round quadpolar capacitor's ground metallization 142 and the gold braze area of the hermetic seal 165. This is best understood by referring to section 19-19 from FIG. 18, which is illustrated in FIG. 19. Referring to FIG. 19, one can clearly see that the electrical connection material 152, which can be of thermal-setting conductive adhesive or a solder or the like, makes a low resistance/impedance (free of titanium oxides) connection between the capacitor ground metallization 142 and at least a substantial portion of the gold braze pad area 165, which also forms the hermetic seal between the ferrule 112 and insulator 160. This forms an oxide-resistant low impedance and low resistance electrical connection that would be robust at high-frequencies so that the feedthrough capacitor 132 can properly divert unwanted high-frequency EMI energy. Referring again to FIG. 19, one will appreciate that the electrical connection material 152 need only contact a significant portion of the gold braze bond pad area 165. In other words, a portion of the electrical connection material is showing also connecting directly to ferrule 112. A portion of the electrical connection material 152 that is attached to the ferrule would be oxidized; however, it only takes a portion of electrical material 152 to contact the oxide-resistant gold 165 to affect a low impedance and low resistance electrical connection. As defined herein, an EMI filter hermetically sealed assembly for an active implantable medical device, will be herein designated as assembly 210. The '779 Patent has enjoyed great commercial success and has proven to be highly reliable. Manufacturing processes of the '779 Patent does require tight dimensional tolerances between the ferrule inside diameter and the alumina insulator outside diameter or perimeter. In addition, the oxide-resistant pads as described in the '779 Patent require a significant amount of extra gold to be used in the process which is thereby increasingly expensive. Referring once again to FIG. 17 (rectangular) and FIG. 19 (discoidal), one will appreciate a serious limitation. While attachment to gold has eliminated the problems associated with $R_{oxide}$, the diameter of the feedthrough capacitor or the length and the width of a rectangular capacitor have both been significantly constrained. For example, referring to FIG. 19, if the diameter of the feedthrough capacitor 132 were increased such that its outside diameter metallization 142 was either aligned with the outermost perimeter of the ferrule or slightly smaller than the outermost perimeter of the ferrule, one could see that there would be no possible way to make the electrical connection 152 to the gold braze pad area 165. Over the past several years, the number of leads required for the feedthrough of an active implanted medical device have constantly increased. This can be best understood in the cardiac space where early pacemakers only paced the right ventricle. Then dual chamber pacing came along with bipolar electrodes in both the right ventricle and the right atrium. Modern devices, also known as cardiac resynchronization devices now have quadpolar leads that are routed through the coronary sinus and are outside the left ventricle. Added to these are defibrillation functions. Accordingly, modern devices have as many as 8, 10 or even 12 leads. A significant market driving force is the need to make these multi-lead devices thin enough and small enough for patient comfort as having too thick of an AIMD housing placed in the pectoral pocket, becomes very uncomfortable for the patient. In summary, the gold bond pads of FIGS. 17 and 19, work very well to eliminate the oxidation problem, but do constrain the geometry such that the resultant devices have relatively low volumetric efficiency.

FIG. 19A illustrates filter performance otherwise known as attenuation or insertion loss curves vs frequency. An ideal attenuation curve is shown for a feedthrough capacitor C, 132. One can see that it has a slight self-resonance (SRF) above 1 GHz and then continues to function. Accordingly, it becomes a broadband 3-terminal filter as previously described. As can be seen, the ideal feedthrough capacitor has over 30 dB of attenuation at all frequencies above 100 MHz. This frequency range is important because that's the range at which cell phones operate and other emitters. Cell phones are of particular concern to active implantable medical devices because they are small and can be brought into very close proximity to a medical implant. For example, one concern is for a pacemaker patient where the cell phone may be placed in a shirt pocket directly over the implant. This would couple maximum energy to implanted leads. Referring once again to the insertion loss attenuation curves of FIG. 19A, one can see what happens when the feedthrough capacitor has undesirable resistive oxide ($R_{oxide}$) in its ground electrical path. The oxide degrades the attenuation or filter performance such that you end up with a curve, which provides less than 30 dB of 'attenuation at frequencies above 100 MHz. This seriously degraded filter performance is of great concern because if a closely held emitter, such as a cellular telephone, interferes with, for example, a pacemaker sense circuit, it can undesirably cause the pacemaker to inhibit. Inhibit means that it would fail to provide life-saving therapeutic pulses. One might ask, why are pacemakers designed to inhibit? Well, there are two reasons: Many patients who suffer from bradycardia (a very low heart rate) are not bradycardic all-day long. In other words, they can come in and out of bradycardic (life-threatening) condition. Therefore, demand pacemakers were developed such that when a patient's normal sinus rhythm returns, the pacemaker will inhibit. This is to not only save battery life, but also prevents a condition called rate competition. This is where you wouldn't want the pacemaker to provide a pulse that is out of sync or competitive with a patient's intrinsic rhythm. However, this does lead to electromagnetic interference danger. If EMI is undesirably detected as a normal cardiac pulse, it can cause the device to inhibit, which is immediately life-threatening for a pacemaker dependent patient.

FIG. 20A illustrates a discoidal capacitor 24 with a counterbore hole 46 that slips over a ferrule 28' and a hermetic seal 30 and was taken from FIG. 2 of U.S. Pat. No. 5,333,095, the contents of which are included herein by reference. The feedthrough capacitor is metallized on its outside diameter and there is an electrical attachment 56 between the feedthrough capacitor metallization and an AIMD housing 22 (116). In this case, there is no electrical connection described between the feedthrough capacitor ground metallization and the ferrule. In fact, the opposite is taught, in that, electrical connection 56 (152) is directly to the AIMD housing structure. It was not known at the time of the '095 invention that serious problems would show up with $R_{oxide}$, as has been previously described.

FIG. 20B is a cross-sectional view taken from FIG. 6 of the '095 patent. It shows its ground electrode plates 42 (146) coming to the outside diameter. There is a metallization (not shown) but labeled as 52 (142). It is this ground metallization that is electrically attached 56 (152) directly to the AIMD housing 22 (116). Referring to FIGS. 20A and 20B, the feedthrough capacitor 142 overhangs the ferrule 28(112), but is not electrically connected to it. The electrical connection 56(152) is between the capacitor outside diameter metallization (142) directly to the AIMD housing 22(116). In addition, the feedthrough capacitor 24(132) of FIGS. 20A and 20B is round and overhangs the ferrule in all directions.

FIG. 20C is taken from FIG. 17 of the '095 patent and illustrates capacitor 224 (132) disposed directly onto an AIMD housing surface 22 (116). As one can see, the ferrule 234 (112) has been previously attached to the AIMD housing 22 (116). In this case, the feedthrough capacitor 224 (132) would be later added and then a ground connection would be made from the outside diameter metallization 224 (132) directly to the AIMD housing 22 (116). In other words, there is no direct connection from the feedthrough capacitor ground metallization to the ferrule at all.

Referring once again to FIG. 20D, there is an even larger problem. There is no way to make in effect, an electrical connection between the ferrule 334 (112) and the outside diameter metallization (142) of the feedthrough capacitor 324 (132). FIG. 13 herein, shows the problem with an effecting electrical connection 152 directly to a titanium ferrule 112. As once can see, there is a highly undesirable oxide layer 164 that is formed on the titanium. This oxide layer is both resistive and also acts as a semi-conductor. The presence of either a resistance or a semi-conductance, severely degrades the EMI filters ability to divert high-frequency RF signals. The importance of capacitor ground attachment to an oxide-resistance ferrule surface is taught in U.S. Pat. No. 6,765,779, the contents of which are incorporated herein fully by reference. FIG. 17 teaches the '779 patent methodology of having the electrical connection material 152 connect from the feedthrough capacitor ground metallization 142 to a gold braze extension of the hermetic seal 150, 165. Again, referring to FIG. 20D, there is no possible way, with a capacitor 324 (132) disposed outside the ferrule, to make a connection to the gold braze area between the ferrule and the insulator. This gold braze area is not shown but is indicated by element 325.

SUMMARY OF THE INVENTION

An embodiment of the present invention is a filter feedthrough configured to be installed in an opening of a housing (116) an active implantable medical device (AIMD 100), the filter feedthrough comprising: a) an electrically conductive ferrule (112) separating a body fluid side opposite a device side, the body fluid side configured to reside outside the AIMD housing and the device side configured to reside inside the AIMD housing, the ferrule including a ferrule opening (306) extending between and to the body fluid side and the device side; b) an insulator (160) hermetically sealing the ferrule opening; c) at least one conductive pathway (111,114,117,185,186) hermetically sealed to and disposed through the insulator between the body fluid side and the device side, the at least one conductive pathway being in non-electrically conductive relation with the ferrule; d) a feedthrough capacitor (132) disposed on the device side; e) wherein at least a first edge (322) of the feedthrough capacitor extends beyond a first outermost edge (302) of the ferrule; and f) wherein at least a second edge (322) of the feedthrough capacitor does not extend beyond a second outermost edge (304) of the ferrule. In regard to part f), in other words, at least a second edge of the feedthrough capacitor is either aligned with or is set back from a second outermost edge of the ferrule.

In other exemplary embodiments, the feedthrough capacitor may comprise: i) at least one active electrode plate disposed parallel and spaced from at least one ground electrode plate, wherein the at least one active and ground electrode plates are disposed within a capacitor dielectric; ii) a capacitor active metallization electrically connected to the at least one active electrode plate and in non-electrically conductive relation with the at least one ground electrode plate; and iii) a capacitor ground metallization electrically connected to the at least one ground electrode plate and in non-electrically conductive relation with the at least one active electrode plate. The capacitor active metallization may be electrically connected to the at least one conductive pathway. The capacitor ground metallization may be electrically connected to the ferrule. The insulator may hermetically seal the ferrule opening by at least one of a first gold braze, a ceramic seal, a glass seal or a glass-ceramic seal. The ferrule may have a rectangular shape, the first outermost edge and the second outermost edge forming at least a part of the rectangular shape. The first outermost edge of the ferrule may be perpendicular to the second outermost edge of the ferrule.

Another embodiment of the present invention is a filter feedthrough configured to be installed in an opening of a housing an active implantable medical device (AIMD), the filter feedthrough comprising: a) an electrically conductive ferrule separating a body fluid side opposite a device side, the body fluid side configured to reside outside the AIMD housing and the device side configured to reside inside the AIMD housing, the ferrule including a ferrule opening extending between and to the body fluid side and the device side; b) an insulator hermetically sealing the ferrule opening by at least one of a first gold braze, a ceramic seal, a glass seal or a glass-ceramic; c) at least one conductive pathway hermetically sealed to and disposed through the insulator between the body fluid side and the device side, the at least one conductive pathway being in non-electrically conductive relation with the ferrule; d) a feedthrough capacitor disposed on the device side, the feedthrough capacitor comprising: i) at least one active electrode plate disposed parallel and spaced from at least one ground electrode plate, wherein the at least one active and ground electrode plates are disposed within a capacitor dielectric; ii) a capacitor active metallization electrically connected to the at least one active electrode plate and in non-electrically conductive relation with the at least one ground electrode plate; and iii) a capacitor ground metallization electrically connected to the at least one ground electrode plate and in non-electrically conductive relation with the at least one active electrode plate; e) wherein the capacitor active metallization is electrically connected to the at least one conductive pathway; f) wherein the capacitor ground metallization is electrically connected to the ferrule; g) wherein at least a first edge of the feedthrough capacitor extends beyond a first outermost edge of the ferrule; h) wherein at least a second edge of the feedthrough capacitor is either aligned with or is set back from a second outermost edge of the ferrule; i) wherein the ferrule has a rectangular shape, the first outermost edge and the second outermost edge forming at least a part of the rectangular shape; and j) wherein the first outermost edge is perpendicularly disposed in relation to the second outermost edge.

Another embodiment of the present invention includes a filter feedthrough that is attachable to an active implantable medical device (AIMD), the filter feedthrough comprising: a) a feedthrough, comprising: i) an electrically conductive ferrule separating a body fluid side opposite a device side, the ferrule comprising a ferrule outermost edge, and a ferrule opening extending to the ferrule body fluid and device sides, wherein, when the ferrule is attached to an opening in a housing of an AIMD, the ferrule body fluid and the ferrule device sides reside outside the AIMD and inside the AIMD, respectively; ii) an insulator at least partially residing in the ferrule opening where the insulator is hermetically sealed to the ferrule; iii) at least one active via hole extending through the insulator; iv) an active conductive pathway residing in and hermetically sealed to the insulator in the at least one active via hole; b) a feedthrough capacitor disposed on the device side of the ferrule, the feedthrough capacitor comprising: i) at least one active electrode plate interleaved in a capacitive relationship with at least one ground electrode plate, wherein the at least one active and ground electrode plates are disposed in a capacitor dielectric; ii) at least one active passageway extending through the capacitor dielectric, the at least one passageway having a capacitor active metallization electrically connected to the at least one active electrode plate; iii) a capacitor ground metallization electrically connected to the at least one ground electrode plate; c) a first electrical connection material electrically connecting the active pathway of the insulator to the active metallization electrically connected to the at least one active electrode plate; and d) a second electrical connection material electrically connecting the capacitor ground metallization electrically connected to the at least one ground electrode plate to the ferrule; e) wherein a first portion of the feedthrough capacitor extends beyond the outermost edge of the ferrule, and a second portion is spaced inwardly from the outermost edge of the ferrule.

Another embodiment of the present invention includes a filter feedthrough that is attachable to an active implantable medical device (AIMD), the filter feedthrough comprising: a) a feedthrough, comprising: i) an electrically conductive ferrule (112) comprising a ferrule sidewall (309) extending to a ferrule body fluid side end (308) surface and to a ferrule device side end surface (310), the ferrule sidewall further comprising a ferrule outermost surface (302,304) and a ferrule inner surface (307) defining a ferrule opening (306) extending to the ferrule body fluid and device side end surfaces, wherein, when the ferrule is attached to an opening in a housing (116) of an AIMD (100), the ferrule body fluid side end surface and the ferrule device side end surface reside outside the AIMD and inside the AIMD, respectively; ii) an insulator (160) at least partially residing in the ferrule opening where the insulator is hermetically sealed to the ferrule, the insulator extending to an insulator body fluid side end surface (312) and to an insulator device side end surface (314); iii) at least one active via hole (316) extending through the insulator to the insulator body fluid and device side end surfaces; and iv) an active conductive pathway (111,114,117,185,186) residing in and hermetically sealed to the insulator in the at least one active via hole; b) a feedthrough capacitor (132) disposed on the device side of the ferrule, the feedthrough capacitor comprising: i) a capacitor dielectric (147) having a capacitor dielectric outer sidewall (322) extending to a capacitor dielectric first end surface (326) and to a capacitor dielectric second end surface (324); ii) at least one active electrode plate (148) interleaved in a capacitive relationship with at least one ground electrode plate (146) in the capacitor dielectric; iii) at least one active passageway (134) extending through the capacitor dielectric to the capacitor dielectric first and second end surfaces; iv) a capacitor active metallization (144) contacting the capacitor dielectric in the at least one active passageway and being electrically connected to the at least one active electrode plate; and v) a capacitor ground metallization (142) electrically connected to the at least one ground electrode plate; and c) a first electrical connection material (156) electrically connecting the active conductive pathway residing in the at least one active via hole in the insulator to the active metallization electrically connected to the at least one active electrode plate of the feedthrough capacitor; and d) a second electrical connection material (152) electrically connecting the capacitor ground metallization electrically connected to the at least one ground electrode plate of the feedthrough capacitor to the ferrule; e) wherein an imaginary projection ($334, FP_{L1}, FP_{L2}$) of the ferrule outermost surface onto the capacitor dielectric second end surface defines: A) at least one capacitor dielectric imaginary first overhang portion (330) extending laterally outwardly beyond the ferrule outermost surface; and B) a capacitor dielectric imaginary second overlay portion (203) that overlays the ferrule device side end surface and overlays the hermetically sealed insulator; C) wherein at least part of the capacitor dielectric outer sidewall in the capacitor dielectric imaginary second overlay portion is spaced inwardly (201) from the ferrule outermost surface, and wherein the at least one ground electrode plate at least partially resides in the capacitor dielectric imaginary second overlay portion.

In other exemplary embodiments, at least a portion of the capacitor ground metallization may contact the capacitor outer sidewall in the capacitor dielectric imaginary second overlay portion and is electrically connected to the ferrule by the second electrical connection material.

The second electrical connection material electrically may connect the capacitor ground metallization electrically connected to the at least one ground electrode plate of the feedthrough capacitor to at least one of the ferrule and a first gold braze hermetically sealing the insulator to the ferrule.

The ferrule device side end surface may be provided with at least one recessed pocket residing adjacent to the outer sidewall of the capacitor dielectric imaginary second overlay portion, the recessed pocket having a gold pocket-pad nested therein and being electrically connected to the ferrule, and the second electrical connection material may electrically connect the capacitor ground metallization electrically connected to the at least one ground electrode plate at least partially residing in the capacitor dielectric imaginary second overlay portion to the gold pocket-pad.

The ferrule outermost surface may comprise opposed ferrule first and second outermost surface portions meeting opposed ferrule third and fourth outermost surface portions; and the capacitor dielectric outer sidewall may comprise opposed capacitor dielectric first and second outer sidewall portions meeting opposed capacitor dielectric third and fourth outer sidewall portions, wherein the imaginary projection of the ferrule outermost surface onto the capacitor dielectric second end surface may provide the ferrule first and second outermost surface portions intersecting the capacitor dielectric third and fourth outer sidewall portions to thereby provide: A) the capacitor dielectric first overhang portion comprising the capacitor dielectric first outer sidewall portion extending laterally outwardly beyond the ferrule first outermost surface portion; B) the capacitor dielectric imaginary second overlay portion overlaying the ferrule device side end surface and the hermetically sealed insulator; and C) a capacitor dielectric third overhang portion comprising the capacitor dielectric second outer sidewall portion extending laterally outwardly beyond the ferrule second outermost surface portion; and wherein the imaginary projections of the ferrule third and fourth outermost surface portions do not intersect the capacitor dielectric third and fourth outer sidewall portions to thereby expose portions of the ferrule device side end surface adjacent to the respective capacitor dielectric third and fourth outer sidewall portions.

The ferrule first and second outermost surface portions may be longer than the ferrule third and fourth outermost surface portions to thereby provide the ferrule having a first rectangular shape in plan-view, and wherein the capacitor dielectric first and second outer sidewall portions may be longer than the capacitor dielectric third and fourth outer sidewall portions to thereby provide the capacitor dielectric having a second rectangular shape in plan-view.

The capacitor ground metallization may contact at least one of the capacitor dielectric third and fourth outer sidewall portions, and wherein the second electrical connection material electrically connects the capacitor ground metallization to the ferrule device side end surface, spaced inwardly from a corresponding one of at least one of the ferrule third and fourth outermost surface portions.

The ferrule device side end surface may be provided with at least one recessed pocket residing adjacent to at least one of the ferrule third and fourth outermost surface portions, the recessed pocket having a gold pocket-pad nested therein and being electrically connected to the ferrule, and wherein the capacitor ground metallization contacts at least one of the capacitor dielectric third and fourth outer sidewall portions with the second electrical connection material electrically connecting the capacitor ground metallization to the gold pocket-pad.

The ferrule outermost surface may comprise opposed ferrule first and second outermost surface portions meeting opposed ferrule third and fourth outermost surface portions, the ferrule first and second outermost surface portions being linear and the ferrule third and fourth outermost surface portions having a radiused shape to thereby provide the ferrule having a first oval shape in plan-view; and the capacitor dielectric outer sidewall may comprise opposed capacitor dielectric first and second outer sidewall portions meeting opposed capacitor dielectric third and fourth outer sidewall portions, the capacitor dielectric first and second outer sidewall portions being linear and the capacitor dielectric third and fourth outer sidewall portions having a radiused shape to thereby provide the capacitor dielectric having a second oval shape in plan-view, wherein the imaginary projection of the ferrule outermost surface onto the capacitor dielectric second end surface may provide the ferrule first and second outermost surface portions intersecting the capacitor dielectric third and fourth outer sidewall portions to thereby provide: A) the capacitor dielectric first overhang portion comprising the capacitor dielectric first outer sidewall portion extending laterally outwardly beyond the ferrule first outermost surface portion; B) the capacitor dielectric imaginary second overlay portion overlaying the ferrule device side end surface and the hermetically sealed insulator; and C) a capacitor dielectric third overhang portion comprising the capacitor dielectric second outer sidewall portion extending laterally outwardly beyond the ferrule second outermost surface portion, and wherein the imaginary projections of the ferrule third and fourth outermost surface portions may not intersect the capacitor dielectric third and fourth outer sidewall portions to thereby expose portions of the ferrule device side end surface adjacent to the respective capacitor dielectric third and fourth outer sidewall portions.

The capacitor ground metallization may contact at least one of the capacitor dielectric third and fourth outer sidewall portions, and wherein the second electrical connection material electrically connects the capacitor ground metallization to the ferrule device side end surface, spaced inwardly from at least one of the ferrule third and fourth outermost surface portions.

The ferrule device side end surface may be provided with at least one recessed pocket residing adjacent to at least one of the ferrule third and fourth outermost surface portions, the recessed pocket having a gold pocket-pad nested therein and being electrically connected to the ferrule, and wherein the capacitor ground metallization contacts at least one of the capacitor dielectric third and fourth outer sidewall portions with the second electrical connection material electrically connecting the capacitor ground metallization to the gold pocket-pad.

The filter feedthrough may further comprise: a) at least one ground passageway extending through the capacitor dielectric to the capacitor dielectric first and second end surfaces, the capacitor ground metallization residing in the ground passageway and being electrically connected to the at least one ground electrode plate; b) a peninsula extending from the ferrule sidewall inwardly into the ferrule opening, wherein the second electrical connection material electrically connects the ground metallization electrically connected to the at least one ground electrode plate of the feedthrough filter to the ferrule peninsula, and c) wherein the ferrule outermost surface comprises opposed ferrule first and second outermost surface portions meeting opposed ferrule third and fourth outermost surface portions; and d) the capacitor dielectric outer sidewall comprises opposed capacitor dielectric first and second outer sidewall portions meeting opposed capacitor dielectric third and fourth outer sidewall portions; e) wherein the imaginary projection of the ferrule outermost surface onto the capacitor dielectric second end surface provides the ferrule first and second outermost surface portions intersecting the capacitor dielectric third and fourth outer sidewall portions to thereby provide the capacitor dielectric first overhang portion comprising the capacitor dielectric first outer sidewall portion extending laterally outwardly beyond the ferrule first outermost surface portion, a capacitor dielectric imaginary second overlay portion overlaying the ferrule device side end surface and the hermetically sealed insulator, and a capacitor dielectric third overhang portion comprising the capacitor dielectric second outer sidewall portion extending laterally outwardly beyond the ferrule second outermost surface portion; and f) wherein the imaginary projections of the ferrule third and fourth outermost surface portions do not intersect the capacitor dielectric third and fourth outer sidewall portions to thereby expose portions of the ferrule device side end surface adjacent to the respective capacitor dielectric third and fourth outer sidewall portions; and g) wherein the capacitor ground metallization also contacts the capacitor dielectric third and fourth outer sidewall portions, and wherein the second electrical connection material also electrically connects the capacitor ground metallization to the ferrule device side end surface, spaced inwardly from the ferrule third and fourth outermost surface portions.

The ferrule first and second outermost surface portions may be longer than the ferrule third and fourth outermost surface portions, and the capacitor dielectric first and second outer sidewall portions are longer than the capacitor dielectric third and fourth outer sidewall portions.

The active conductive pathway in the insulator may comprise a metallic leadwire residing in the at least one active via hole where a gold braze hermetically seals the leadwire to the insulator.

The leadwire may extend to a leadwire body fluid side portion extending outwardly beyond the insulator body fluid side end surface and a leadwire device side portion extending outwardly beyond the insulator device side end surface, the leadwire device side portion residing in the at least one active passageway in the capacitor dielectric where the leadwire is electrically connected to the at least one active electrode plate of the feedthrough capacitor.

The at least one active via hole in the insulator may be defined by an active via hole inner surface extending along a longitudinal axis to the insulator body fluid and device side end surfaces, and wherein the active conductive pathway residing in the at least one active via hole comprises: a) a layer of a ceramic reinforced metal composite (CRMC) comprising a mixture of alumina and platinum that contacts the active via hole inner surface, the layer of CRMC extending from a CRMC first end residing at or adjacent to the insulator device side end surface to a CRMC second end residing at or adjacent to the insulator body fluid side end surface, wherein an inner surface of the CRMC is spaced toward the longitudinal axis with respect to the via hole inner surface; and b) a substantially pure platinum material that contacts the CRMC inner surface, the substantially pure platinum material extending from a substantially pure platinum material first end residing at or adjacent to the insulator device side end surface to a substantially pure platinum material second end residing at or adjacent to the insulator body fluid side end surface.

The CRMC first and second ends and the substantially pure platinum material first and second ends may extend to the respective insulator body fluid and device side end surfaces.

At least one of the CRMC first and second ends may be recessed inwardly into the active via hole from the respective insulator body fluid and device side end surfaces, and wherein the substantially pure platinum material may extend to the insulator body fluid and device side end surfaces.

At least one of the CRMC first and second ends may be recessed inwardly into the active via hole in the insulator from the respective insulator body fluid and device side end surfaces, and wherein a corresponding at least one of the substantially pure platinum material first and second end may be recessed inwardly into the active via hole from the respective insulator body fluid and device side end surfaces, and wherein a metallic end cap may extend from the at least one recessed CRMC first and second end and the correspondingly recessed substantially pure platinum material first and second end to the corresponding insulator body fluid and device side end surface.

The metallic end cap may comprise platinum. The substantially pure platinum material is a platinum wire. The platinum wire may be exposed at the insulator device side end surface. The platinum wire may extend through the substantially pure platinum material to the insulator body fluid and device side end surfaces, the platinum wire being spaced from the layer of CRMC contacting the active via hole inner surface in the insulator.

BRIEF DESCRIPTION OF THE DRAWINGS

The accompanying drawings illustrate the invention. In such drawings.

DETAILED DESCRIPTION OF THE PREFERRED EMBODIMENTS

In some of the following figure descriptions herein, reference axes are included to be helpful in understanding the present invention (see for example FIG. 21). In particular these are orthogonal axes with an x, y and z axis shown in the figures to provide a reference for the reviewer for increased understanding of the present invention. As used herein, the z axis may also be referred to as the longitudinal axis. In cross-sections the axes will appear as either z, y or z, x axes views, which is consistent with isometric geometry.

Figure 21A:
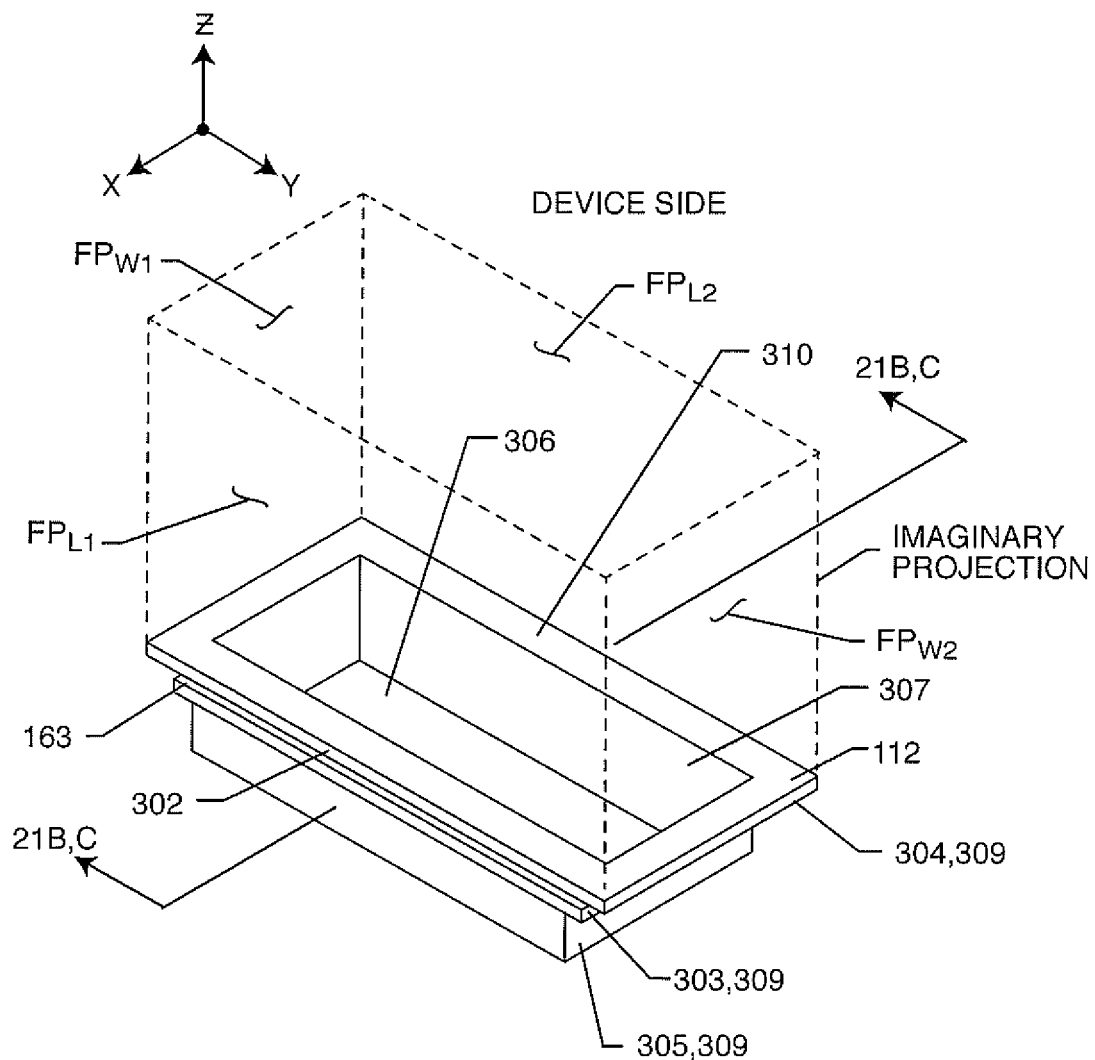
FIG. 21A is an isometric view of just a ferrule that can be used with the present invention.

FIG. 21A illustrates a rectangular ferrule structure 112 for an AIMD that is typically made of titanium. As shown herein, the ferrule is without an insulator 160 and without leadwires 111. There are four imaginary planes, as illustrated, extending upward above the ferrule 112. These imaginary planes extend from the outermost perimeter edge of the ferrule and embody in the y-z axis, ferrule plane $FP_{L1}$ and $FP_{L2}$. There are also two planes extending in the x-z plane and these are the ferrule with planes $FP_{W1}$ and $FP_{W2}$.

Figure 21B:
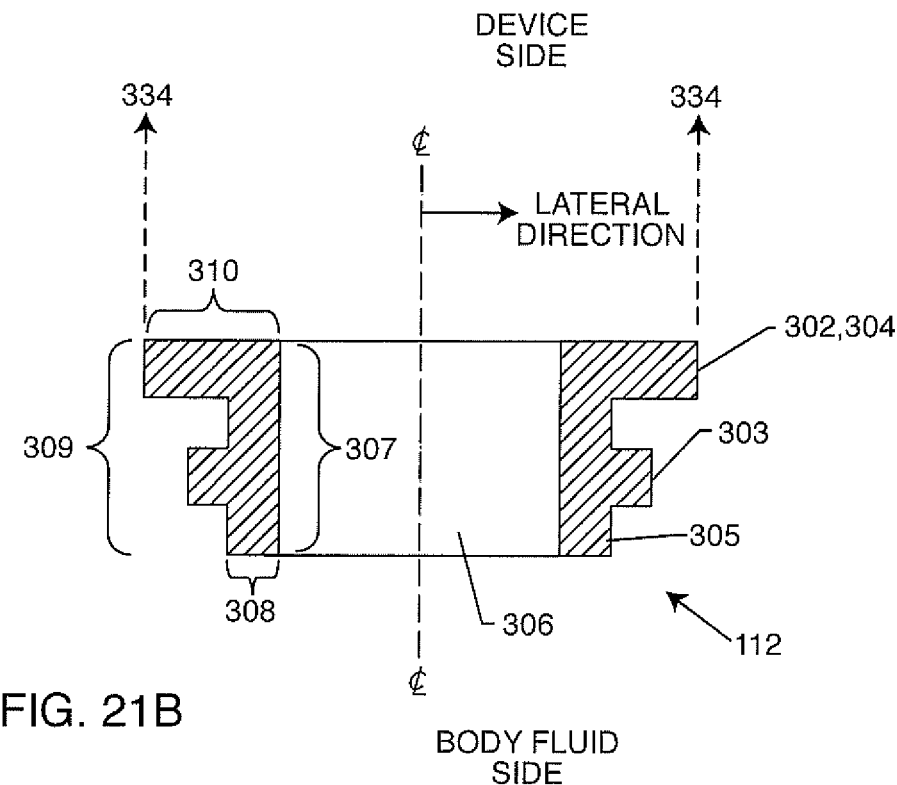
FIG. 21B is a sectional view of one embodiment of a ferrule taken along lines 21B-21B from FIG. 21A.
Figure 21C:
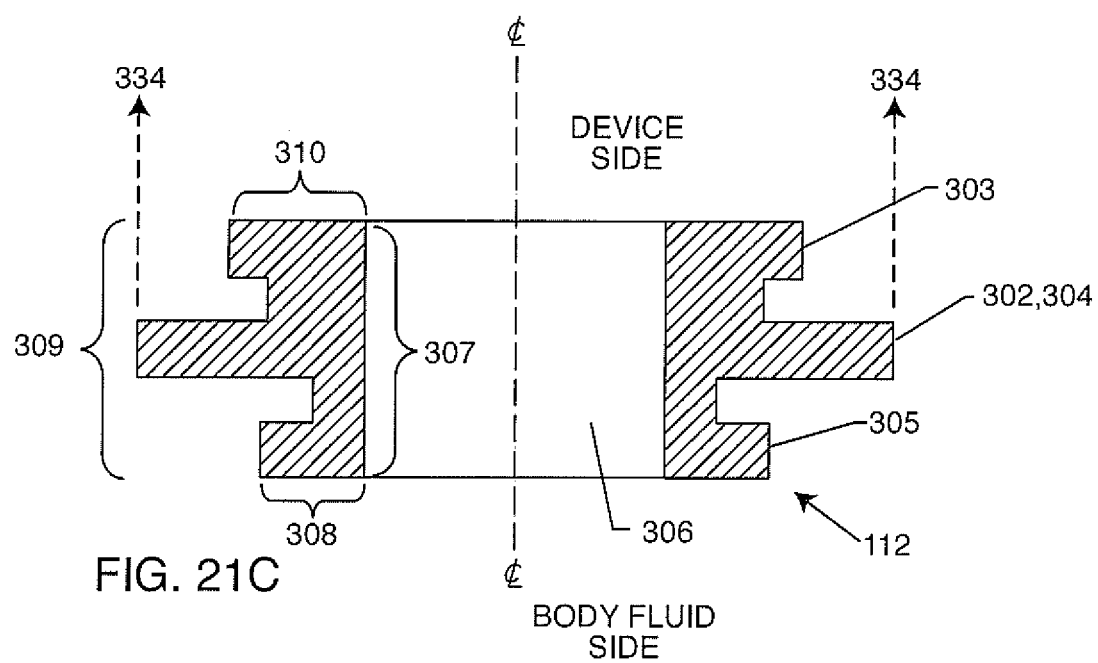
FIG. 21C is a sectional view of another embodiment of the ferrule taken along lines 21C-21C from FIG. 21A.
Figure 21D:
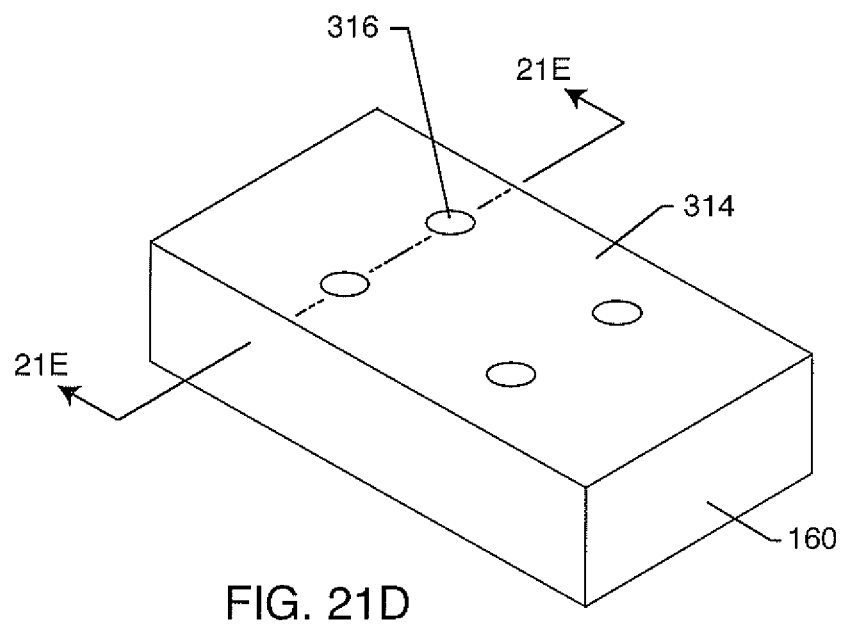
FIG. 21D is an isometric view of just an insulator that can be used with the present invention.
Figure 21E:
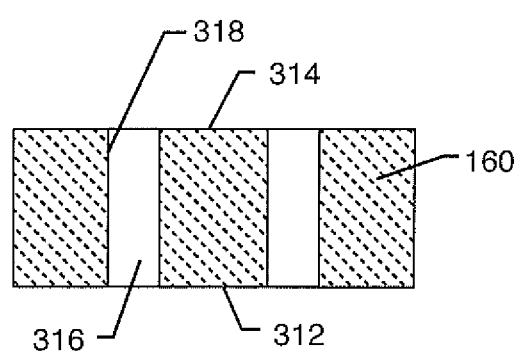
FIG. 21E is a sectional view taken along lines 21E-21E of FIG. 21D.
Figure 21F:
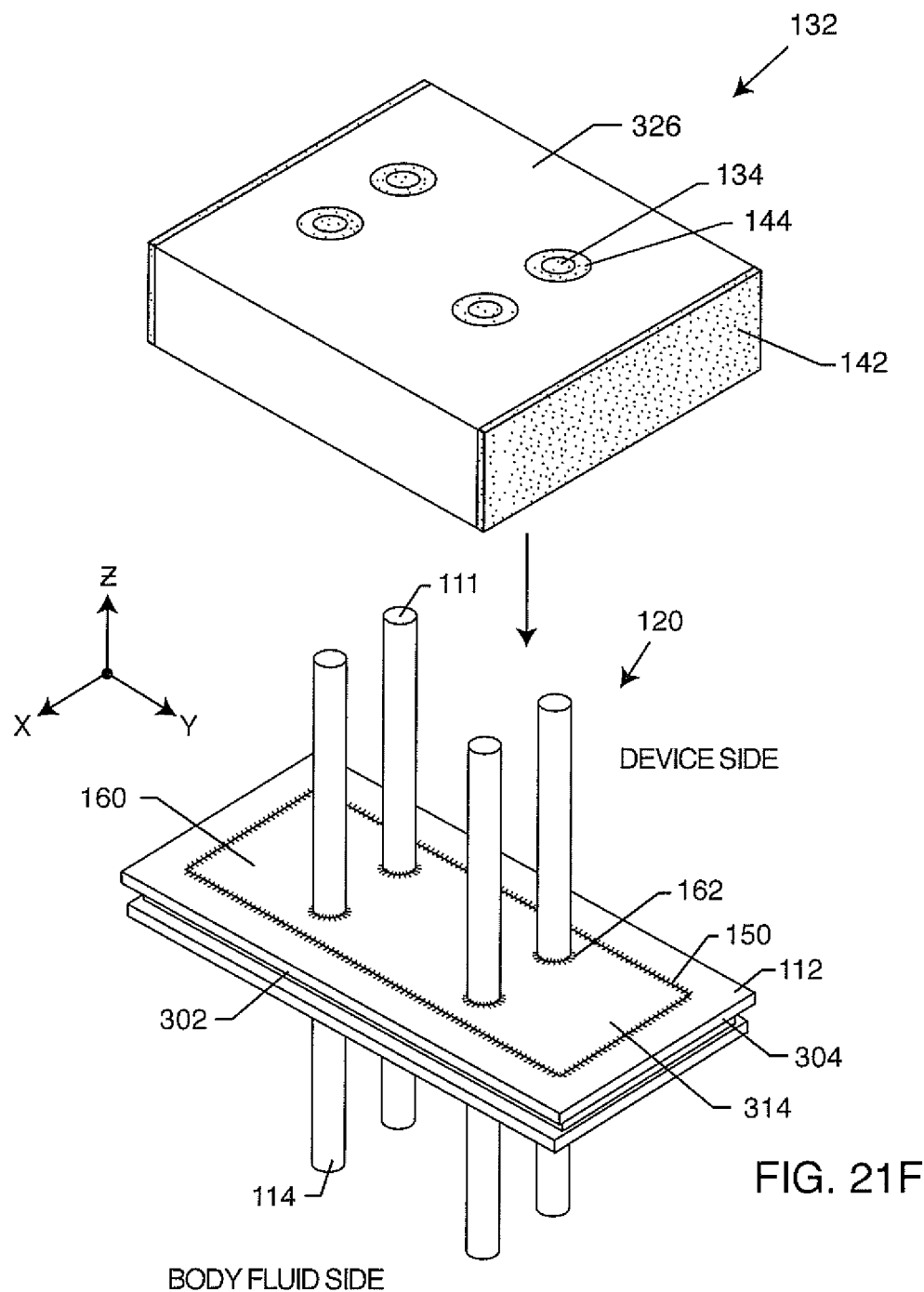
FIG. 21F is an isometric exploded view of a feedthrough before the present invention capacitor is attached.

Jumping ahead to FIG. 21F, one can see that an insulator 160 of FIG. 21D is configured to be installed in the ferrule opening 306. The insulator has four passageways that are also known as insulator via holes 316. As shown, the insulator has a device side end surface 314 which is opposite the insulator body fluid side end surface 312.

FIG. 21B illustrates a modified ferrule 112, as previously depicted in FIG. 21A. There is a center line CL shown, with an arrow indicating the lateral direction. As can be seen, the lateral direction is perpendicular to the axis of the center line CL. A ferrule inner surface 307 is defined as shown. In this embodiment the inner surface 307 is relatively simply in shape, but it is understood by those skilled in the art that it could comprise numerous surfaces. A ferrule outermost surface 302, 304 is also indicated. It is understood that in one direction the outermost surface may be indicated as 302 and in a perpendicular direction the outermost surface may be indicated as 304. Referring again to the ferrule outermost surfaces 302, 304, one can see that ferrules often have complex shapes, including, in this case, surfaces 303 and 305. For the purposes of the present invention, that which will be the outermost, meaning the surface of the ferrule that extends in the lateral direction furthest from the center line, is defined as the ferrule outermost surface 302, 304. Accordingly, the surfaces 303 and 305 are not the outermost. A ferrule device side end surface 310 is also defined as shown. The ferrule side wall 309 is defined as including all of the projections and irregularities of the ferrule side wall which would include, in this case, the outermost surface 302, 304 and other features, such as 303 and 305. In other words, the ferrule side wall 309 comprises the entire side wall and all of its features whether outermost or not. The ferrule also has a body fluid side end surface 308, as shown. The ferrule also comprises a ferrule opening 306, as shown. As is understood by those skilled in the art, the ferrule opening 306 is configured to receive an insulator structure 160. Referring once again to FIG. 21B, one will see that there is an imaginary projection 334 shown projected (perpendicular to surface 310) aligned with the ferrule outermost surface 302, 304. This imaginary projection 334 is helpful in later figures to understand how a feedthrough capacitor will be disposed in an overhanging relationship to the ferrule.

FIG. 21C is very similar to FIG. 21B but illustrates that ferrules 112 can take on various shapes. In this case, the ferrule outermost surface 302, 304 is not necessarily disposed contiguous with the ferrule device side end surface. Rather, the ferrule outermost surface 302, 304 is between surfaces 303 and 305. Yet, the imaginary ferrule projection 334 is from the ferrule outermost surface 302, 304, no matter where it occurs along the ferrule side wall 309. It is also understood by those skilled in the art that ferrules are typically made of titanium and are always electrically conductive. However, other suitable materials for a ferrule are possible as this teaching is not limited to just a titanium ferrule.

302 is defined herein as a first outermost surface but which can also be called a first outermost edge. Likewise, 304 is defined as a second outermost surface but which can also be called as a first outermost edge. It is noted that the surfaces/edges 302 and 304 are perpendicular to each other in the case of a rectangular shaped ferrule.

FIG. 21D shows an alumina ceramic insulator 160 that has been configured such that it will fit into the ferrule opening 306, as previously described in FIGS. 21A, 21B and 21C. In this particular case, the insulator has four passageways 316. Referring now to cross-sectional view 21E-21E taken from FIG. 21D, one can see these passageways are active passageways meaning that they are going to receive terminal pins that pass from a body fluid side to a device side of the AIMD. Again, referring to FIG. 21E, there is an active hole inner surface 318, as shown. The insulator body fluid side end surface 312 is indicated and the insulator device side end surface 314 is also indicated. In general, when the insulator is installed in a ferrule 112 and the ferrule is installed in an AIMD housing 116, the device end surface 314 will be the side that is directed toward the inside of the AIMD housing and the insulator body fluid side end surface 312 will be that side that is directed towards the body fluid side of the AIMD.

FIG. 21F illustrates a rectangular quadpolar hermetic feedthrough 120. One can see that there is a ferrule structure 112 that has been gold brazed 150 to a generally alumina ceramic insulator 160. (The alumina ceramic insulator 160 was previously described in FIGS. 21D and 21E.) There are also four leadwires (i.e. pins or leads) 111, 114 which are also gold brazed 162 to the alumina insulator 160. It will be noted that the through-pins, which are solid conductors, are labeled 111 on the device side and 114 on the body fluid side. Accordingly, even those these leadwires are solid, they can be described as having a device side portion 111 and a body fluid side portion 114. As used and defined herein, the word "portion" does not mean that a structure, such as a leadwire, has to have two different parts. Rather, it rather means that it has two different ends. However, as shown in later figures the leadwire itself may be made from differing materials to save cost.

Figure 1:
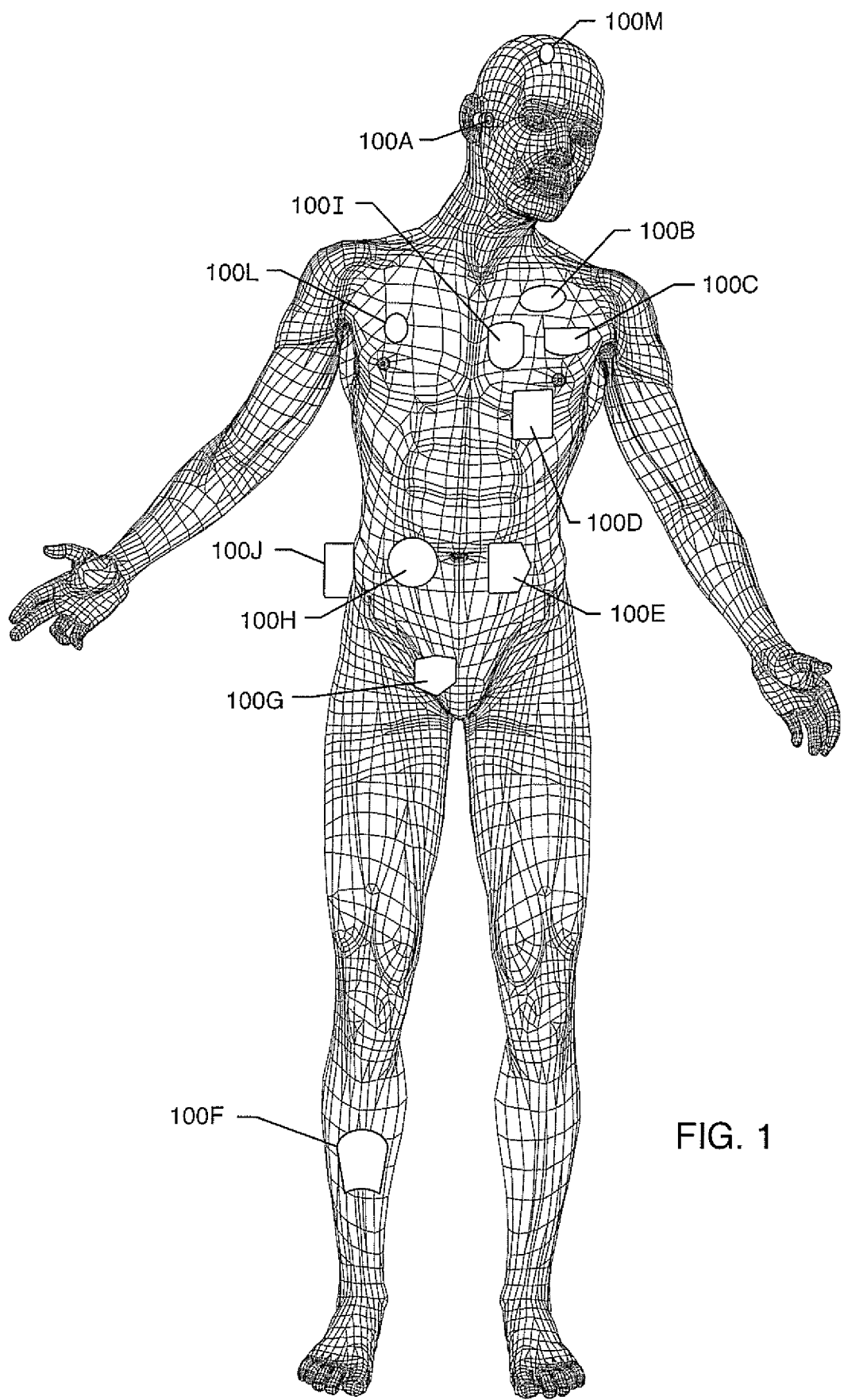
FIG. 1 is a wire-formed diagram of a generic human body showing a number of exemplary implantable medical devices.
Figure 2:
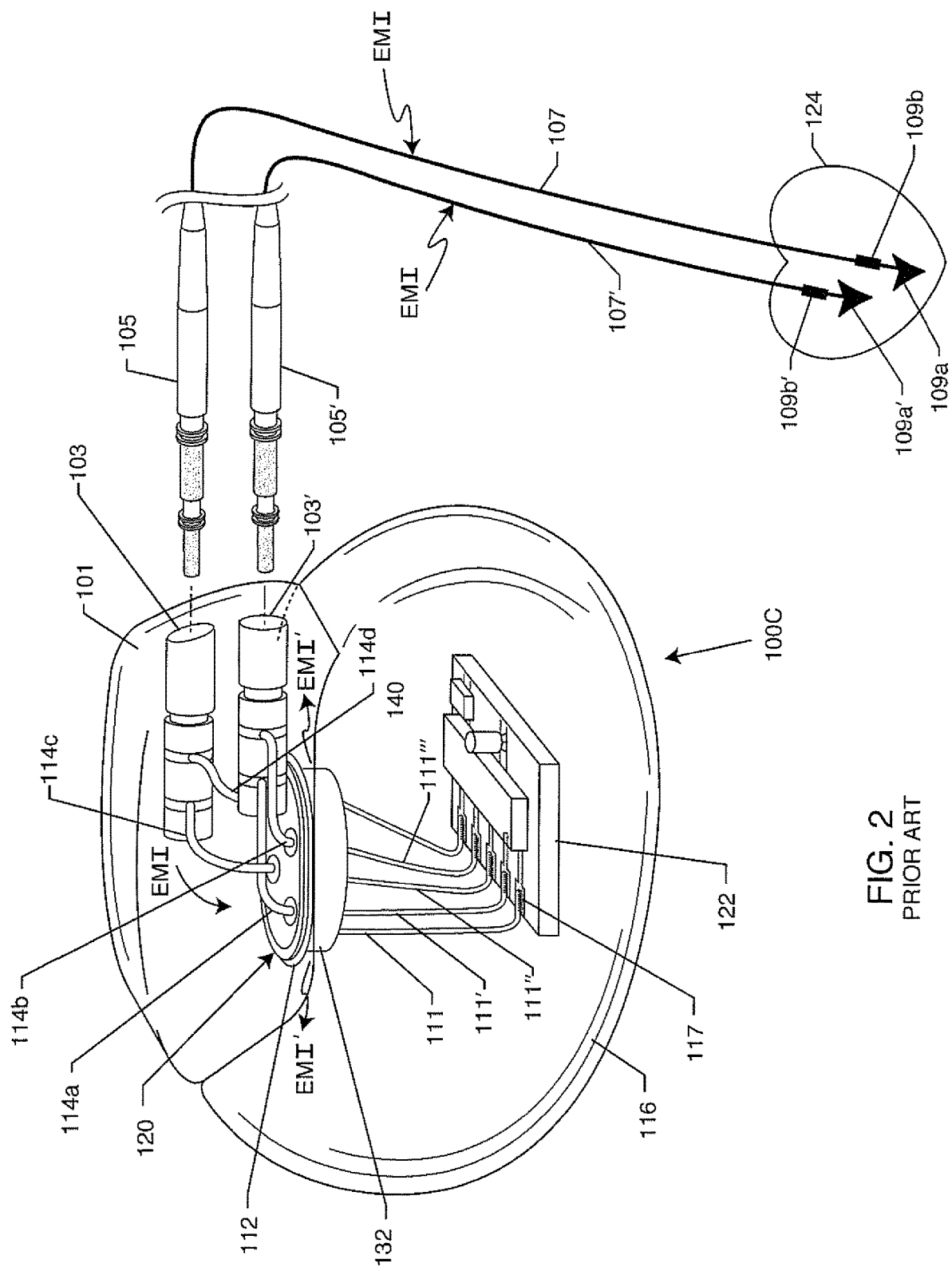
FIG. 2 is a side view of a prior art cardiac pacemaker.
Figure 2A:
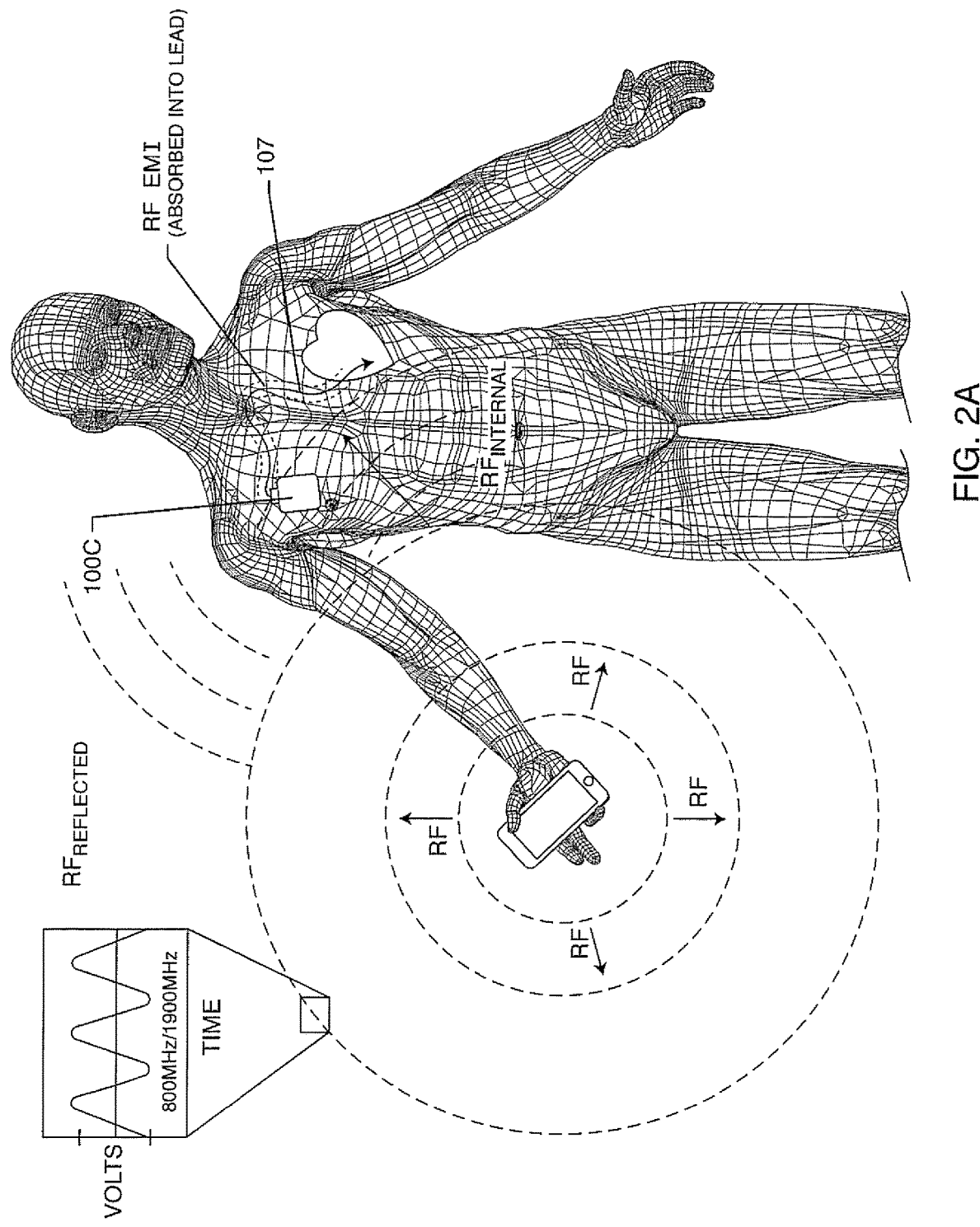
FIG. 2A is a wire-formed diagram illustrating how RF fields are absorbed into a lead of an implantable medical device.
Figure 3:
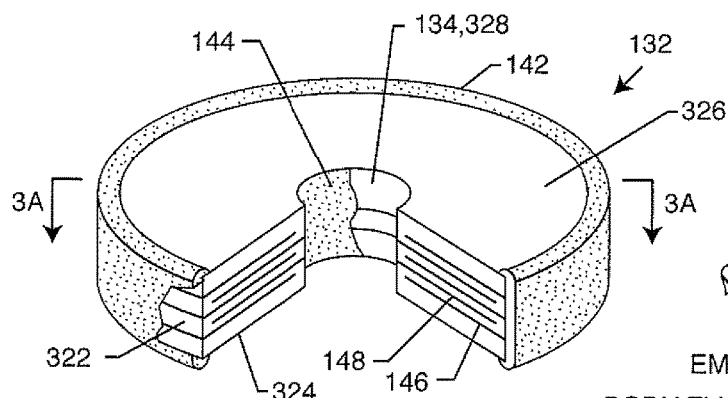
FIG. 3 is an isometric cut-away view of a prior art unipolar feedthrough capacitor.
Figure 3A:
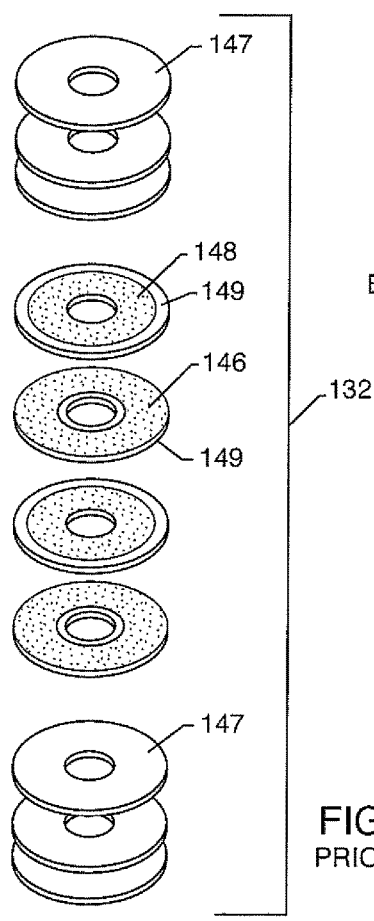
FIG. 3A is an exploded isometric view of the unipolar capacitor of FIG. 3.
Figure 4:
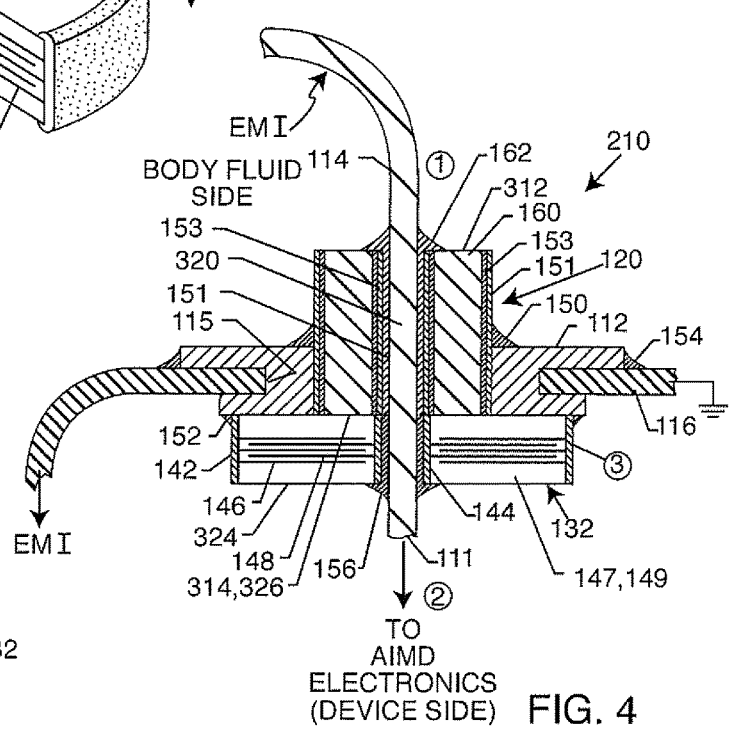
FIG. 4 is a sectional view of a prior art hermetic feedthrough terminal.
Figure 4A:
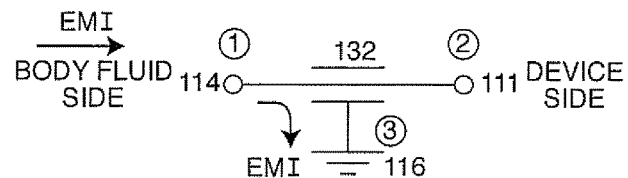
FIG. 4A is an electrical schematic of the structure of FIG. 4.
Figure 5A:
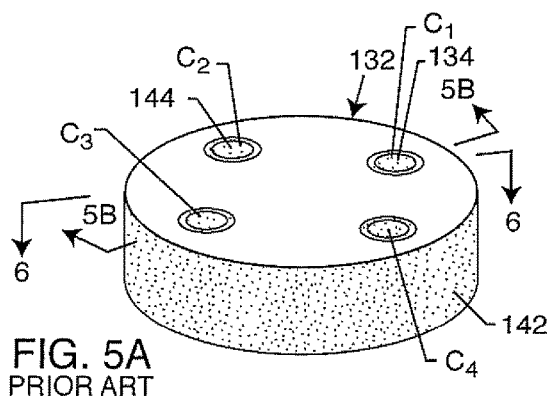
FIG. 5A illustrates a quadpolar feedthrough capacitor.
Figure 5B:
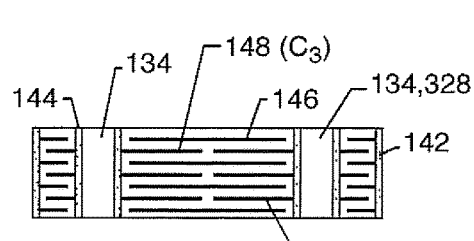
FIG. 5B is a sectional view taken generally from FIG. 5B-5B from FIG. 5A, which illustrates the quadpolar feedthrough capacitor of FIG. 5A.
Figure 6:
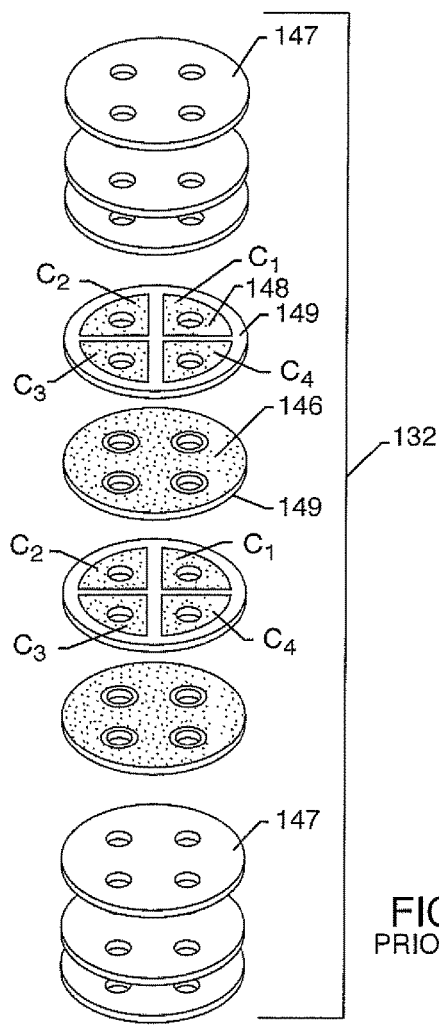
FIG. 6 is an exploded isometric view of the unipolar capacitor previously illustrated in FIGS. 5A and 5B.
Figure 7:
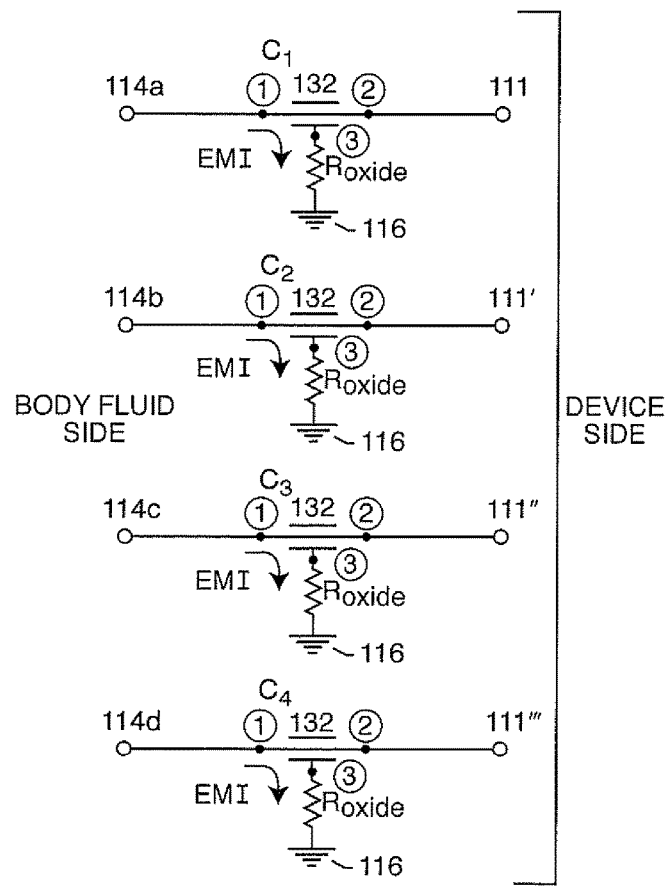
FIG. 7 is the schematic drawing of the feedthrough capacitor of FIGS. 5A-5B.
Figure 8:
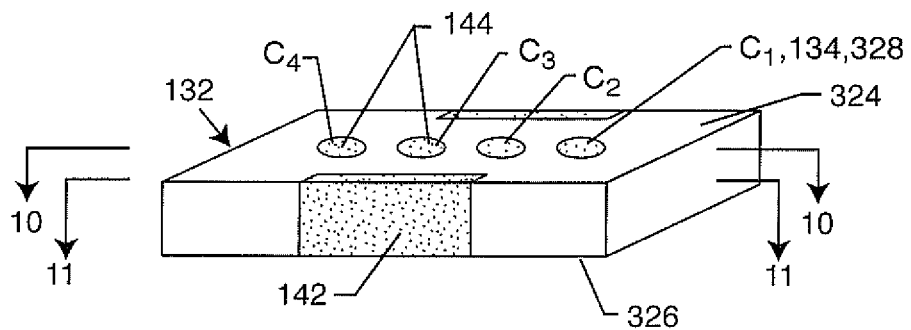
FIG. 8 illustrates a prior art rectangular feedthrough capacitor, which has the same number of poles (4, quadpolar) as previously illustrated in FIG. 4A.
Figure 13:
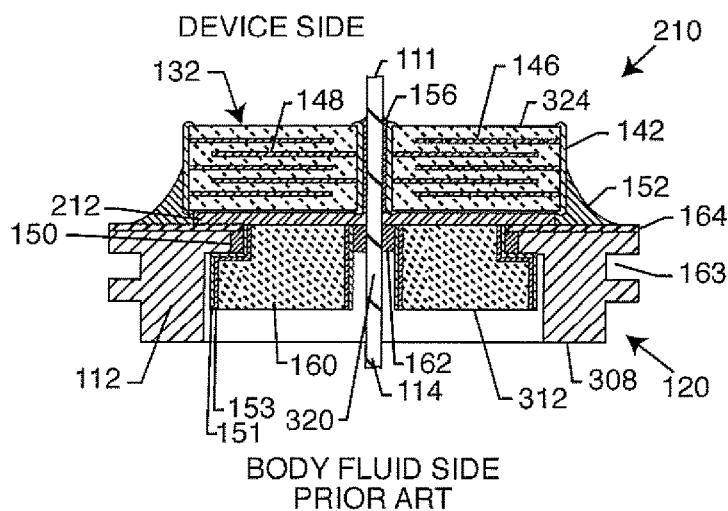
FIG. 13 is a sectional view taken generally from section 13-13 from FIG. 12.
Figure 14:
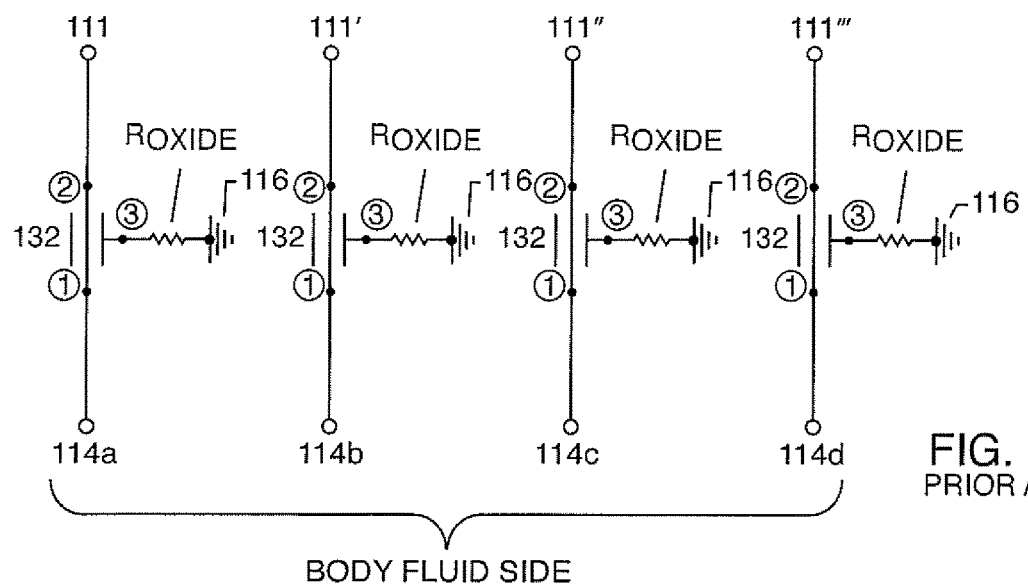
FIG. 14 is an electrical schematic diagram illustrating the undesirable presence of an oxide in the ground path of the quadpolar feedthrough capacitor.
Figure 15:
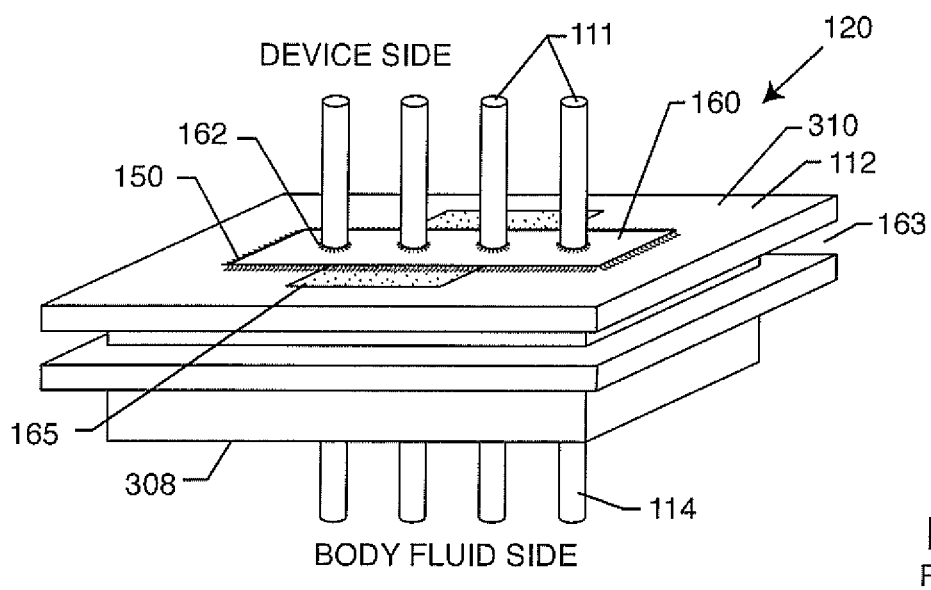
FIG. 15 shows the use of novel gold braze bond pads that are one embodiment of a novel feature of the '596 patent.
Figure 16:
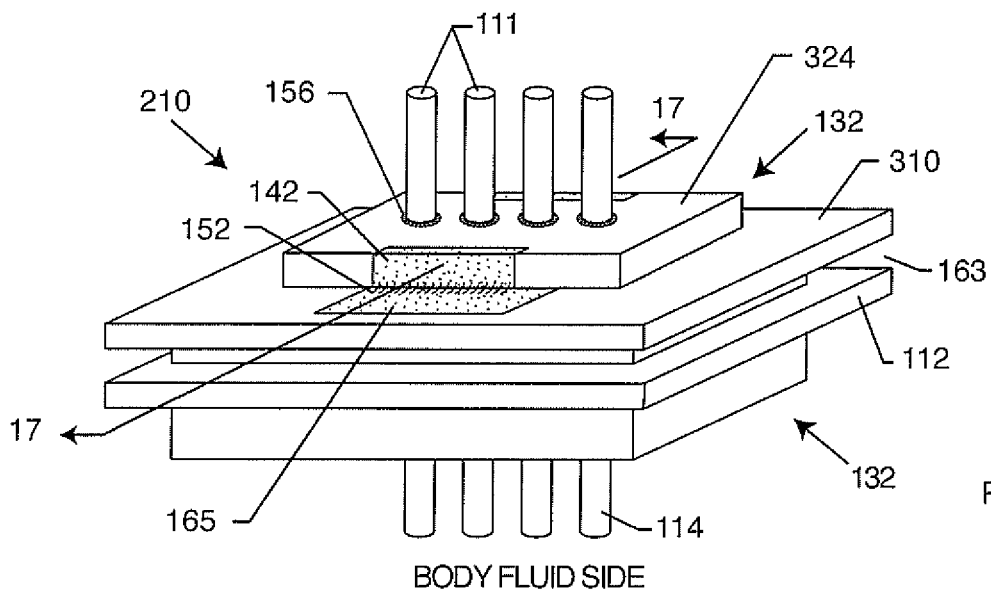
FIG. 16 shows that the feedthrough capacitor ground metallization is electrically attached by a thermal-setting conductive adhesive directly to the gold bond pad area.
Figure 17:
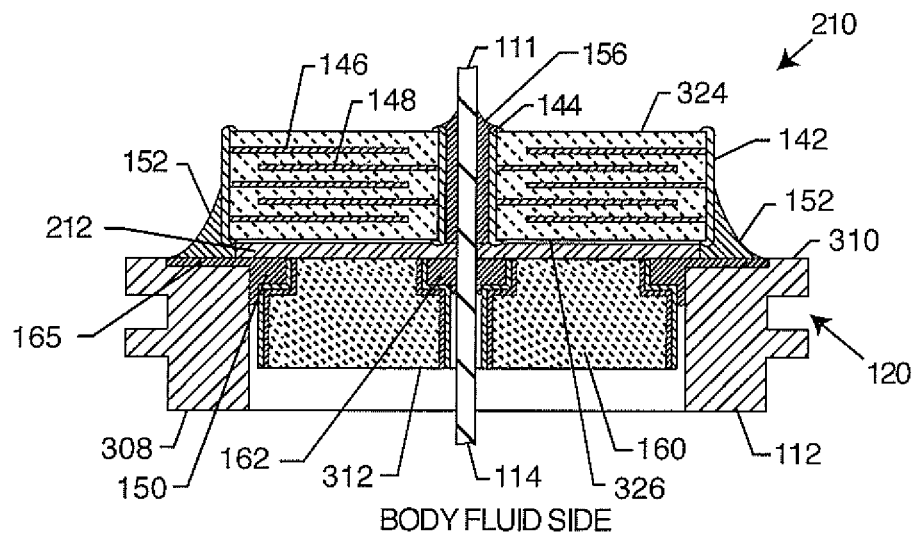
FIG. 17 is a sectional view taken from section 17-17 from FIG. 16.
Figure 18:
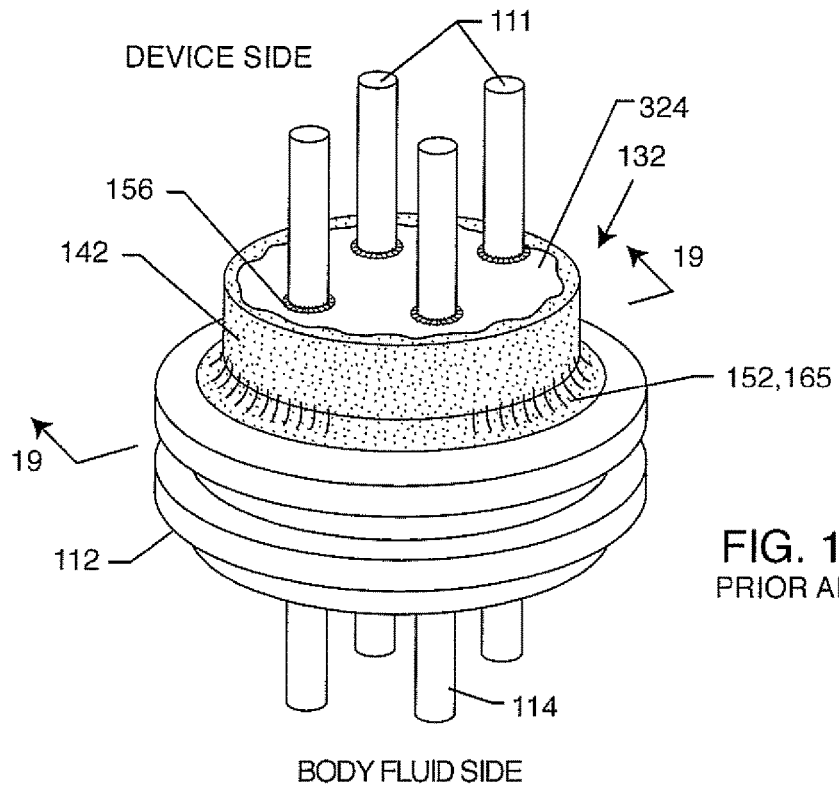
FIG. 18 is an isometric view taken from FIG. 23 of the 779 patent.
Figure 19:
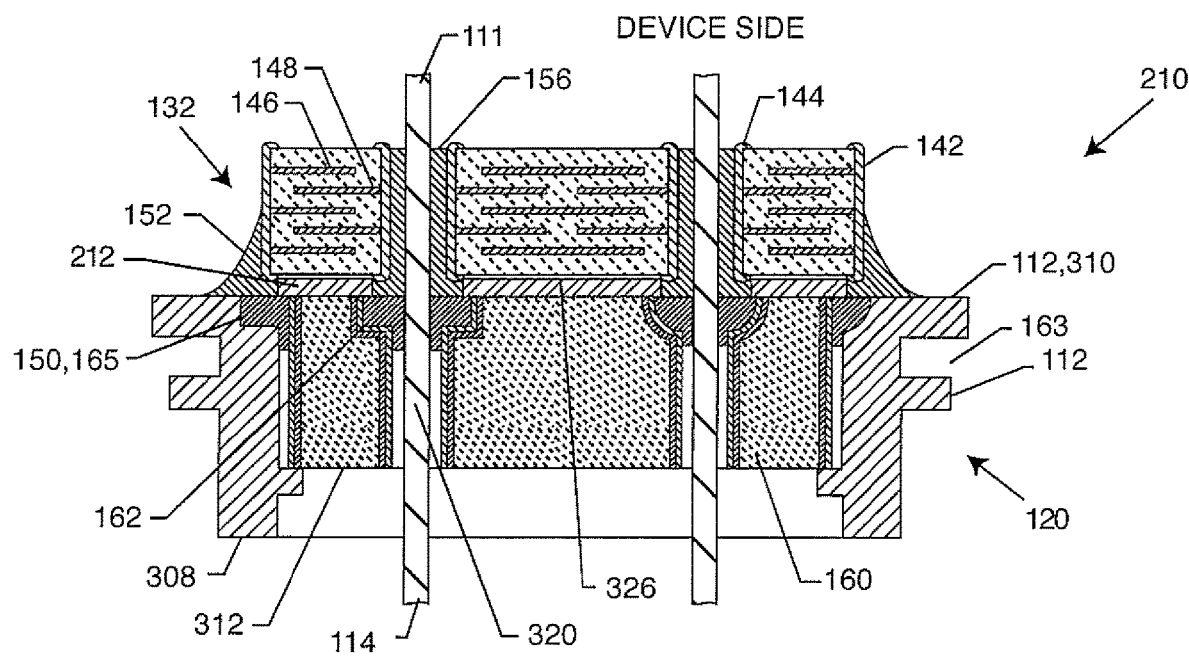
FIG. 19 is a sectional view of the structure of FIG. 18 taken along lines 19-19.
Figure 19A:
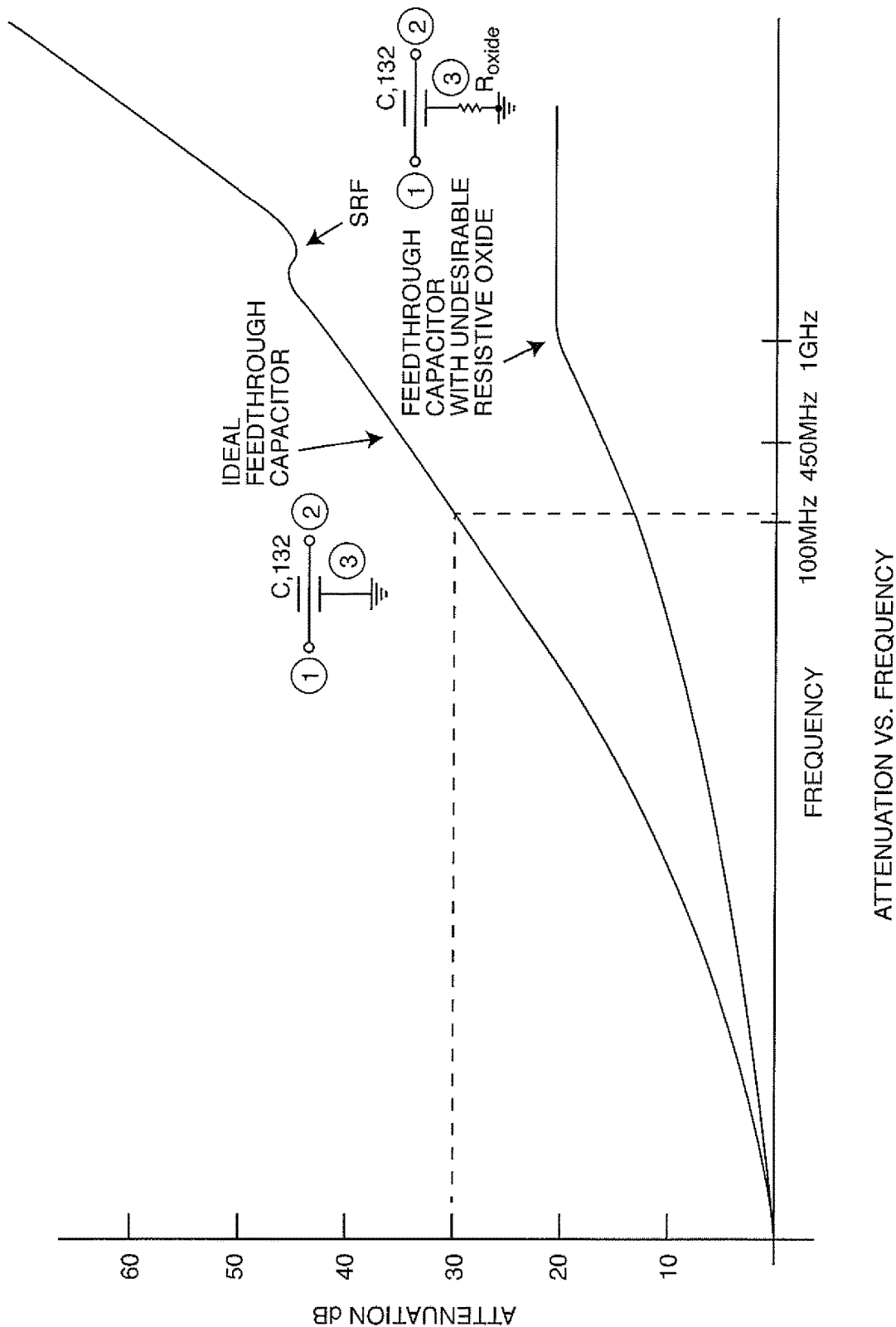
FIG. 19A illustrates filter performance otherwise known as attenuation or insertion loss curves versus frequency.
Figure 20A:
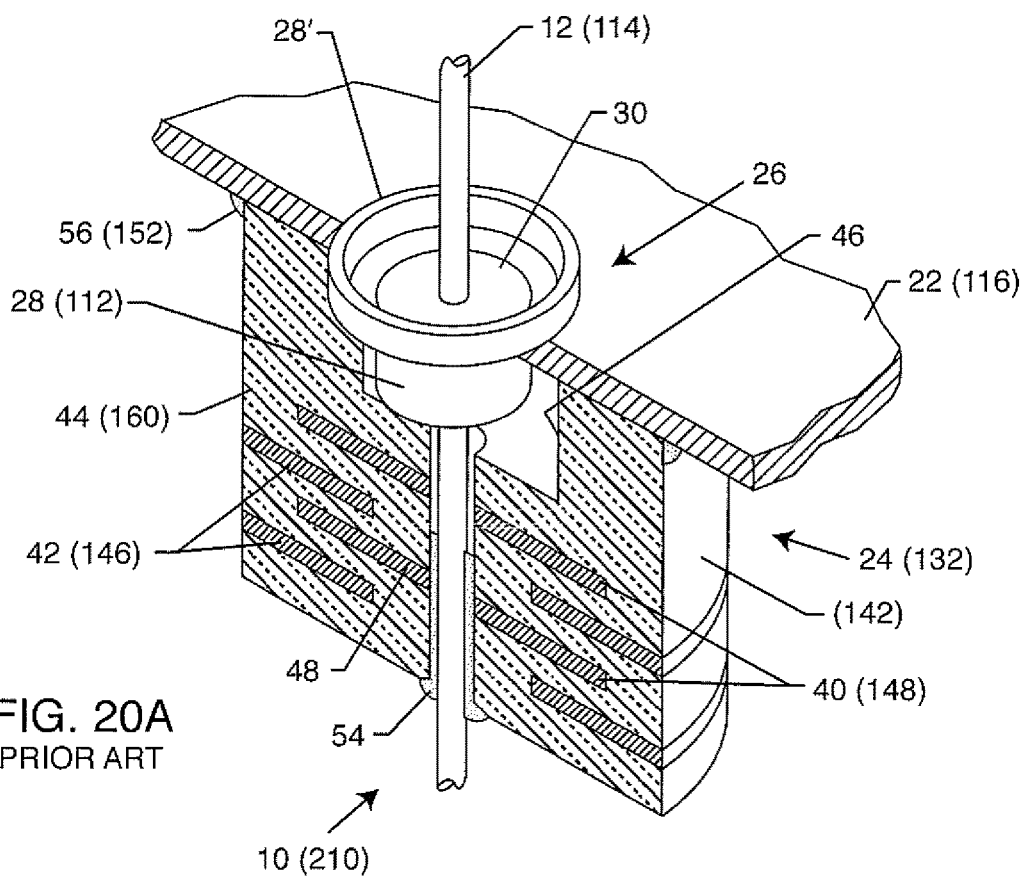
FIG. 20A illustrates sectional isometric view of a prior art feedthrough.
Figure 20B:
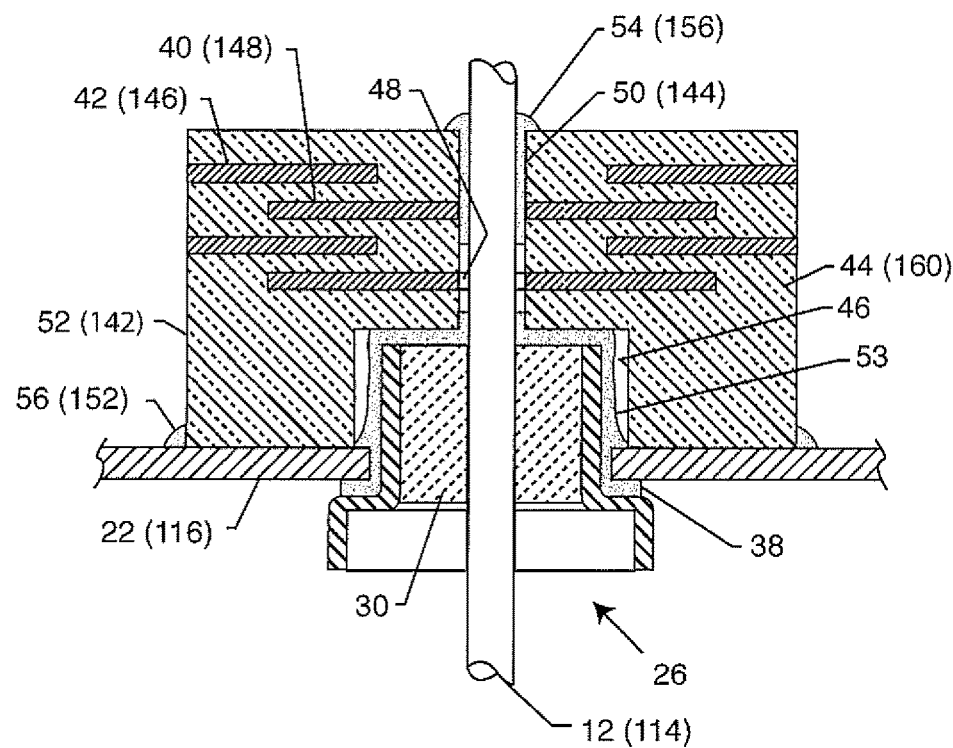
FIG. 20B is a sectional view of a prior art feedthrough.
Figure 20C:
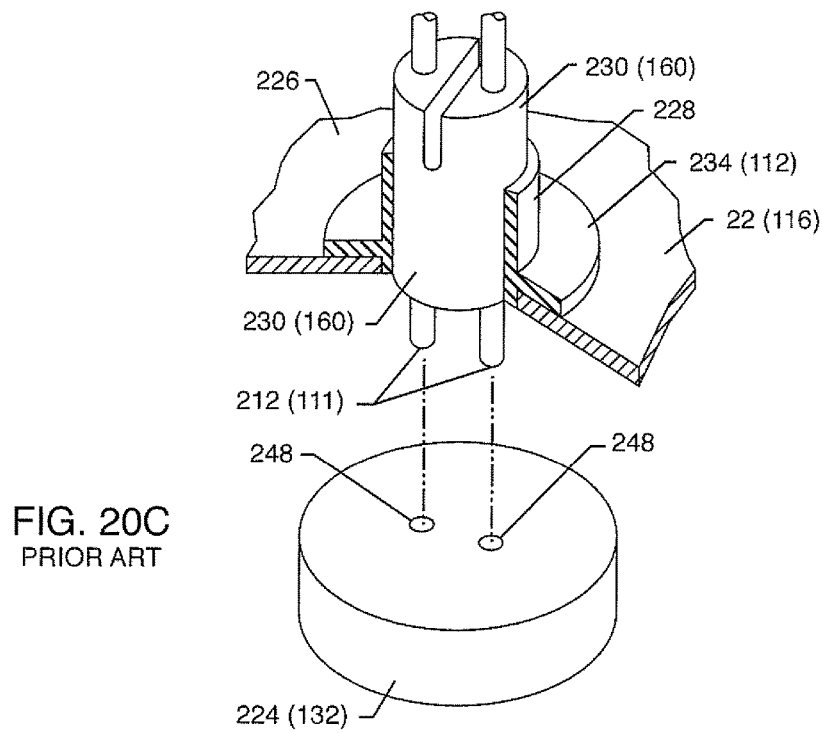
FIG. 20C is an exploded sectional view of a prior art feedthrough.
Figure 20D:
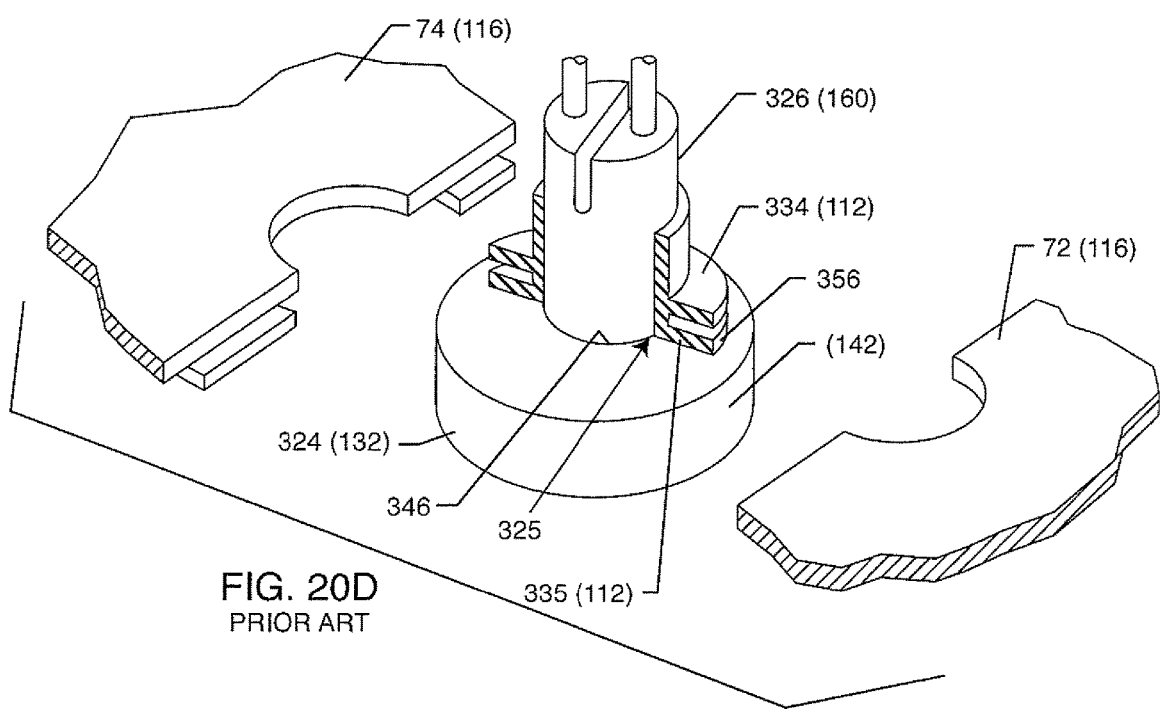
FIG. 20D is an exploded sectional view of a prior art feedthrough.

FIG. 21F also illustrates the feedthrough capacitor 132 coming down and being mounted "adjacent" the ferrule 112, such that the feedthrough capacitor can be directly mounted onto one of the ferrule and/or the insulator, as previously illustrated in FIG. 4 or it can be spaced away from one of the insulator and the ferrule with an insulative washer 212, as previously illustrated in FIG. 13. The feedthrough capacitor 132 could even be spaced away from either the insulator or the ferrule by an air gap. As used herein, the word "adjacent" is not limited to touching, rather "adjacent" includes being right near and/or mounted directly onto a structure, being spaced from with an air gap or also spaced with a washer there between.

Referring once again to FIG. 21F, the leadwires 111, 114 are also defined herein as comprising active conductive pathways that reside in and are hermetically sealed to the insulator 160, in the at least one active insulator via hole 316, as previously described in FIG. 21D. Skipping ahead to FIGS. 39-45, the insulator structure 160 may comprise a ceramic reinforced co-sintered metal 185 with platinum co-sintered end caps 186. The active conductive pathway residing in and hermetically sealed to the insulator need not always comprise a leadwire as shown in FIG. 21F, but can comprise any of the structure, as defined in any of the drawings herein.

Figure 22:
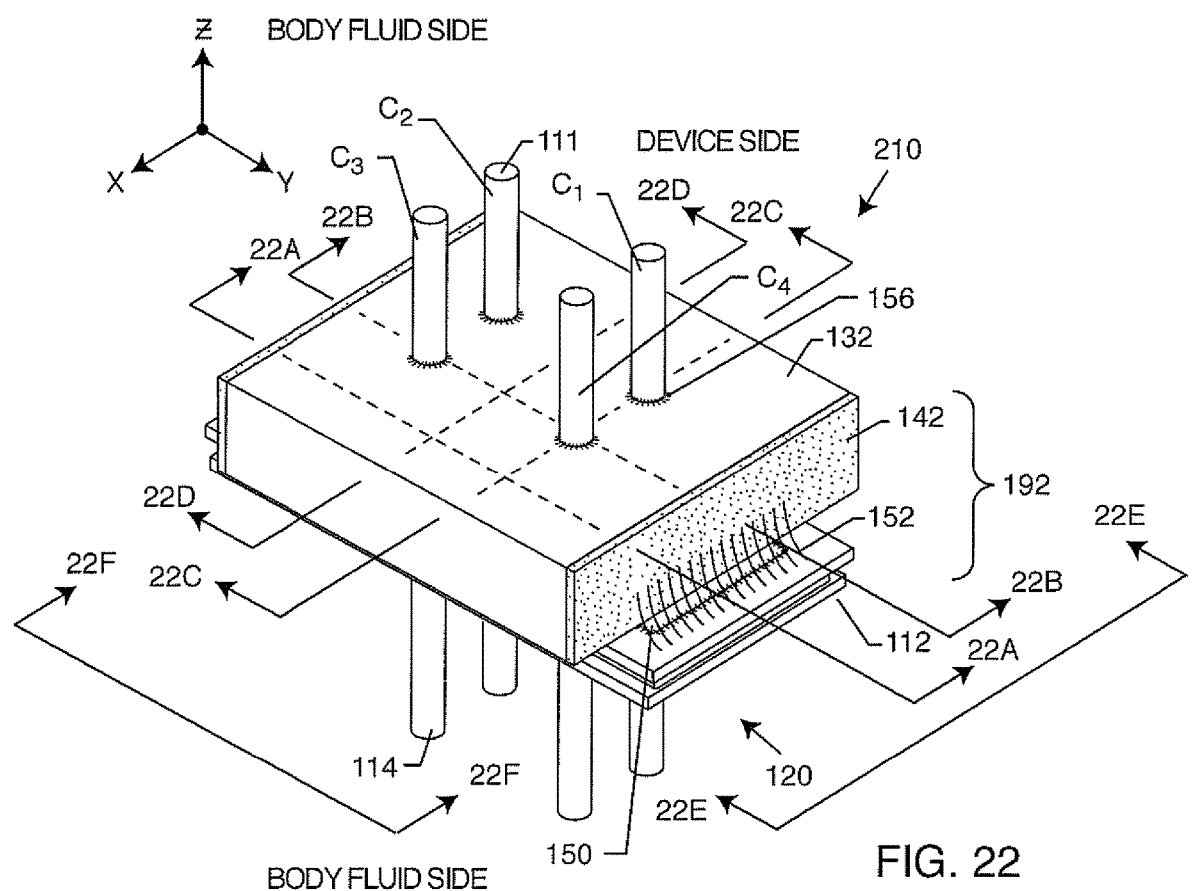
FIG. 22 is an isometric view of the present invention where the capacitor overhangs the ferrule edge on two edges for an increased effective capacitance area.

FIG. 22 illustrates a rectangular (or could be square, circular, rounded, oval or some combination thereof) feedthrough capacitor 132 mounted to the hermetic terminal feedthrough assembly 120 of FIG. 21. The feedthrough capacitor 132 has a unique geometry and for the first time, overhangs both sides of the ferrule in the x direction. However, in this embodiment the feedthrough capacitor is designed to not overhang the ferrule in the y direction. In fact, the y dimension of the feedthrough capacitor is specifically designed such that the electrical connection material 152 between the capacitor ground metallization 142 and the ferrule will hit the oxide-resistant exposed gold braze 150, as illustrated.

Referring once again to FIG. 22, a global ground electrical connection 192 is defined. As defined herein, a ground electrical connection 192, as illustrated in FIG. 22, may comprise a ground electrode plate set electrically connected to the capacitor ground metallization 142. Then, either a thermal-setting conductive adhesive, or a solder or the like 152 is used to electrically connect the capacitor ground metallization 142 to the ferrule 112. As previously discussed, ferrule structures 112 are typically of titanium and may be oxidized. Accordingly, in the present invention, the global electrical connection 192 would include connection to the hermetic seal of the gold braze 150, as illustrated, which is an oxide-resistant and bio-stable surface. Alternatively, the global electrical connection may be to gold pockets in the ferrule, as will be described in FIGS. 23 and 23A herein. The global electrical connection 192 may also comprise one or more internally grounded feedthrough passageways that will be described in detail herein, in FIGS. 26 and 26A.

Figure 28:
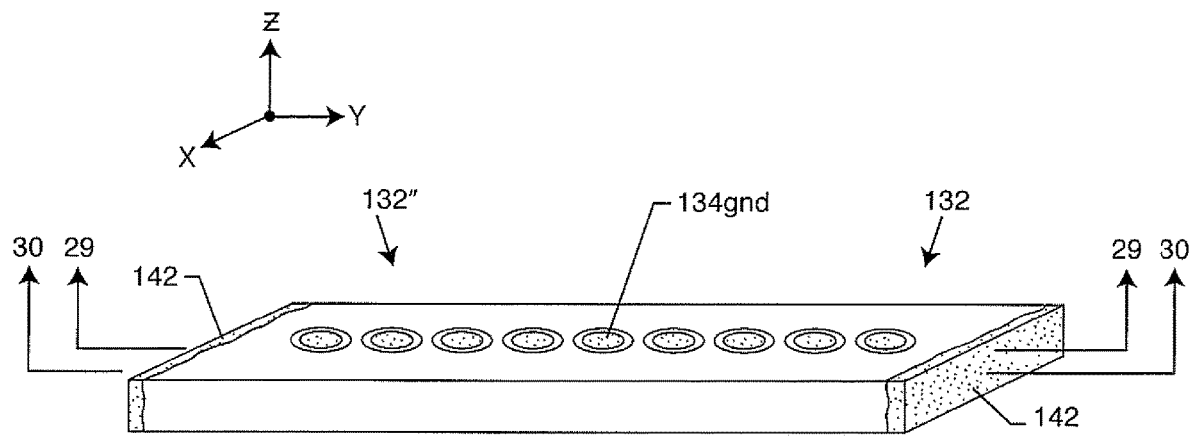
FIG. 28 illustrates an isometric view of a hybrid feedthrough capacitor of the present invention.
Figure 31:
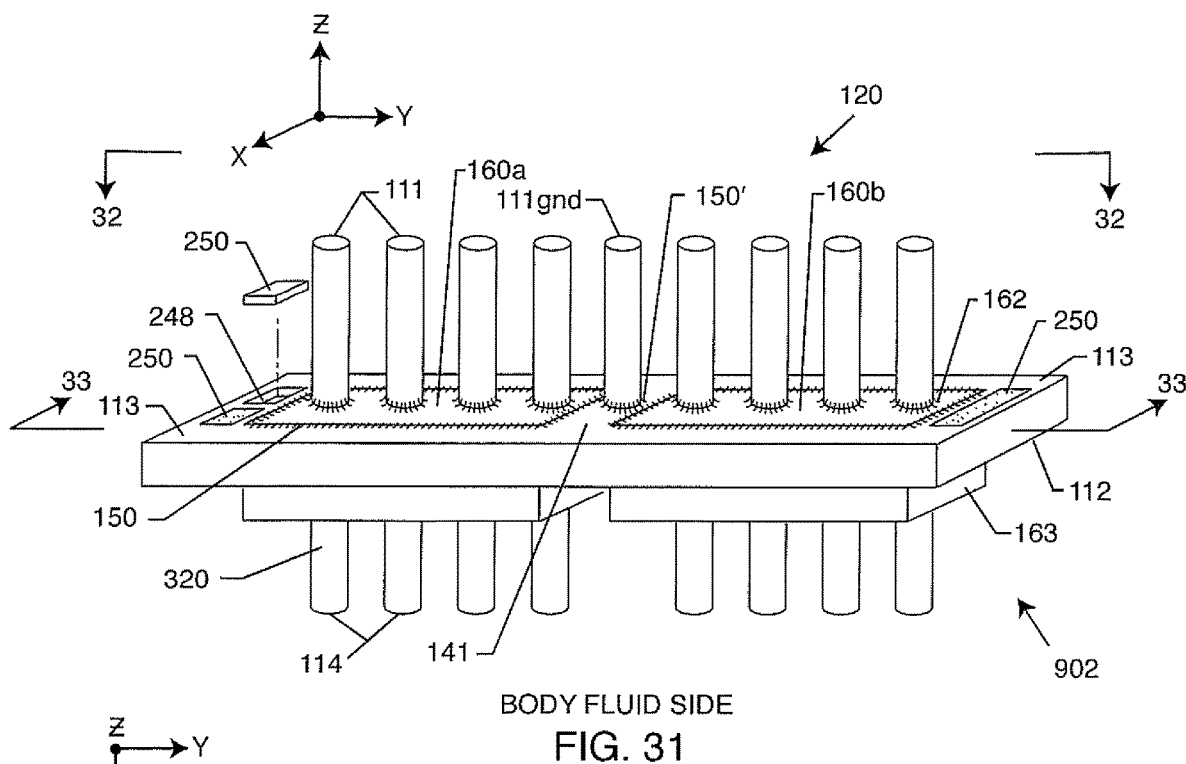
FIG. 31 illustrates an isometric view of a feedthrough assembly having a bridge for an internal ground attachment and a gold pocket pad for an external ground attachment to use with the capacitor of the present invention.
Figure 32:
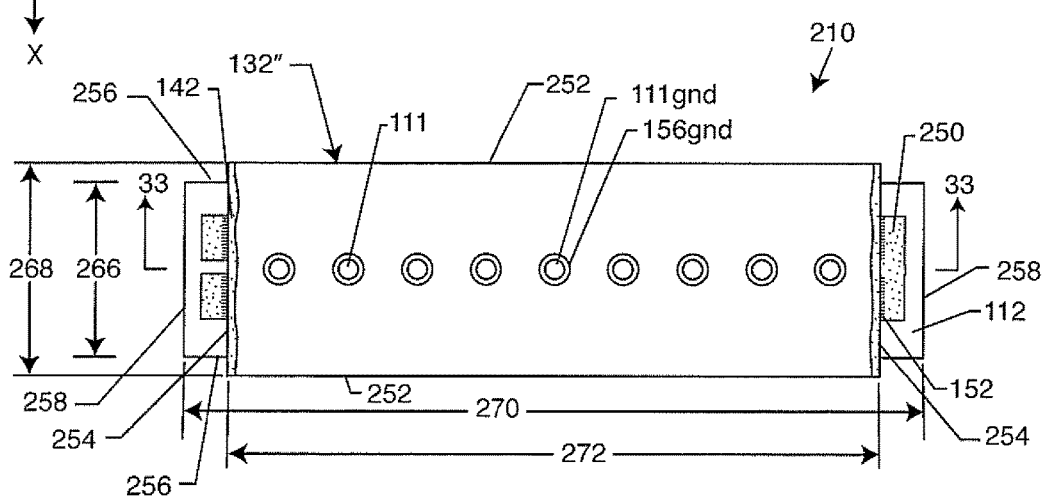
FIG. 32 is a top view of the structure of FIG. 32 taken along lines 32-32.

Again, the global use of the ground electrical connection or electrically conductive path 192 may include a hybrid grounded capacitor, as illustrated in FIG. 28, and is shown attached to a ferrule in FIGS. 31 and 32. This embodiment is known as a hybrid ground in that, one of the feedthrough capacitor passageways is grounded. In other words, attached electrically connected to the ground electrode plates and the ground electrode plates are also brought out to external metallizations. This hybrid grounding system globally is still called 192, but combines exterior electrical metallizations, as well as a grounded passageway.

The novel configuration as illustrated in FIG. 22 illustrates several important principles: 1) an oxide-resistant metal connection 152 is made between the ground metallization 142 of the feedthrough capacitor to the gold braze 150; and 2) in the x direction, the feedthrough capacitor is actually wider than the ferrule, which greatly increases the effective capacitance area (ECA) of each one of the four filter capacitors. The present invention results in an amazing increase of volumetric efficiency for the device.

Referring once again to FIG. 22, it is not really practical to reverse the geometry, that is, make the capacitor relatively thin in the x axis and overhanging the long in the y axis. The problem with this reversal is that the ECA of each of the four capacitors would be significantly reduced. It will be appreciated that this could be done under the present invention but would not be a preferred embodiment.

A recent driving factor behind having a capacitor overhang in one axis (in this case, the x axis) and not overhang in the y axis has to do with the need for a oxide-resistant ground electrical connection 192 while at the same time, increasing the capacitor's ECA. As previously mentioned, with the number of leads constantly increasing, there is a constant need for improvements in volumetric efficiency, which increased ECA provides. Increasing the ECA also enables the use of lower k dielectrics, such as those taught by U.S. Pat. Nos. 9,764,129; and 10,092,749, the contents of which are included in full herein by reference.

Figure 22A:
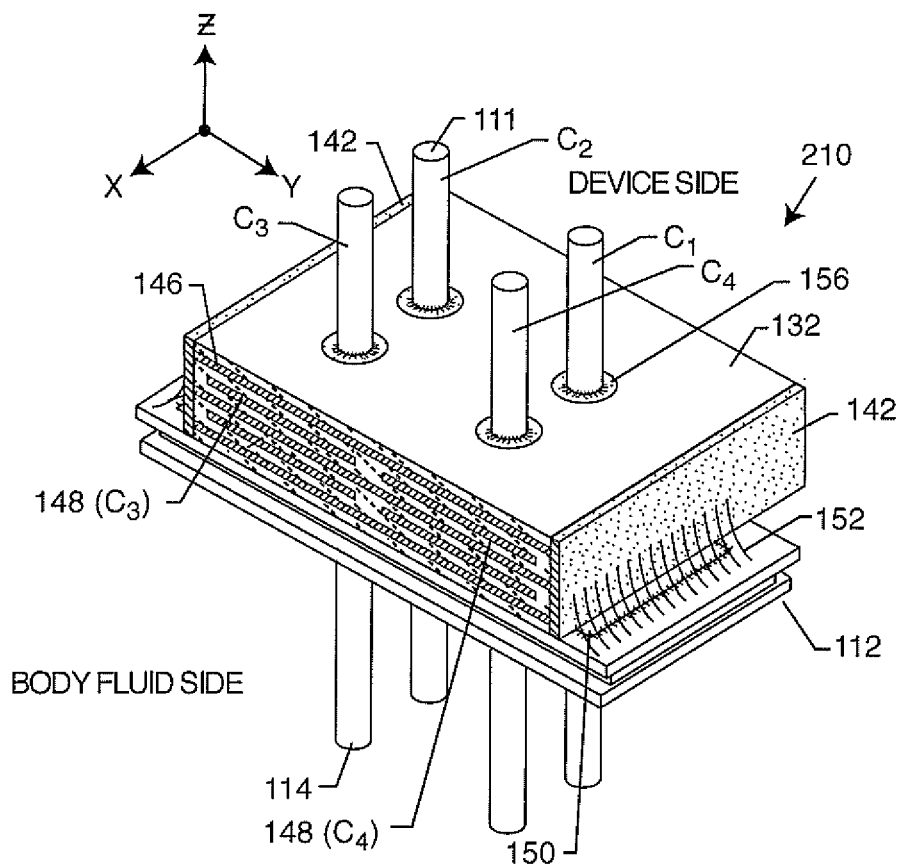
FIG. 22A is a sectional isometric view taken along lines 22A-22A from FIG. 22.

FIG. 22A is taken generally from section 22A-22A from FIG. 22. FIG. 22A is sliced through the capacitor exactly along the perimeter edge (y-z plane) of the ferrule. This is why the ferrule is not shown cross-sectioned in FIG. 22A. The internal electrode plates of the feedthrough capacitor 132 have been exposed, such that one can see the active electrodes 148 and the ground electrodes 146, which run from one end of the capacitor to the other in the y direction and are connected to an external capacitor metallization 142. One can also clearly see the electrical connection 152 between the capacitor ground metallization 142 and the gold braze of the hermetic seal.

Figure 22B:
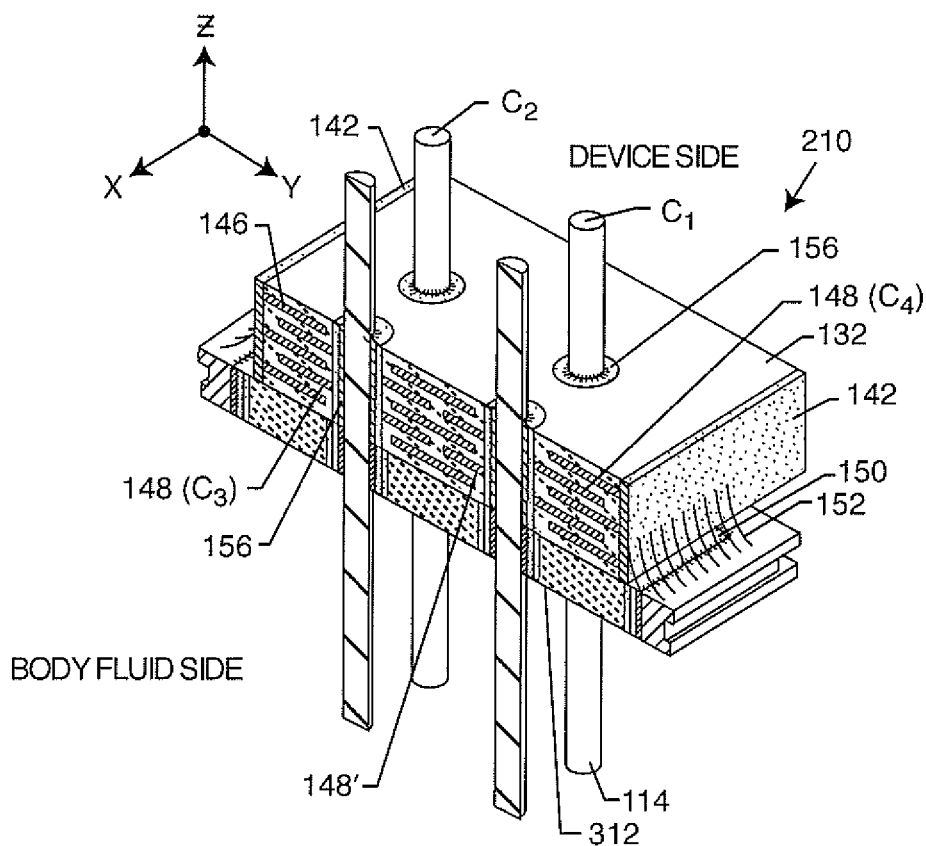
FIG. 22B is a sectional isometric view taken along lines 22B-22B from FIG. 22.

FIG. 22B is taken from section 22B-22B of FIG. 22, which is very similar to FIG. 22A, except this time, the section line, which is along the y axis, goes through two ($C_3$, $C_4$) of the active leadwire or lead pins. One can see that there are two sets of active electrodes 148 and 148', which are each conductively connected to the two associated leadwires. It will be understood that there are actually four sets of active electrode plates with two other sets being associated with the two other leads ($C_1$, $C_2$) through which the section does not pass. Also shown is the ground electrode plate 146, again, connecting from ground metallization 142 on each end of the capacitor. Referring once again to FIGS. 22A and 22B, it will be appreciated that both ends of the capacitor ground metallization 142 are connected with an electrical connection material 152 to sections of the hermetic seal gold braze 150, as illustrated. In this view, the metallization and gold braze is not shown on the insulator for simplicity.

Referring again to FIG. 22B and as defined herein, there is a first electrical connection material 156 that connects the active conductive pathway residing in the at least one active via hole in the insulator to the active metallization electrically connected to the at least one active electrode plate of the feedthrough capacitor. Also defined is a second electrical connection material 152 that electrically connects the capacitor ground metallization 142 connected to the at least one ground electrode plate of the feedthrough capacitor to the ferrule. These definitions do not mean that the electrical connection material 152 is connected only to the ferrule but can be connected to the ferrule through an intermediate material, such as a gold braze and the like, as previously described.

Figure 22C:
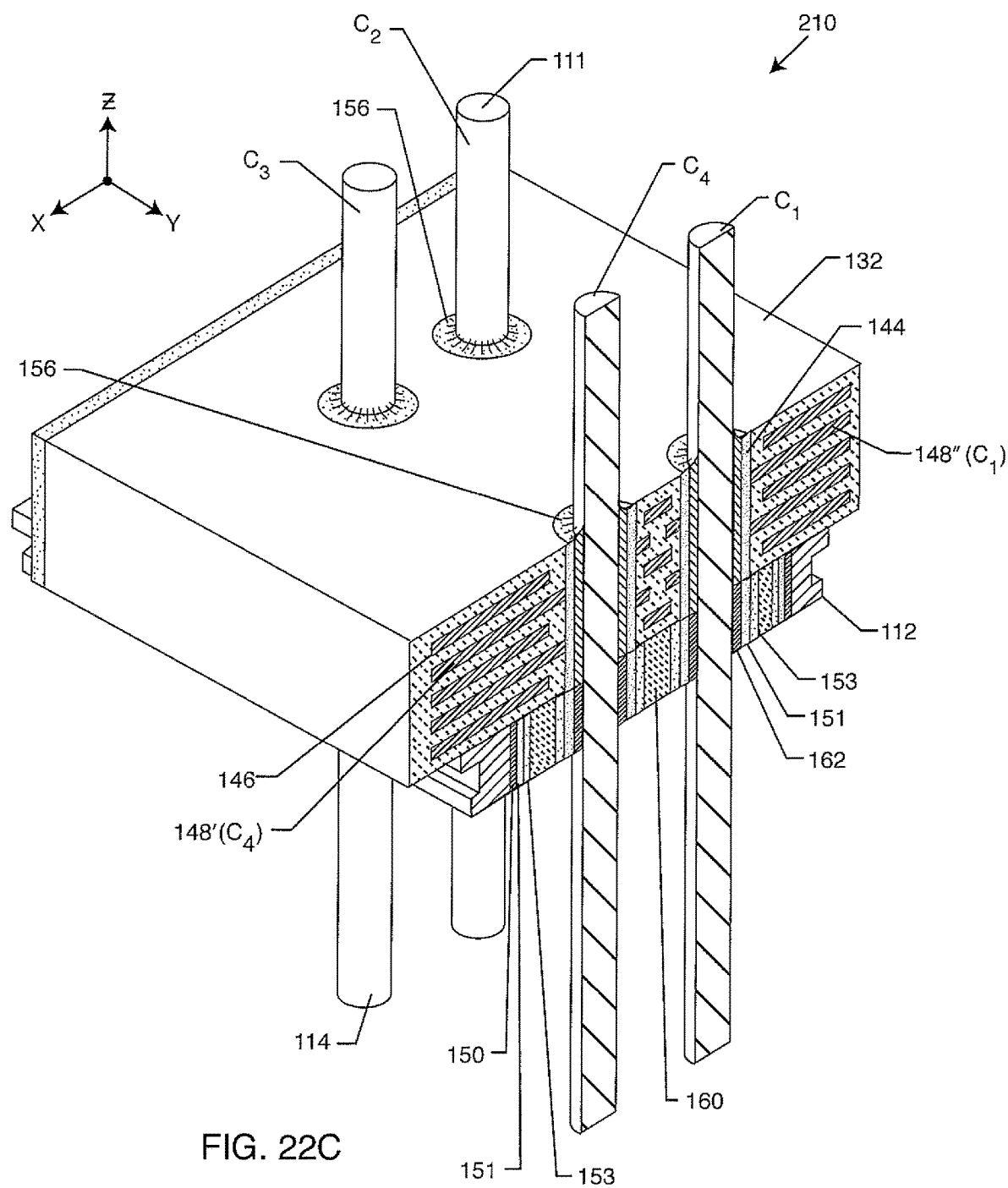
FIG. 22C is a sectional isometric view taken along lines 22C-22C from FIG. 22.

FIG. 22C is taken from section 22C-22C from FIG. 22 and is a sectional view generally taken along the x axis through pins $C_1$ and $C_4$. In this view, one can clearly see how the quadpolar feedthrough capacitor 132 overhangs the perimeter edges of the ferrule in the x direction. One can clearly see the active electrode plates 148' and in this case, 148", each associated with a leadwire 111.

FIG. 22C better illustrates two of the via holes in cross-section. One can see that the via holes 316 have an active via hole inner surface 318 as best seen in FIG. 21E. This active via hole inner surface 318 might be sputtered (metallized) after the insulator 160 is sintered, such that there is an adhesion layer 153 and wetting layer 151 suitable to accept a gold braze. In other embodiments, the passageway 316 may be filled by a substantially pure platinum via or a ceramic reinforced metal composite, as will be further described herein. In these cases, the conductive via passageway 316 would be co-sintered at the same time as the alumina insulator 160.

Figure 9:
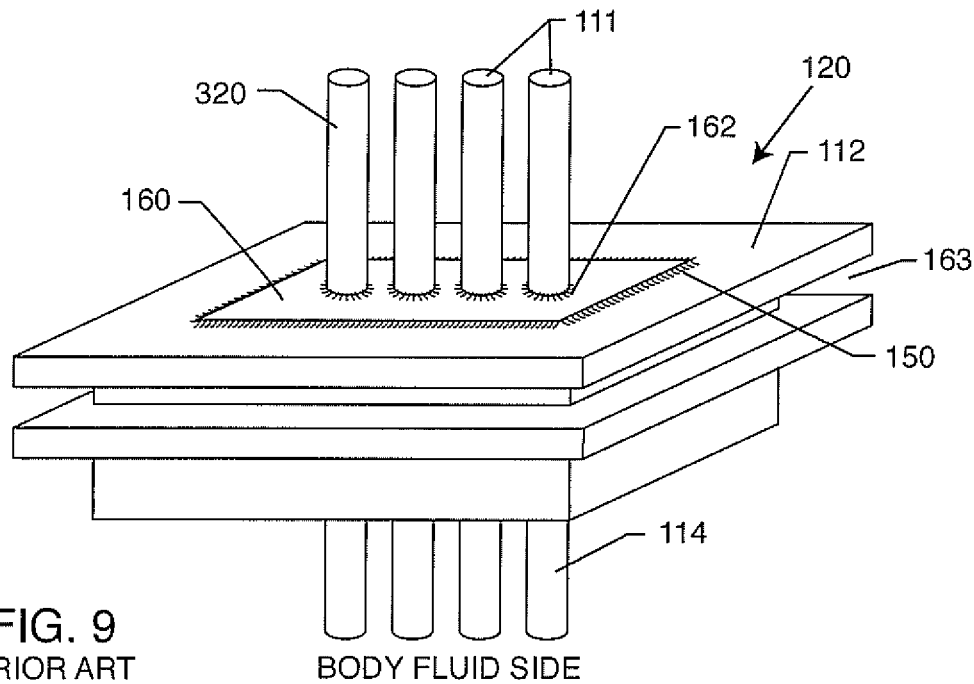
FIG. 9 is an isometric view illustrating the hermetic seal subassembly ready to receive the capacitor of FIG. 8.
Figure 10:
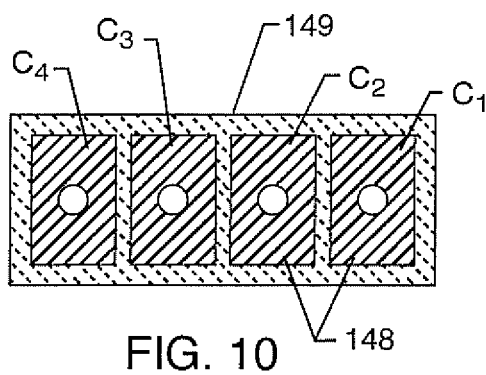
FIG. 10 is taken generally from section 10-10 from FIG. 8 showing the active electrode plates.

There is an active conductive pathway 320 that is formed through the insulator structure. This active conductive pathway can take the form of a leadwire, as illustrated in FIGS. 4, 9, 13 or it may take the form of any of the substantially pure platinum or ceramic reinforced metal composite co-sintered vias, as illustrated in FIGS. 39-45. Referring now back to FIGS. 22C, 22E, 22F and 22H to 22K, one can see that the feedthrough capacitor has a device side end surface 324 and a side of the capacitor 326 that is near or adjacent the ferrule. There is at least one active passageway 328 extending through the capacitor dielectric between the capacitor first and second surfaces 324 and 326. It will be appreciated that this conductive passageway, in many embodiments, extends outwardly beyond either capacitor surface 324, 326 or both. Also, the conductive pathway may extend beyond at least one of the ferrule device side or the ferrule body fluid side or both.

Figure 22D:
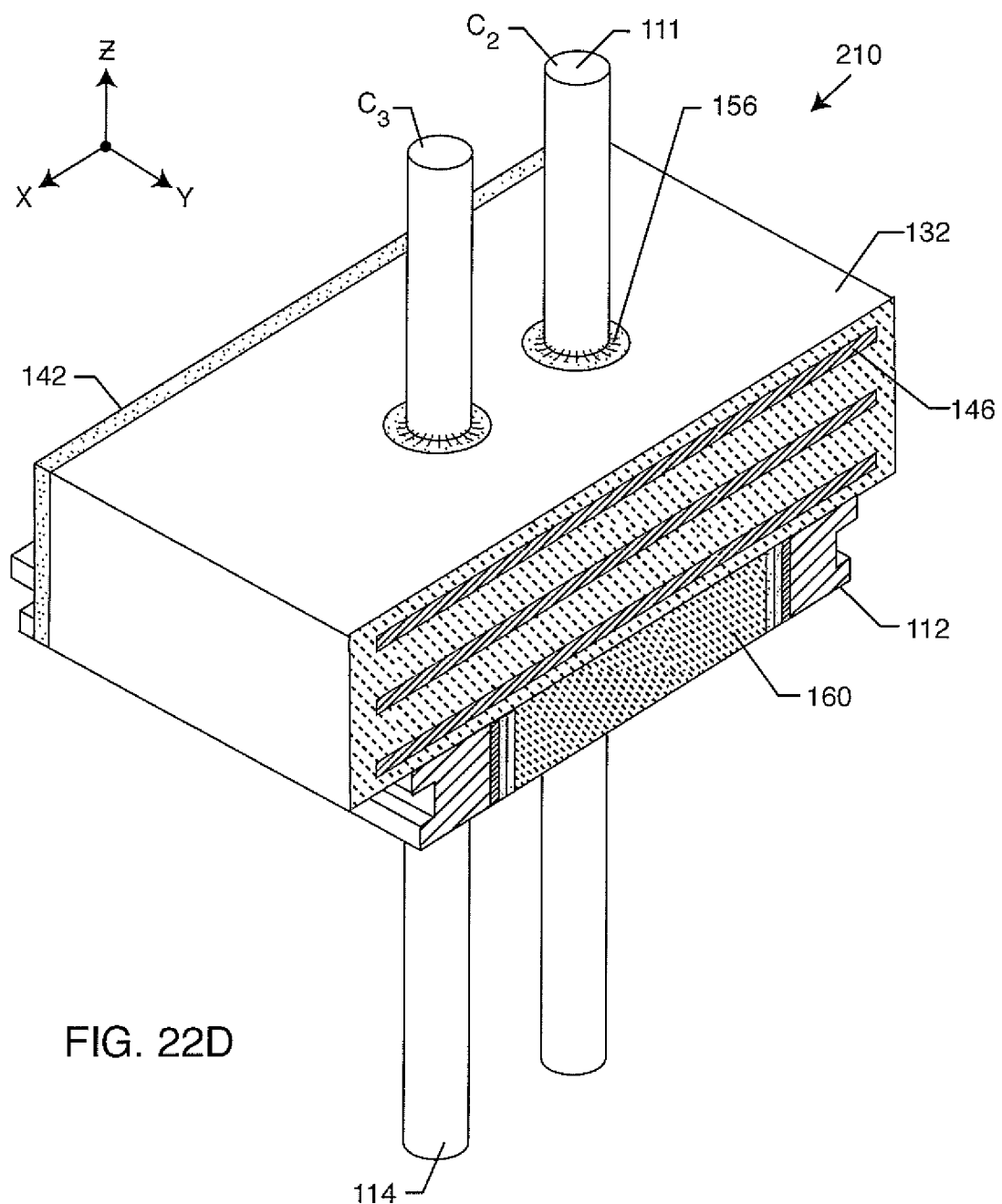
FIG. 22D is a sectional isometric view taken along lines 22D-22D from FIG. 22.

FIG. 22D is taken from 22D-22D from FIG. 22 and is very similar to FIG. 22C, except in this case, it does not cut through any of the active leadwire pins. This sectional cut is also taken in the margin area between active electrodes 148, such that none of the active electrodes are shown in FIG. 22D. Accordingly, the only electrodes that we can see in this view are ground electrodes 146. In FIG. 22D, one can see one of the novel aspects of the present invention that is where the capacitor overhangs the ferrule and where the ground electrodes 146 do not need to extend to the outer edges of the feedthrough capacitor. These outer edges are the parts of the overhanging capacitor in the y-z plane that overhang the ferrule.

Figure 22E:
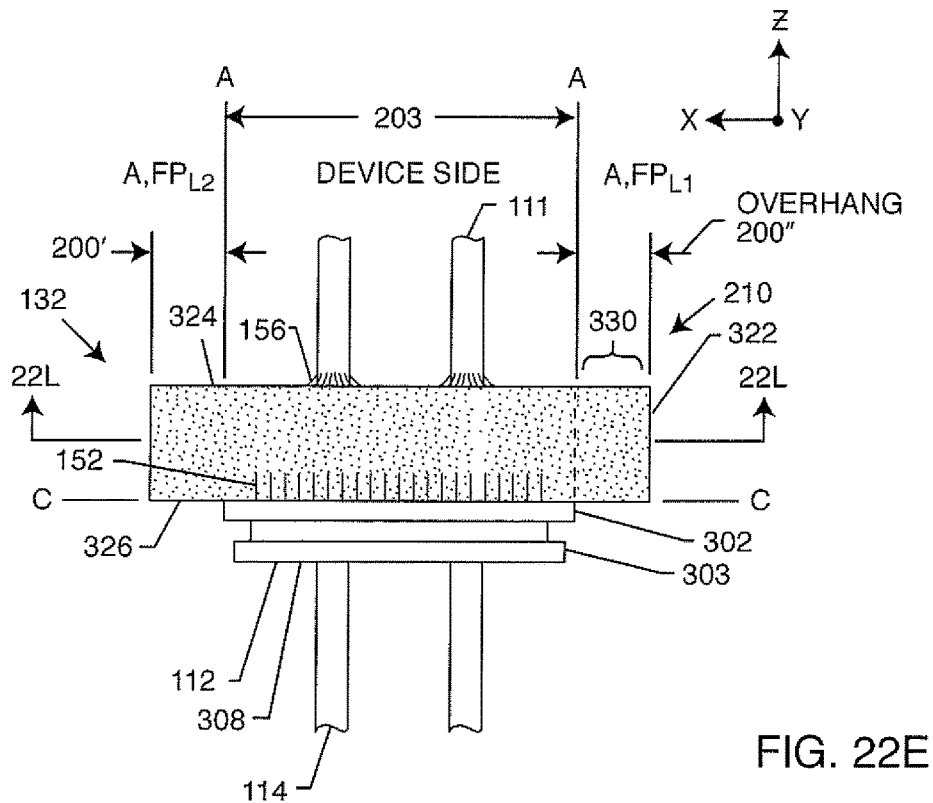
FIG. 22E is a side view taken along lines 22E-22E from FIG. 22.

FIG. 22E is a side view taken from isometric 22E-22E from FIG. 22. This is not a sectional view but illustrates the overhanging capacitor 132. As properly noted in FIG. 22E, this is drawn in the x-z plane. The perimeter edge of the ferrule is illustrated by line A-A. Line A-A is best thought of as a plane that goes in and out of the paper along the perimeter edge of the ferrule, as illustrated. One can clearly see the present invention in FIG. 22E, as the overhang 200, which overhangs line A-A. As illustrated in FIG. 22E, this overhang 200', 200" is on both sides. It will be appreciated that the overhang could be only on one side, but this would reduce the effective capacitance area of the two associated leadwires that are not on the overhanging side.

Figure 22F:
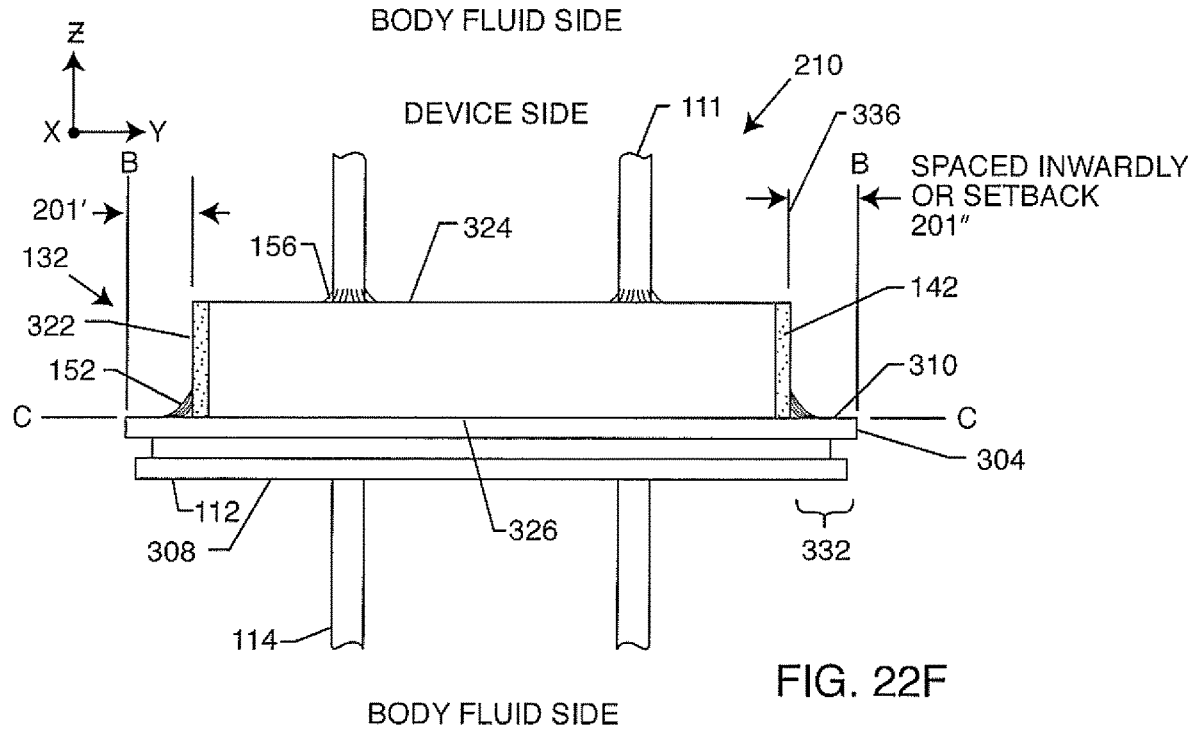
FIG. 22F is a side view taken along lines 22F-22F from FIG. 22.

FIG. 22F is another side view taken from isometric 22F-22F from FIG. 22. Again, in this case, there is no cross-hatching, and this shows the side view taken in the y-z plane. Again, an imaginary line B-B is shown along the edge of the capacitor which could also be thought of as a plane extending into and out of the paper. Importantly, in accordance with the present invention, there is a setback (spaced inwardly) 201' and 201", as illustrated. As will be seen in every embodiment, the setback 201 also enables an oxide-resistant conductive connection to the ferrule. In summary, the FIG. 22 series illustrates the present invention, in that, there is always a portion of the feedthrough capacitor perimeter that overhangs the ferrule (which increases the ECA) and there is also always a portion of the feedthrough capacitor perimeter that is setback (does not overhang) a portion of the ferrule perimeter or is aligned with the ferrule perimeter. In general, this setback area enables an oxide-resistant electrical connection generally to a gold or other noble surface.

Referring once again to FIGS. 22E and 22F, one can see that there is a line C-C, which in both cases can become a plane by imagining it extended in and out of the paper. This is the plane between the capacitor 132 and the ferrule and insulator 112, 160. It will be appreciated that the capacitor may lay directly against the insulator, the ferrule or both the insulator and the ferrule, or even that the capacitor may be spaced some distance away from the insulator and/or the ferrule by means of an adhesive washer, a spacer, an air gap or the like. Referring once again to FIG. 22E, one will also appreciate that in the present invention, the capacitor overhang area 200 may coincide substantially with line or plane A-A. By aligning the capacitor overhang edge 200 with the perimeter edge of the ferrule A-A, one still gains a substantial amount of ECA. Importantly, it is still necessary to have a setback 201, as illustrated in FIG. 22F, so that one can accomplish an oxide-resistant electrical ground connection 152.

Referring back to the imaginary projections of FIG. 21A, the imaginary projection planes FPL1, FPL2, FPW1 and FPW2 onto the capacitor dielectric second end surface 326 defines: at least one capacitor dielectric imaginary first overhang portion 200' or 200' or both 200' or 200' extending laterally outwardly beyond the ferrule outmost surface 302; and a capacitor dielectric imaginary second overlay portion 203 that overlays the ferrule device side end surface and overlays the hermetically sealed insulator, wherein, at least part of the capacitor dielectric outer side wall in the capacitor dielectric imaginary second overlay portion is spaced inwardly 201' or 201" from the ferrule outermost surface 304 and wherein, the at least one ground electrode plate at least partially resides in the capacitor dielectric imaginary second overlay portion.

Figure 22G:
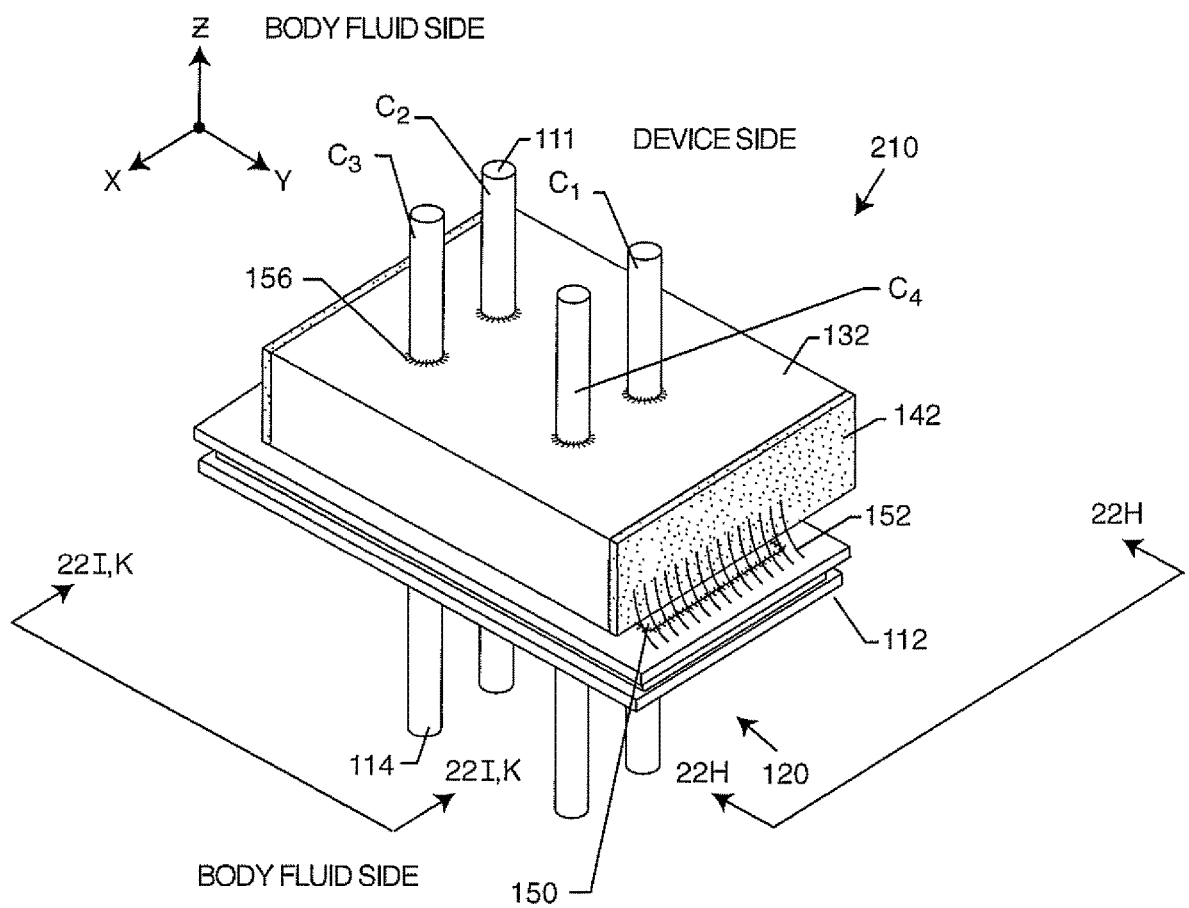
FIG. 22G is an isometric view of another embodiment of the present invention where now the capacitor only overhangs the ferrule along one edge of the ferrule.

FIG. 22G is very similar to FIG. 22, except that the feedthrough capacitor 132 only overhangs the ferrule 112 on one side, as illustrated. This is best illustrated in FIG. 22H where one can see that the feedthrough capacitor overhang portion 330 only overhangs on the right side of the ferrule and not the left side.

Figure 22H:
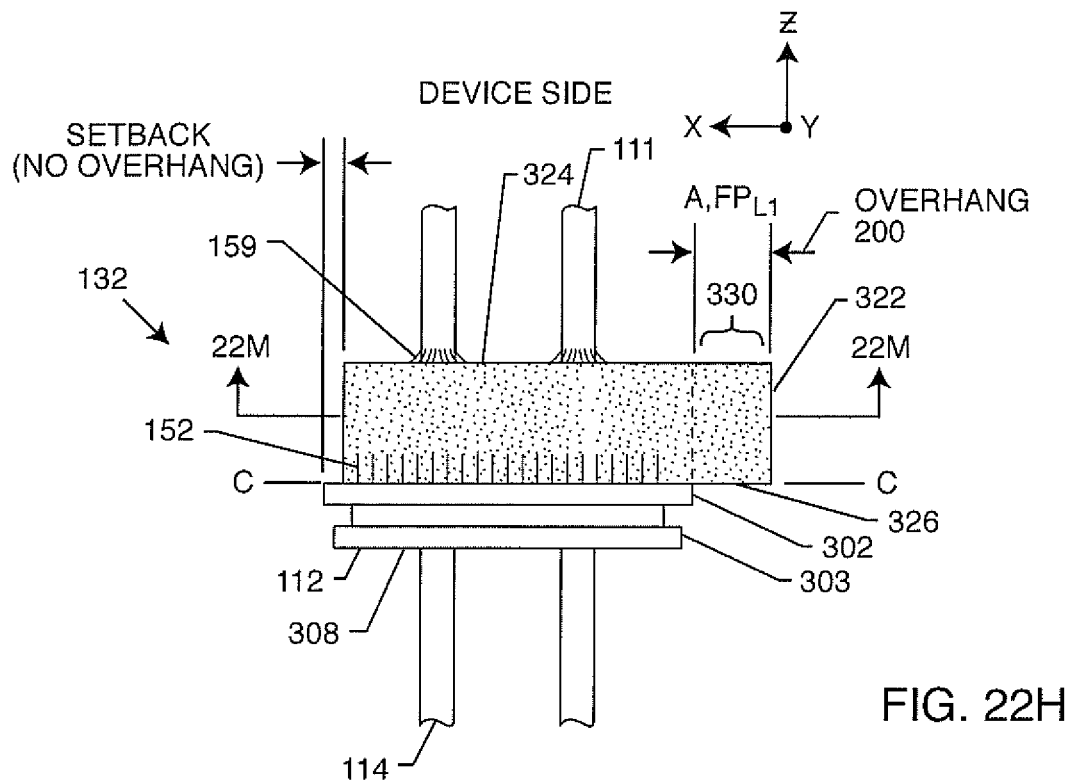
FIG. 22H is a side view taken along lines 22H-22H from FIG. 22G.
Figure 22I:
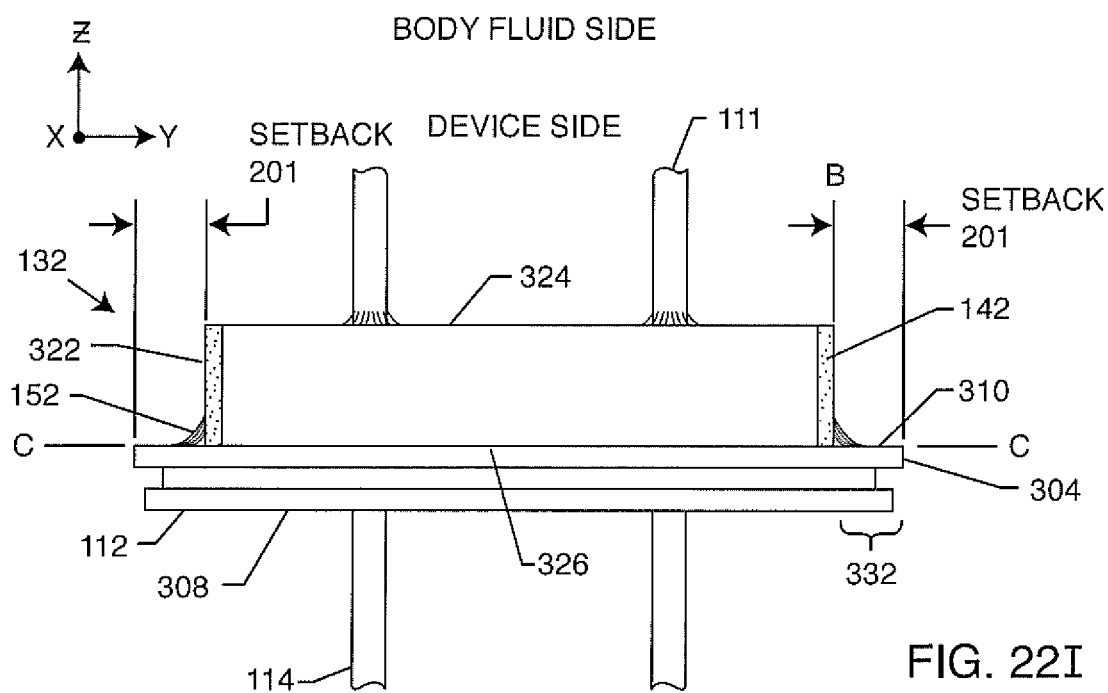
FIG. 22I is a side view taken along lines 22I-22I from FIG. 22G.

FIG. 22I is essentially the same as FIG. 22F, which illustrates that the feedthrough capacitor is spaced inwardly on both the right and the left sides from the ferrule outermost surface 304.

Figure 22J:
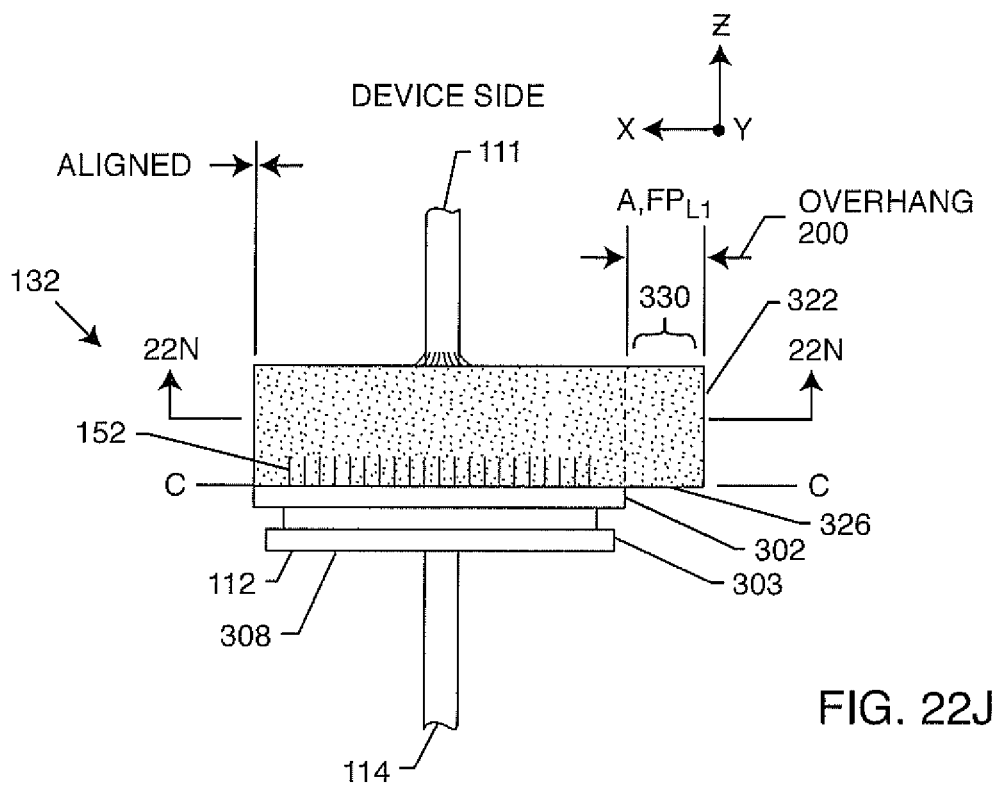
FIG. 22J is a side view similar to FIG. 22H now showing a new embodiment similar to FIG. 22G where the capacitor is aligned along the left side.

FIG. 22J is very similar to FIG. 22H, except on the left side, the capacitor is aligned with the ferrule outermost surface 302, as indicated. So, in this case, the capacitor is overhanging on the right side 330 and is aligned on the left side.

Figure 22K:
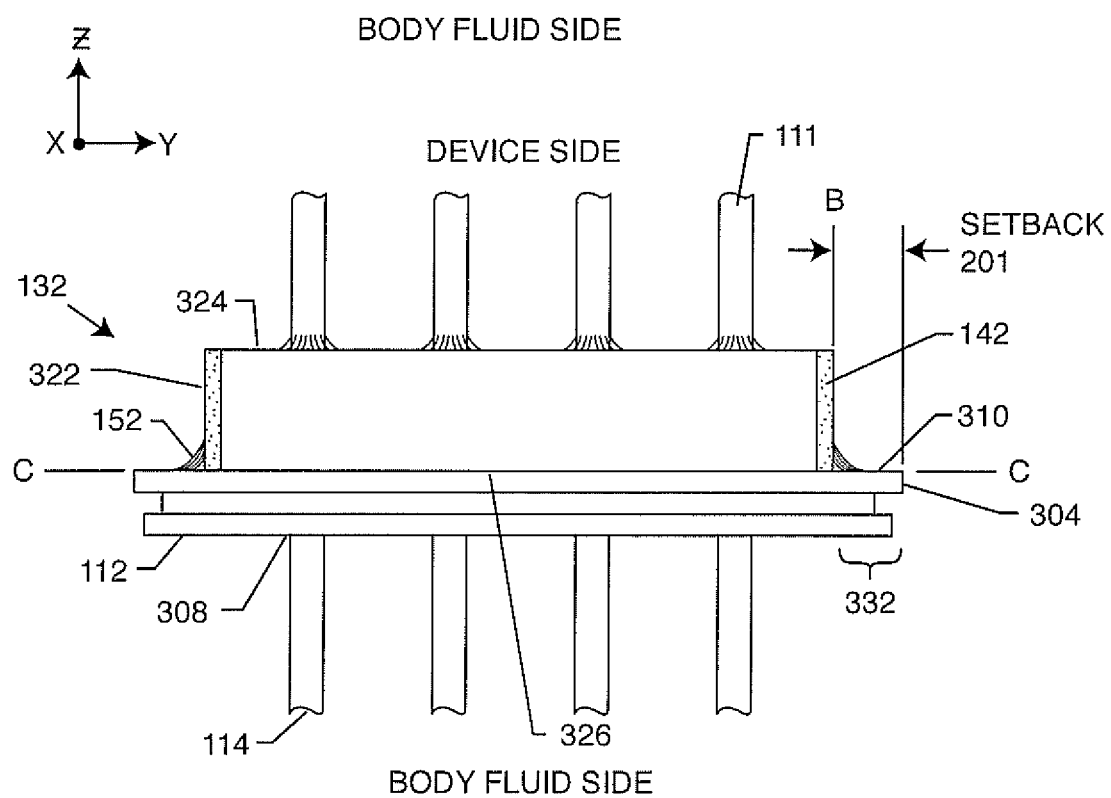
FIG. 22K is a side view similar to FIG. 22I if it was taken of the structure of FIG. 22J along the lines 22H-22H of FIG. 22G.

FIG. 22K is exactly the same as FIG. 22I because from this perspective, they are both the same.

Figure 22L:
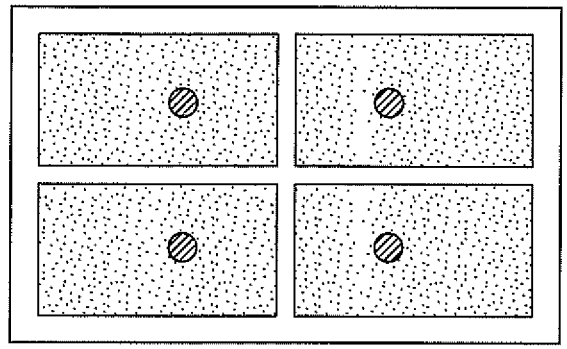
FIG. 22L is a sectional view of the active electrode plates taken along lines 22L-22L of FIG. 22E.

FIG. 22L illustrates the active electrode plates of the capacitor illustrated in FIGS. 22 and 22E. One can see that the active electrodes of all four of the quad polar capacitors are equal in this view.

Figure 22M:
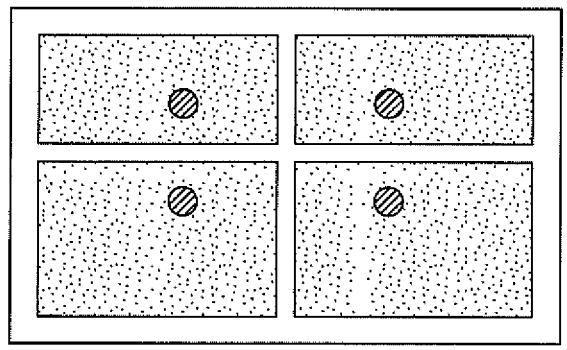
FIG. 22M is a sectional view of the active electrode plates taken along lines 22M-22M of FIG. 22H.

FIG. 22M illustrates the active electrodes of the feedthrough capacitor of FIG. 22H that only overhangs on one side. The overhang on the one side makes the active electrodes on that side much larger and hence the capacitor value is larger. By only overhanging on one side, however, the effective capacitance area where active electrode plates become smaller. Referring once again to FIG. 22H, this means that the capacitors for the leadwires on the left is lower than the capacitance for the leadwires 111 on the right.

Figure 22N:
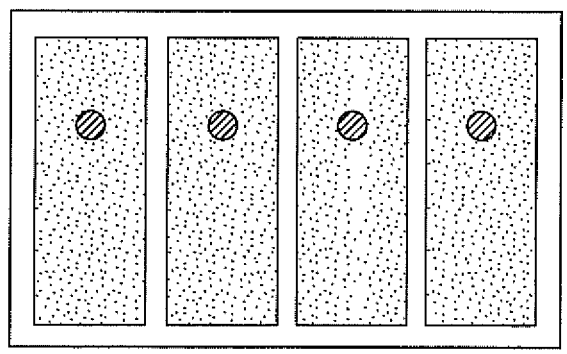
FIG. 22N is a sectional view of the active electrode plates taken along lines 22N-22N of FIG. 22J.

FIG. 22N illustrates the active electrode plates taken from FIGS. 22J and 22K. In this case, the four-quad polar leadwires are inline. Again, because the capacitor is overhanging on one side and not the other, this results in asymmetry of the active electrode plates, as indicated. This asymmetry is not a disadvantage in that, the effective capacitance area or electrode plate area is equal for all four of the active electrodes.

Figure 22O:
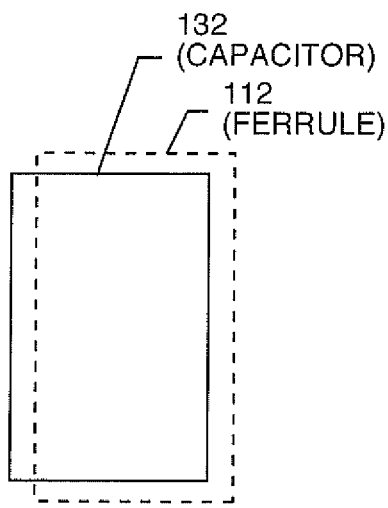
FIG. 22O is a simplified top view illustrating one embodiment of the capacitor overhanging the ferrule.
Figure 22P:
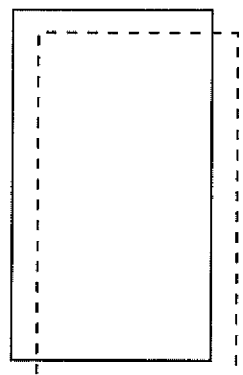
FIG. 22P is a simplified top view illustrating another embodiment of the capacitor overhanging the ferrule.
Figure 22Q:
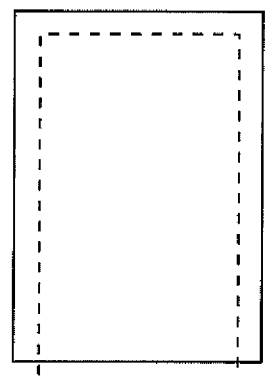
FIG. 22Q is a simplified top view illustrating another embodiment of the capacitor overhanging the ferrule.

FIGS. 22O through 22W indicate various alignments of the capacitor 132 (shown with a solid line) as it overlays the top view of the ferrule 112 (indicated by the dash lines). In accordance with the present invention, as illustrated in FIG. 22O, the feedthrough capacitor need only overhang one side or portion of the ferrule. It is also important that the capacitor be set back or not overhang at least a portion of the ferrule.

Figure 22R:
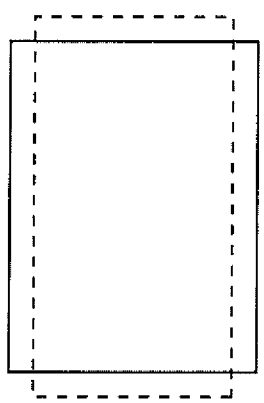
FIG. 22R is a simplified top view illustrating another embodiment of the capacitor overhanging the ferrule.
Figure 22S:
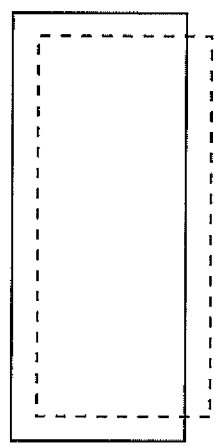
FIG. 22S is a simplified top view illustrating another embodiment of the capacitor overhanging the ferrule.
Figure 22T:
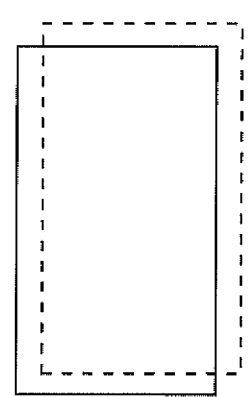
FIG. 22T is a simplified top view illustrating another embodiment of the capacitor overhanging the ferrule.
Figure 22U:
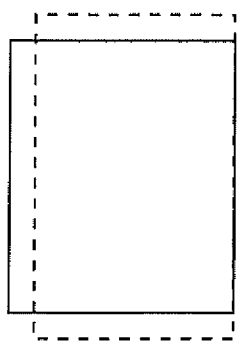
FIG. 22U is a simplified top view illustrating another embodiment of the capacitor overhanging the ferrule.
Figure 22V:
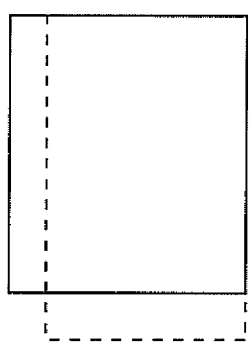
FIG. 22V is a simplified top view illustrating another embodiment of the capacitor overhanging the ferrule.
Figure 22W:
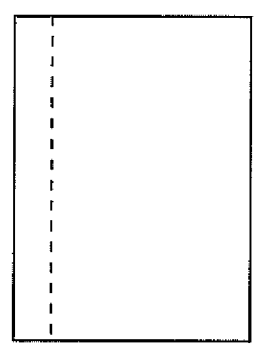
FIG. 22W is a simplified top view illustrating another embodiment of the capacitor overhanging the ferrule.

In particular FIG. 22R illustrates perhaps the most likely form of the present invention wherein, the feedthrough capacitor overhangs opposite sides of the ferrule and is held back or set back from the other two sides of the ferrule. This allows for a proper ground attachment to a gold braze and in turn, to the ferrule while at the same time, allows for the resulting active electrode plates to all be equal and therefore, result in equal filter performance for each of the leads. Having equal filter performance on each of the leads is the common practice in the AIMD industry.

Figure 23:
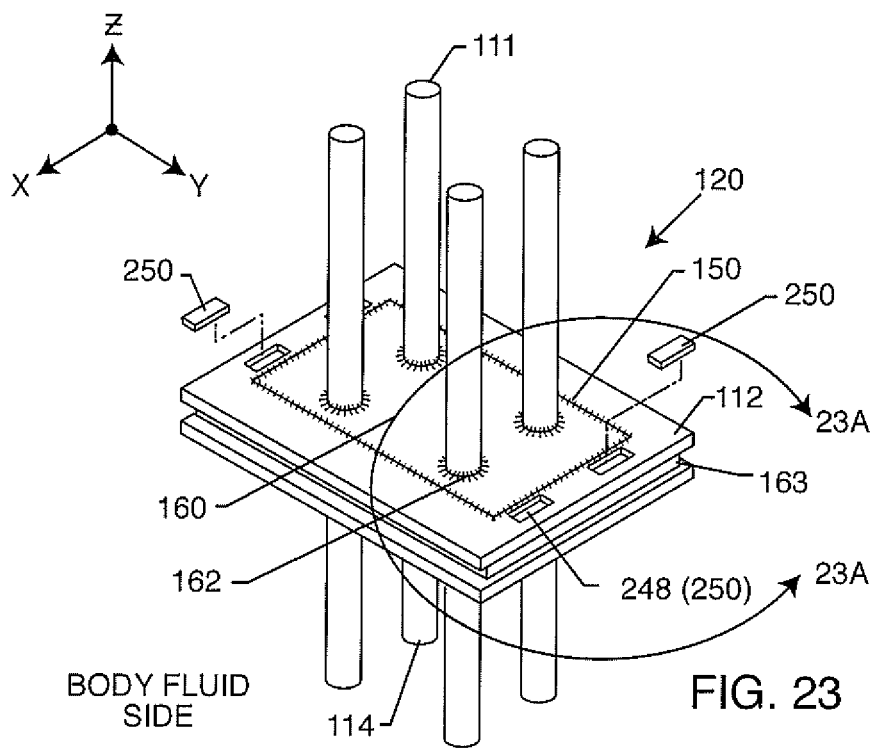
FIG. 23 is an isometric view of another embodiment of the present invention now having gold pocket pads.

FIG. 23 is an isometric view of a hermetic seal subassembly 120 similar to that previously described in FIG. 21F. As one can see, there is a gold braze 150 between ferrule 112 and insulator 160. It will be appreciated that one can only extend this gold braze 150 outwardly so much before it would interfere with the can half clam shell mating structure 163. One can see that four novel gold-filled pockets 248 (250) have been formed. In general, these pockets are like little swimming pools that are machined at the time that the ferrule 112 is formed. Then at the same time that gold brazes 150 and 162 are formed, then gold preforms 250 are reflowed thereby, creating four oxide-resistant noble metal attachment surfaces.

Figure 23A:
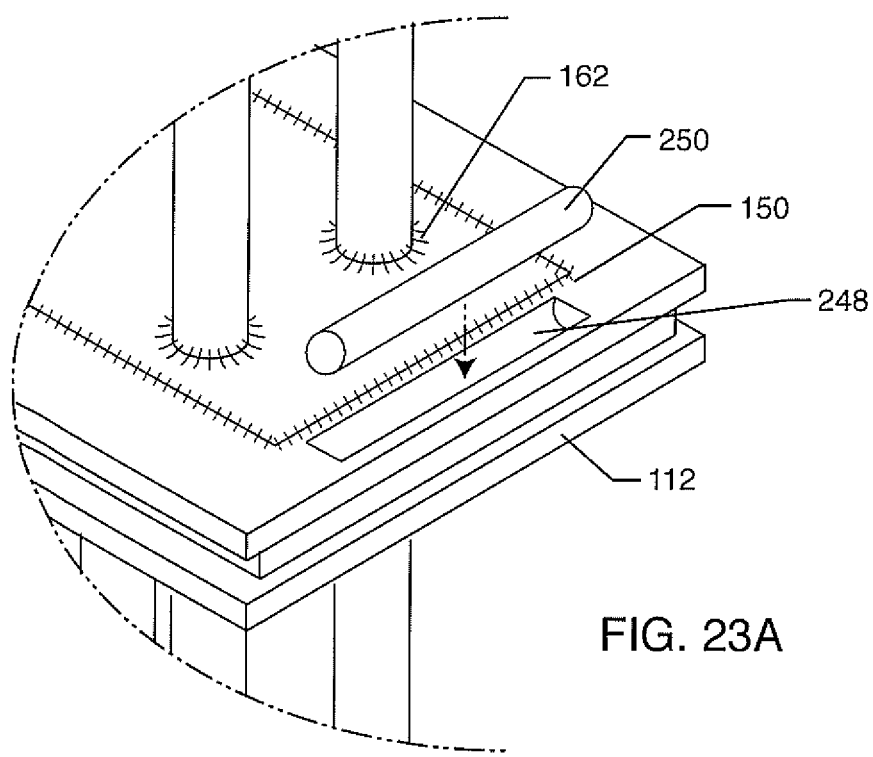
FIG. 23A is an enlarged isometric view of another embodiment of a pocket with an oxide-resistant metal trough or an oxide-resistant metal addition such as platinum wire for grounding.

Referring back to FIG. 23, it will be appreciated that the gold pockets 248, 250 can be joined on each end into a trough into which a small diameter gold wire is placed prior to gold brazing. This is best illustrated in FIG. 23A, which is taken from section 23A-23A from FIG. 23. Shown is a small diameter gold wire 250 ready to be placed into an elongated gold pocket receptacle 248. In general, gold braze 250 is reflowed at the same time that the hermetic seal gold brazes 150 and 162 are formed. Alternatively, wire 250 may comprise an oxide-resistant metal addition such as a brazed or laser welded gold, platinum, palladium, silver, and combinations thereof. Additionally, the wire 250 may further comprise a clip, a pad, an L-shaped pad, and an L-shaped pad with cutouts. Wire 250 may comprise any of the metal additions described in U.S. Pat. No. 9,931,514, the contents of which are incorporated fully herein by reference.

Figure 25:
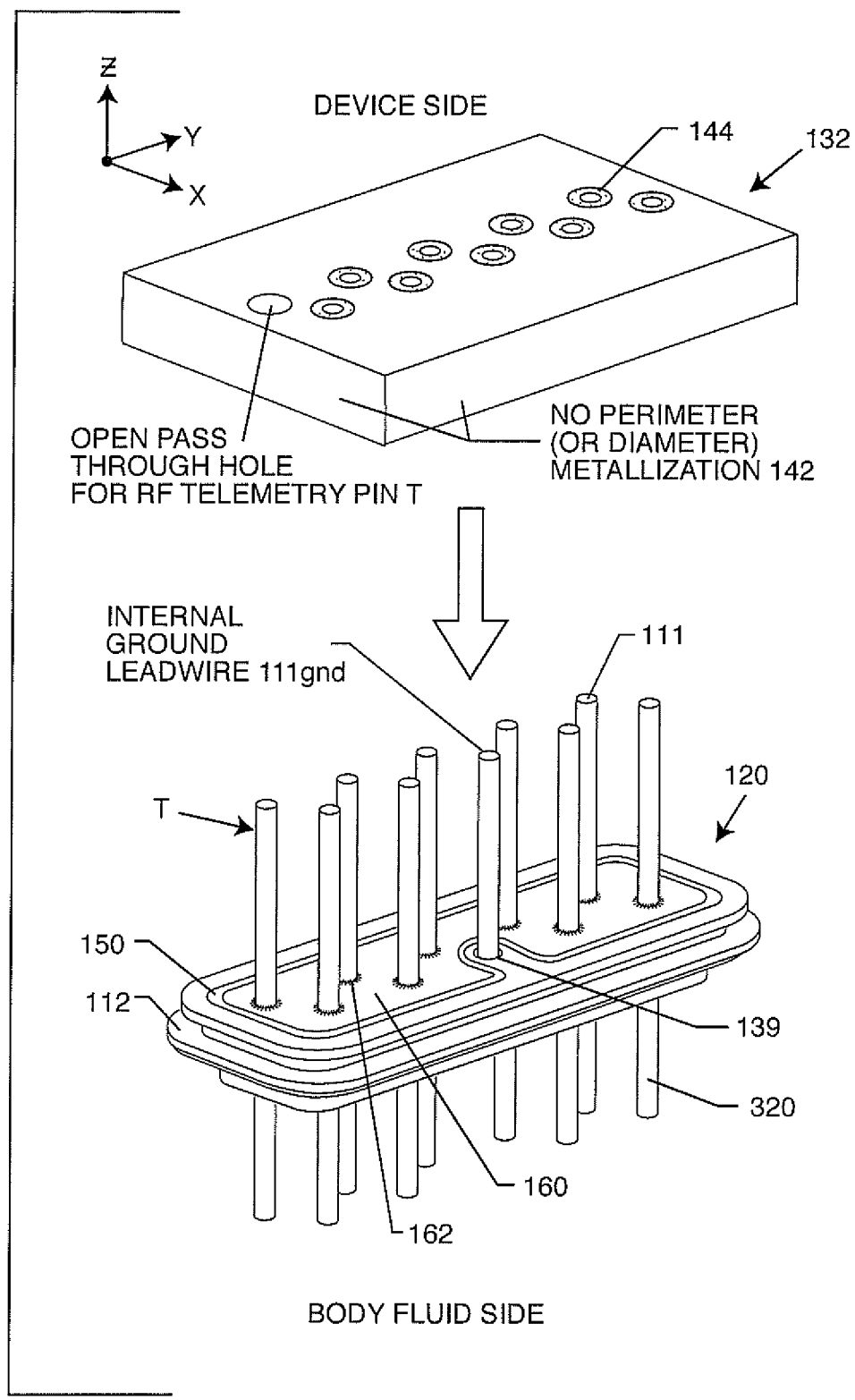
FIG. 25 is an exploded isometric view of another embodiment of the present invention.

FIG. 23 was taken from FIG. 25 of U.S. patent application Ser. No. 15/943,998, the contents of which are incorporated in full herein. A major advantage of these pocket pads is that much less gold braze is required to form the hermetic seal 150 between the ferrule 112 and insulator 160. In addition, the gold pocket pads are so thin that they can be placed right over the can capture area 163.

Figure 24:
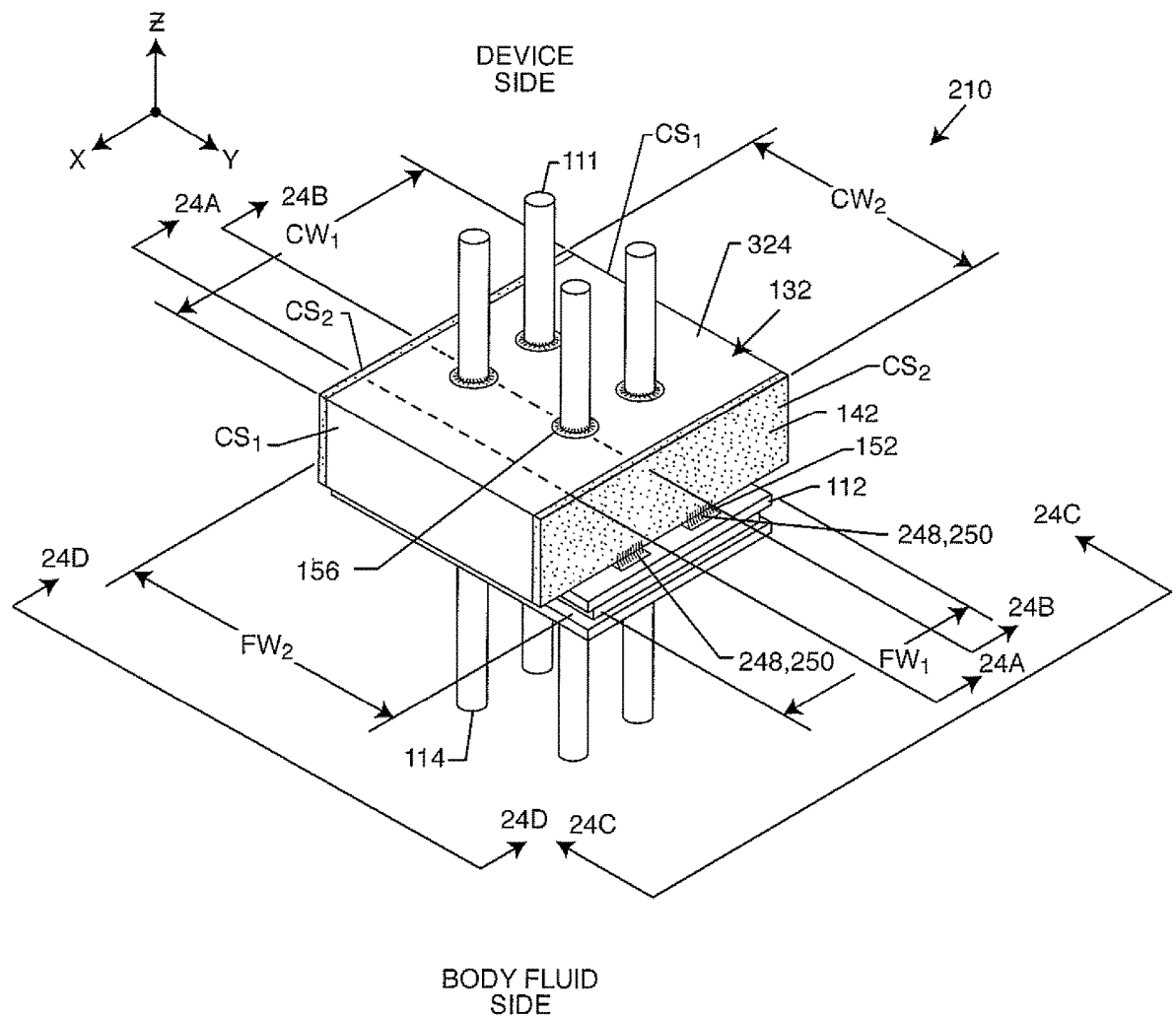
FIG. 24 is an isometric view of the present invention similar to FIG. 23 now with an overhanging capacitor.

FIG. 24 illustrates a quadpolar feedthrough capacitor 132 mounted to the hermetic seal with gold pocket pads of FIG. 23. This allows the feedthrough capacitor to be wider $CW_1$. In accordance with the present invention, the feedthrough capacitor 132 overhangs the outermost perimeter of the ferrule $FW_1$ as indicated. This is known as the capacitor overhang area. This capacitor overhang area is generally oriented in the x direction. When one looks at the y direction, one will see that the capacitor 132 is setback from the edge of the ferrule perimeter. In other words, dimension $CW_2$ is either less than or substantially equal to $FW_2$. In summary, in accordance with the present invention, the feedthrough capacitor of FIG. 24 overhangs in the x direction and is setback (or aligned) in the y direction. Also, in accordance with the present invention, an oxide-resistant electrical connection 142 is made between the feedthrough capacitor ground metallization 142 and each of the four-gold pocket pad 248, 250 as indicated with electrical connection material 152. It will be appreciated that the number of gold pocket pads can be increased, decreased or even merged together. It will also be appreciated that the electrical connection material 152 can comprise thermal-setting conductive adhesive, a solder, a braze or the like.

Figure 24A:
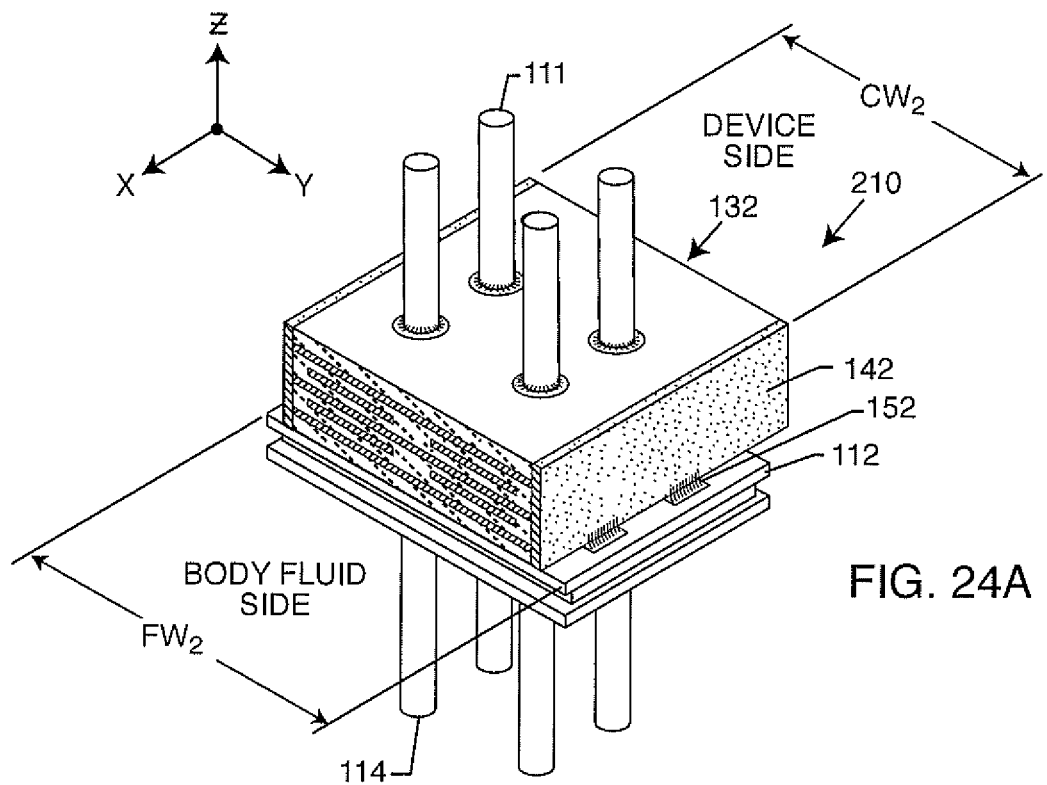
FIG. 24A is a sectional isometric view taken along lines 24A-24A from FIG. 24.
Figure 24B:
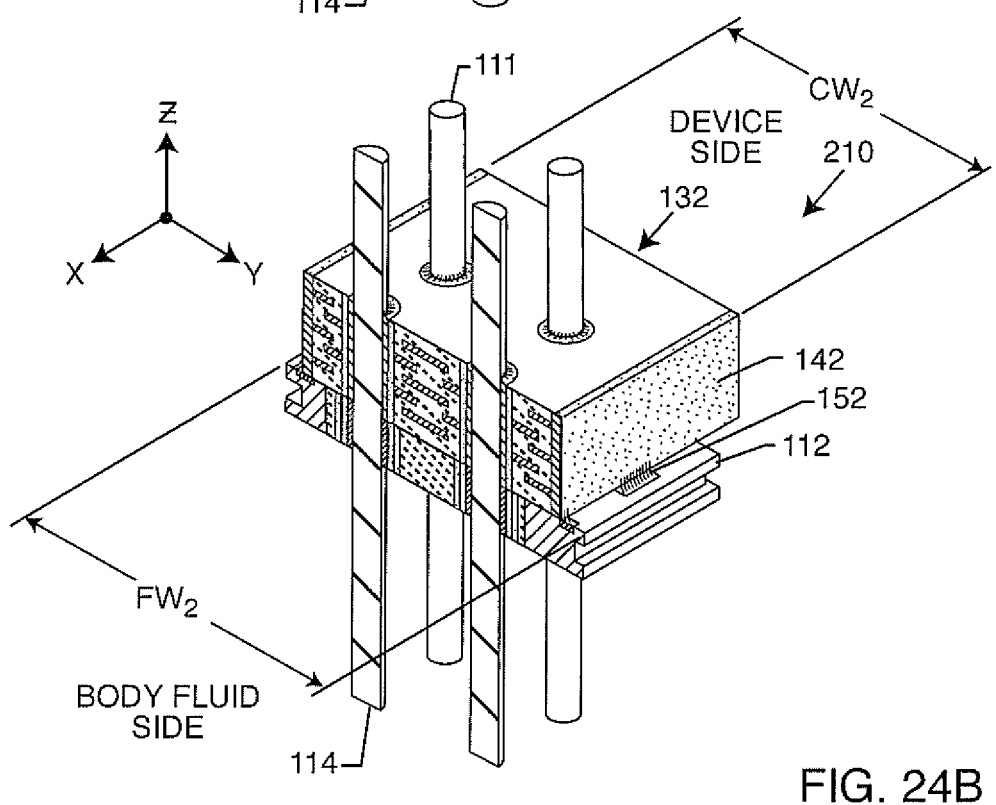
FIG. 24B is a sectional isometric view taken along lines 24B-24B from FIG. 24.

FIG. 24A is taken from section 24A-24A from FIG. 24. FIG. 24A illustrates that the feedthrough capacitor 132 is setback on both of its sides from the ferrule width $FW_2$. This is also illustrated in FIG. 24B.

Figure 24C:
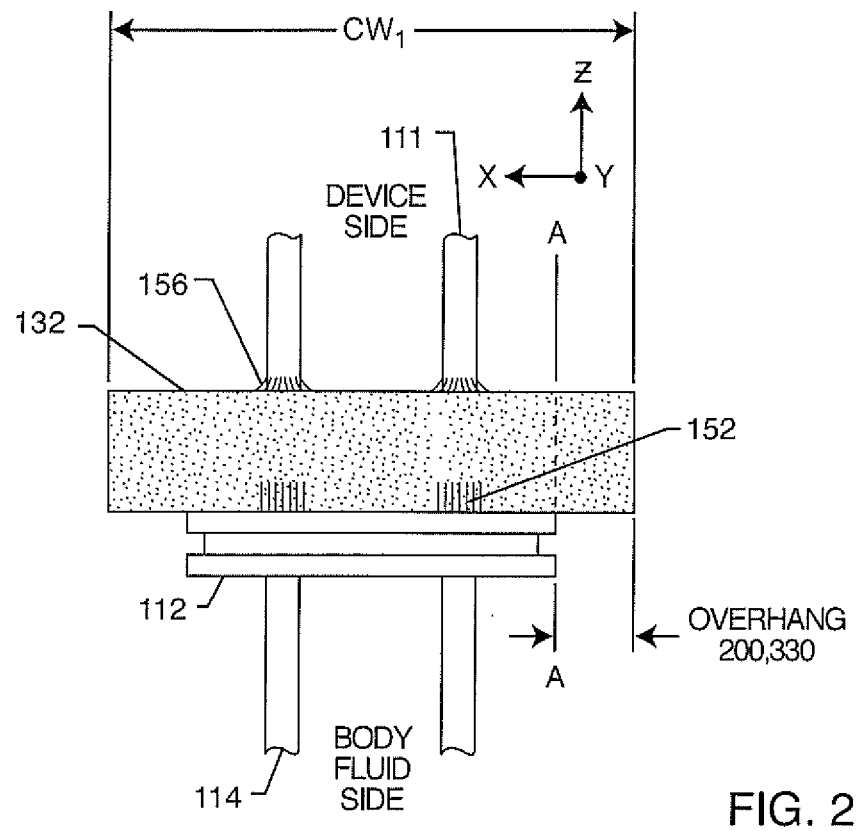
FIG. 24C is a side view taken along lines 24C-24C from FIG. 24.

FIG. 24C is a side view taken from 24C-24C from FIG. 24. This is very similar to FIG. 22E, except that the electrical connections are to the gold pockets and not to the hermetic seal gold braze.

Figure 24D:
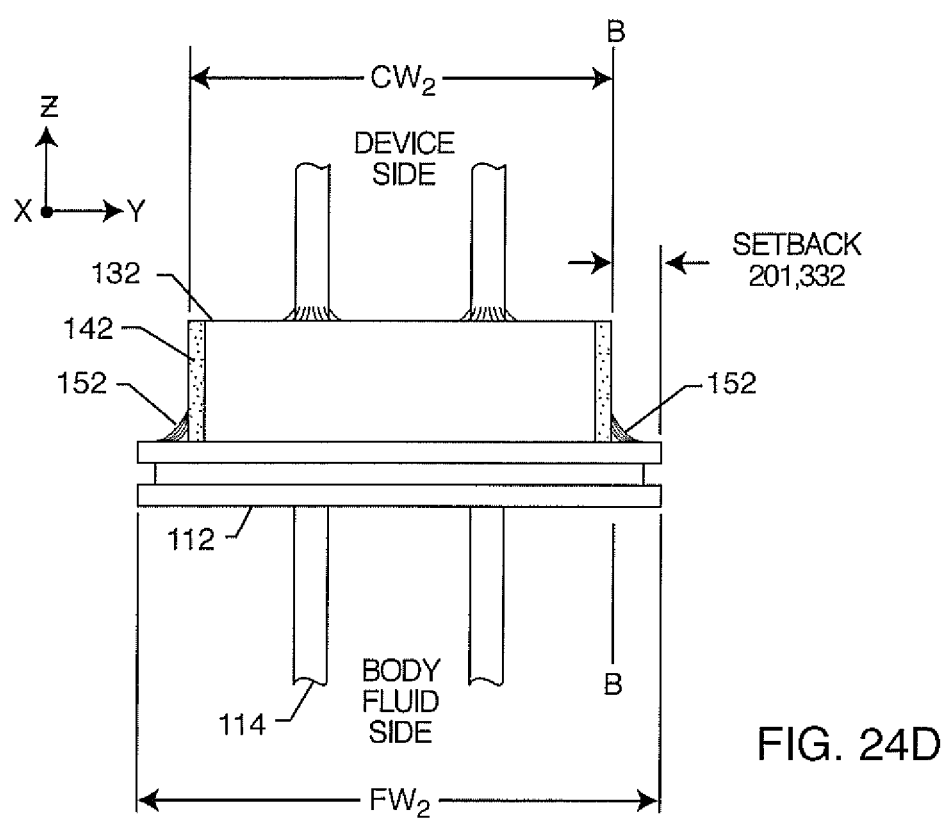
FIG. 24D is a side view taken along lines 24D-24D from FIG. 24.

FIG. 24D is a side view taken from 24D-24D from FIG. 24. This figure is very similar to FIG. 22F and illustrates that the capacitor is setback in its width from the ferrule. In summary, FIG. 24C illustrates the side (pictorial) view in the x-z plane clearly illustrating that the feedthrough capacitor 132 overhangs 200 ferrule 112. As mentioned in FIG. 24D, the capacitor can be substantially aligned with the edge of the ferrule or setback 201, as illustrated.

Figure 11:
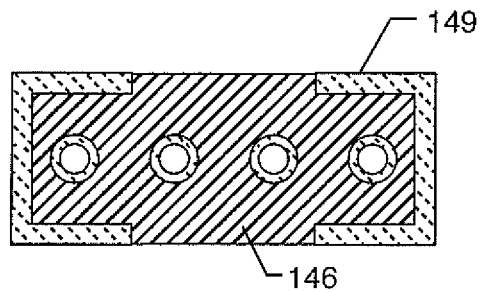
FIG. 11 is taken generally from section 11-11 from FIG. 8 showing the ground electrode plate.
Figure 12:
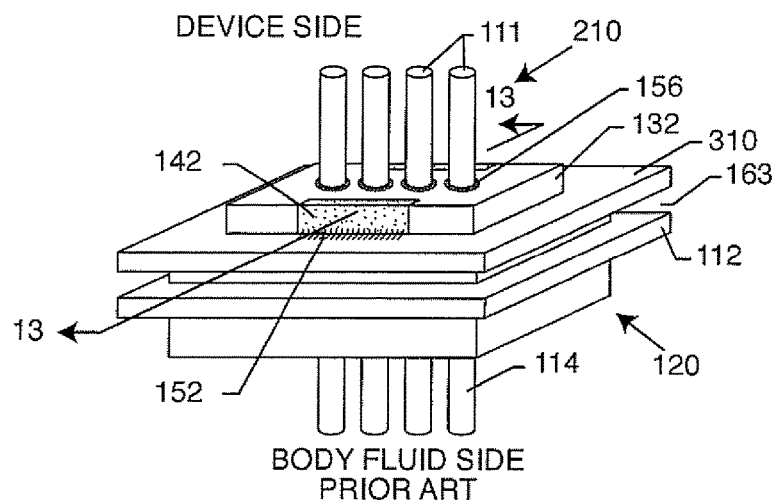
FIG. 12 illustrates the feedthrough capacitor installed to the hermetic seal assembly as previously described in FIGS. 8 and 9.

FIG. 25 is an internally grounded capacitor with a ferrule peninsula 139. An internally grounded capacitor with a ferrule peninsula is taught in FIGS. 11a, 11b and 11c in U.S. patent application Ser. No. 15/863,194, the contents of which are incorporated herein fully be reference. Referring back to FIG. 25, one can see that in the x-z direction, the feedthrough capacitor 132 overhangs the ferrule 112.

Figure 26:
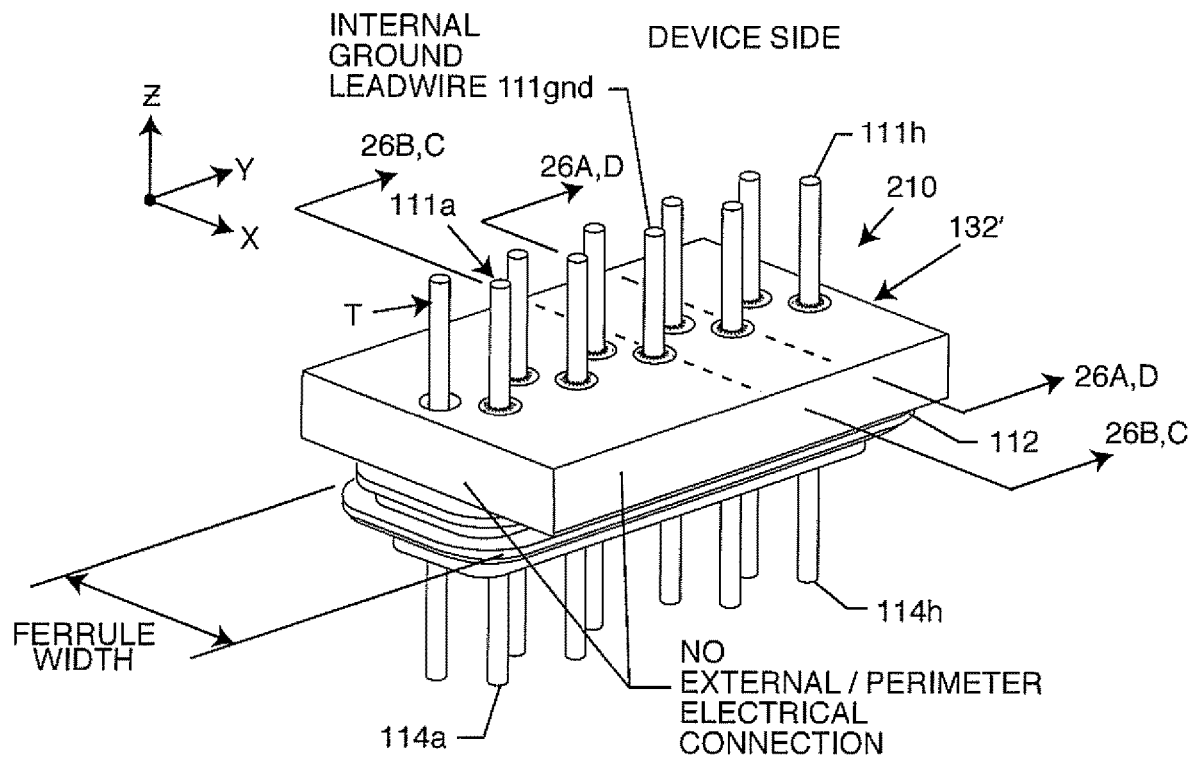
FIG. 26 is an isometric view of the structure of FIG. 25 now with the capacitor installed.

This is best illustrated in FIG. 26, where one can see the feedthrough capacitor mounted to the ferrule wherein, it clearly overhangs the width of the ferrule in the x-z plane. It will also be noted that this feedthrough capacitor, since it is internally grounded, has no external or perimeter electrical metallization or electrical connection to the ferrule. The entire grounding of the feedthrough capacitor internal ground electrodes are through internal ground leadwire 111gnd. Accordingly, the feedthrough capacitor is also not constrained in the y-z orientation either. In this case, the feedthrough capacitor is shown nearly aligned with the outermost edge of the length of the ferrule and overhang substantially along the width of the ferrule.

Figure 26A:
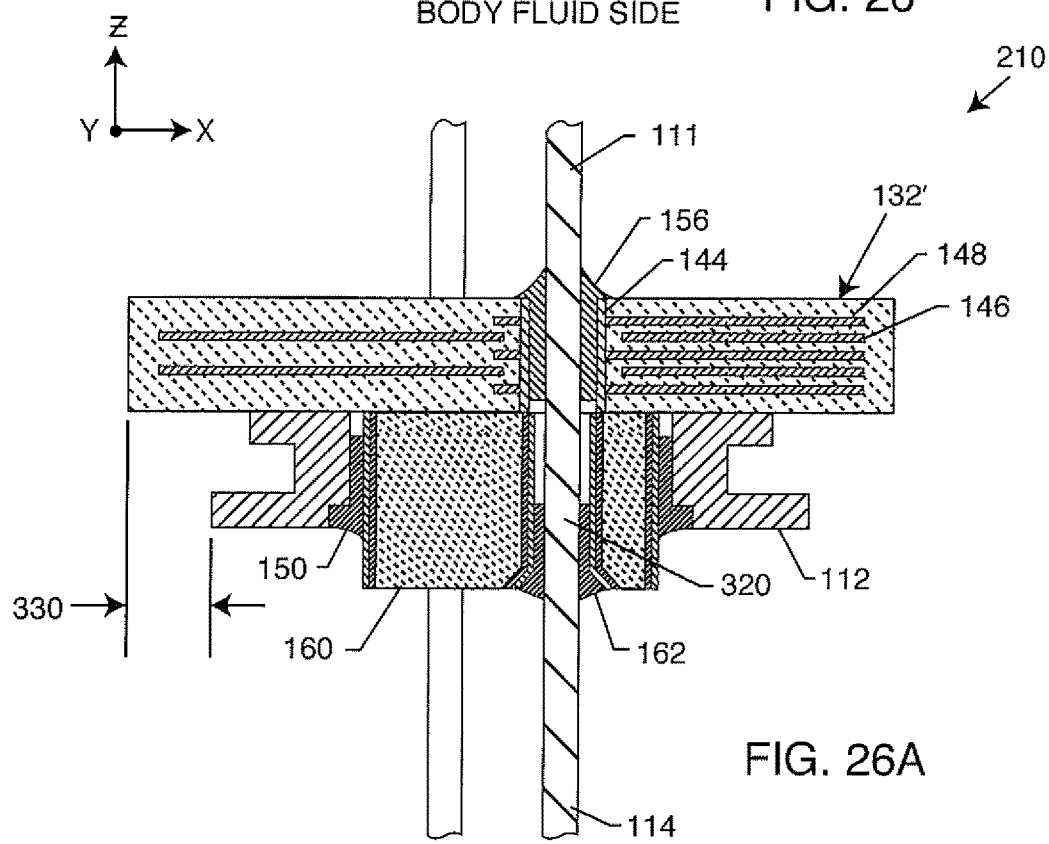
FIG. 26A is an isometric view taken along lines 26A-26A from FIG. 26.

FIG. 26A is taken from section 26A-26A from FIG. 26. FIG. 26A is drawn in the x-z plane clearly showing how the internally grounded feedthrough capacitor 132 overhangs the widest width of the ferrule 112. FIG. 26A is sectioned through one of the active pins 111 and shows that it is electrically connected 156 to active metallization 144, which is connected to its active electrode plates 148, as shown.

Figure 26B:
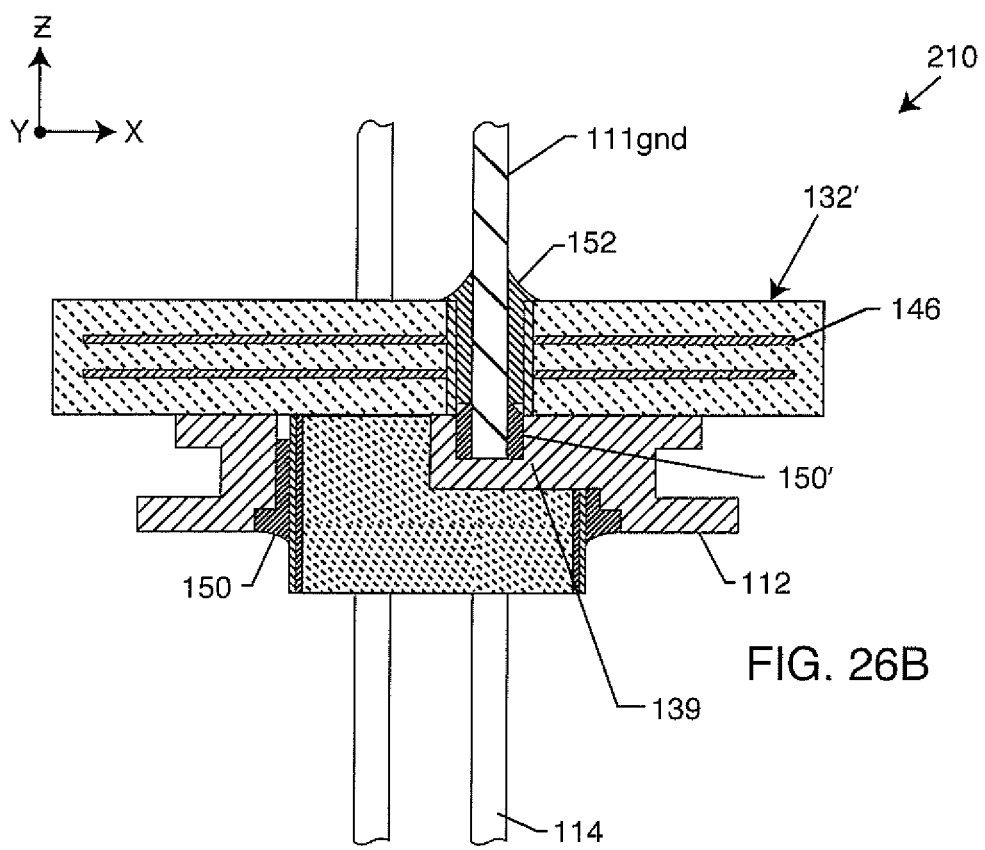
FIG. 26B is an isometric view taken along lines 26B-26B from FIG. 26.

FIG. 26B is taken from section 26B-26B from FIG. 26 and is very similar to FIG. 26A, except that this is sectioned through the ground pin 111gnd. One can see that the ground pin is gold braze 150' into the ferrule 122 peninsula structure 139 as indicated. FIG. 26B also shows that the grounded pin 111gnd is connected to the corresponding set of capacitor ground electrode plates 126.

Figure 26C:
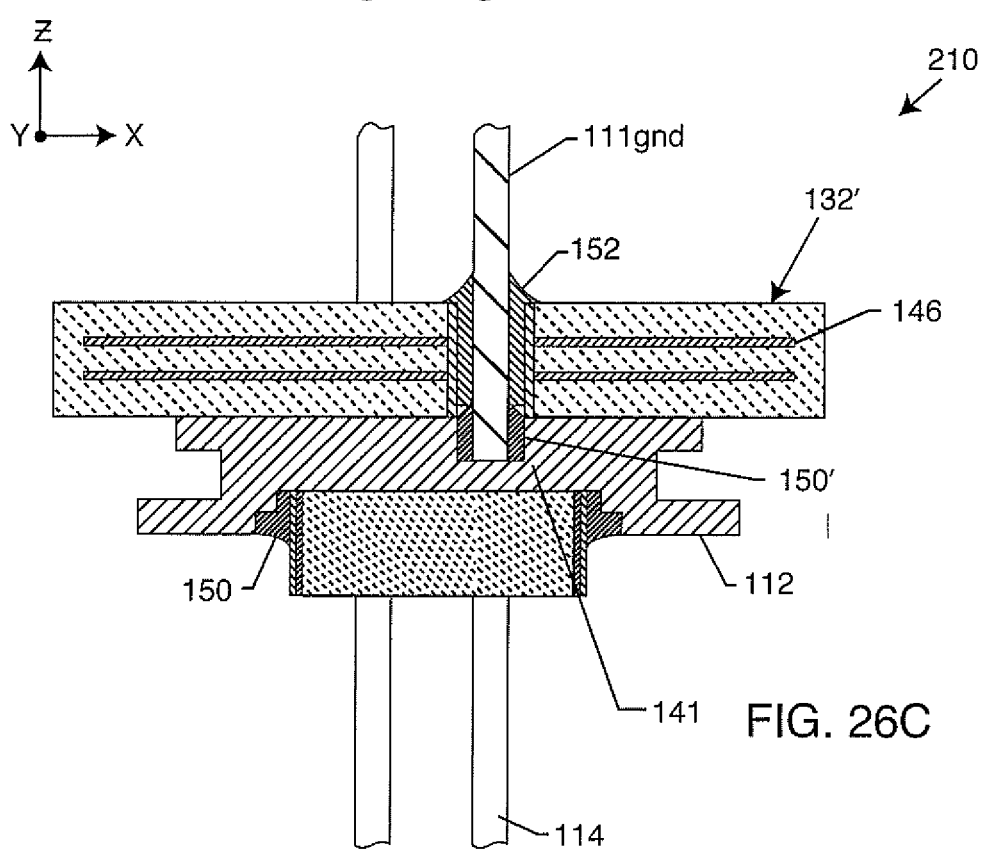
FIG. 26C is an isometric view taken along lines 26C-26C from FIG. 26.
Figure 40:
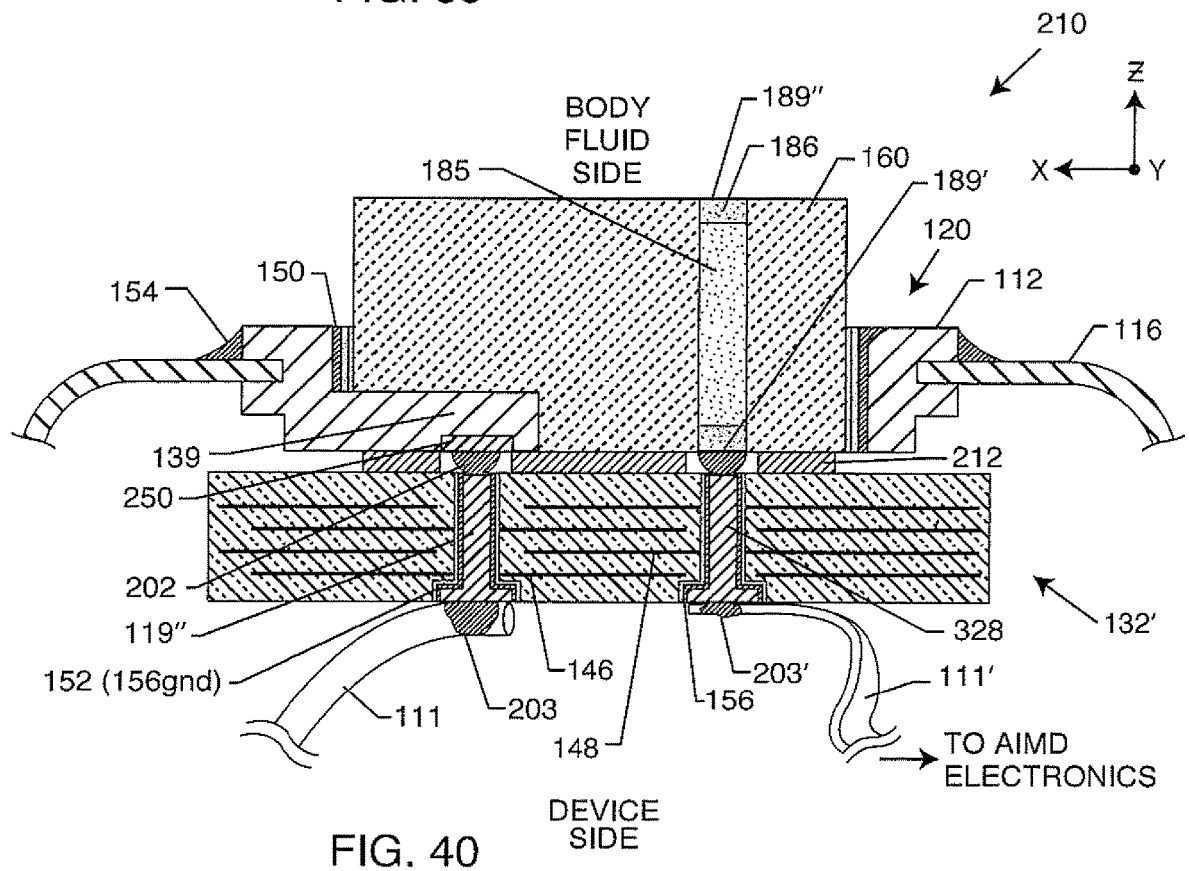
FIG. 40 is a sectional view similar to FIG. 39 now having an internally ground capacitor placed thereon.

FIG. 26C is very similar to FIGS. 26A and 26B and is taken generally from section 26C-26C from FIG. 26. In this case, the sectioning is through ground pin 111gnd. In this embodiment, instead of a ferrule peninsula, there is a ferrule bridge, as now illustrated. Referring back to FIG. 26, the bridge concept for an internal ground pin is illustrated in FIG. 40 of U.S. Pat. No. 6,765,780, the contents of which are incorporated herein fully be reference.

Figure 26D:
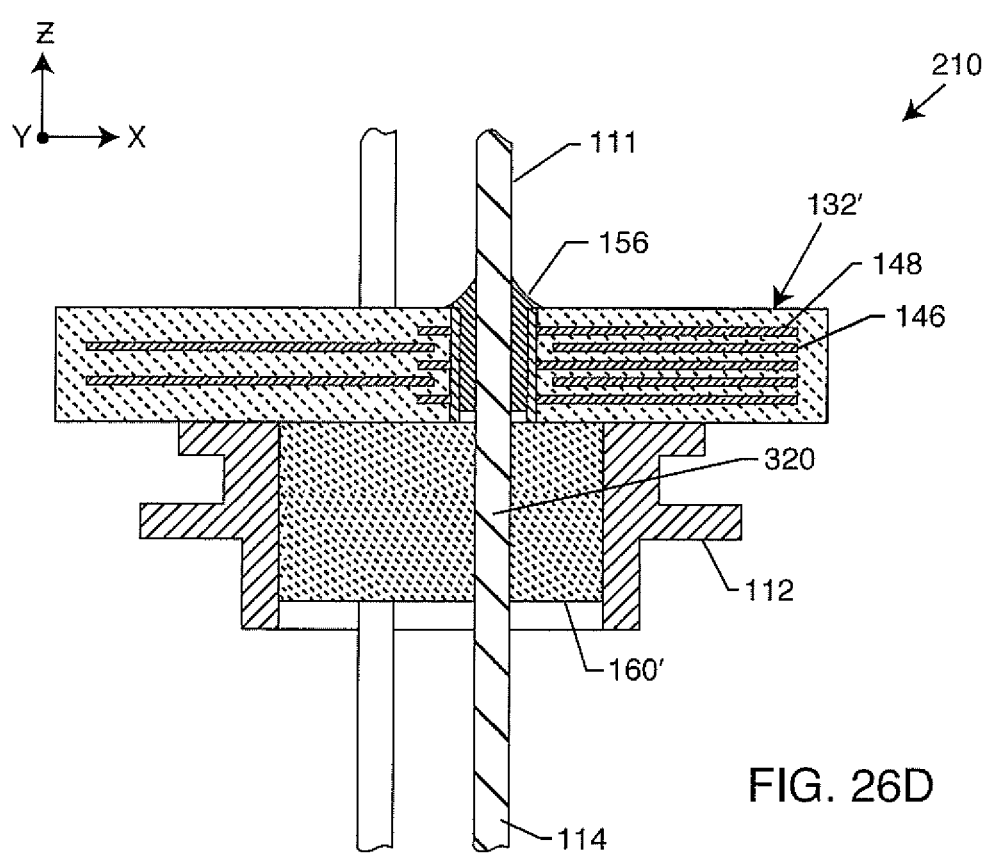
FIG. 26D is an isometric view taken along lines 26D-26D from FIG. 26.

FIG. 26D is taken from section 26D-26D from FIG. 26 and illustrates an active pin and an insulator 160' that is either a fusion glass, a compression glass or a glass ceramic. In this case, there is no need for a gold braze between the ferrule and the insulator.

Figure 27:
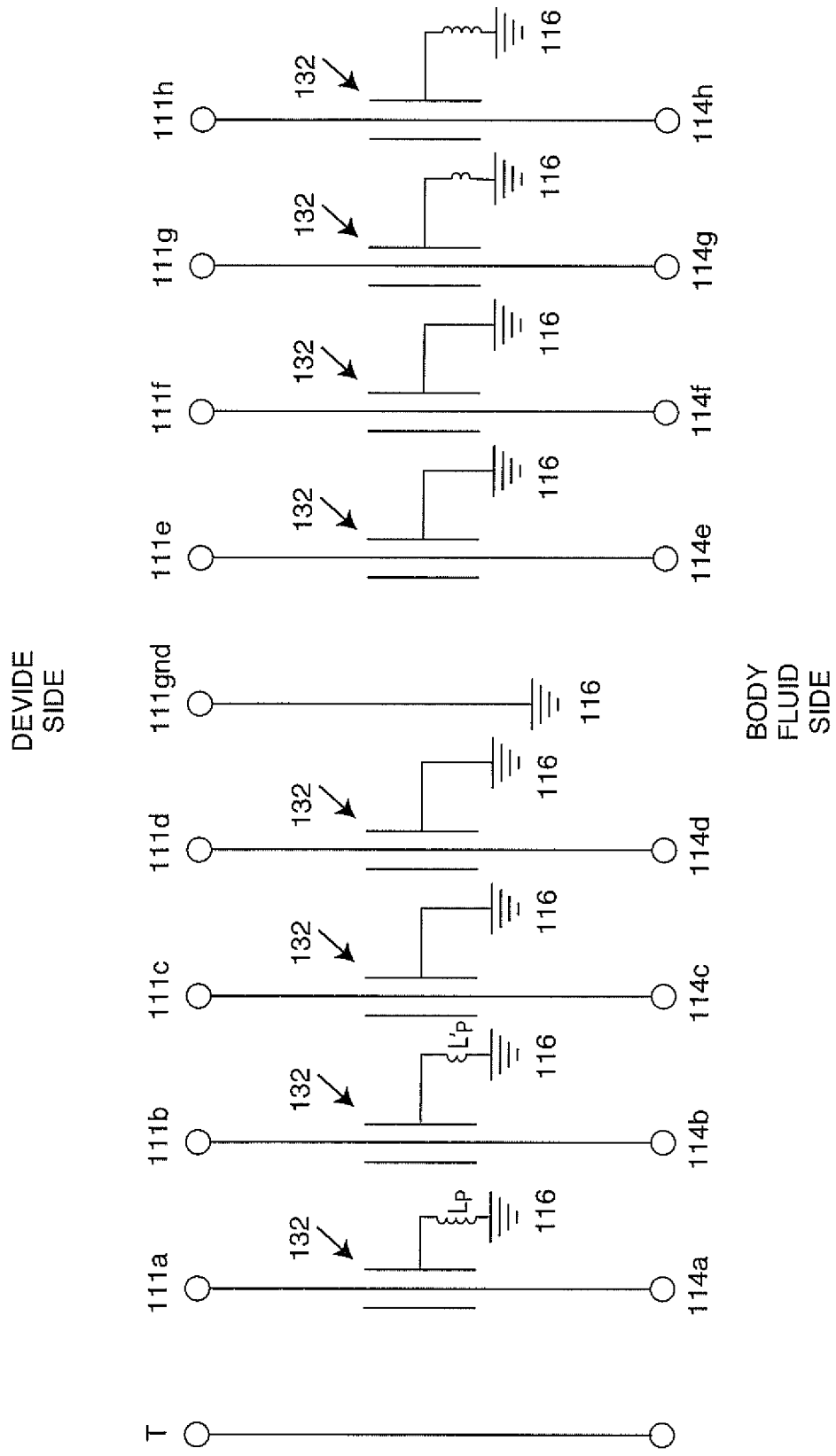
FIG. 27 is an electrical schematic of the structure of FIG. 26.

FIG. 27 is an electrical schematic diagram of the feedthrough capacitor filter of FIG. 26, which illustrates that the ground pin 111gnd only extends to the device side (not to the body fluid side). Active pins 111a through 111h are illustrated, each associated with its own individual feedthrough capacitor. In addition, a telemetry pin T is illustrated, which cannot be filtered. If the telemetry pin were filtered, then it would not be possible to transmit RF telemetry signals back and forth from the device.

Figure 29:
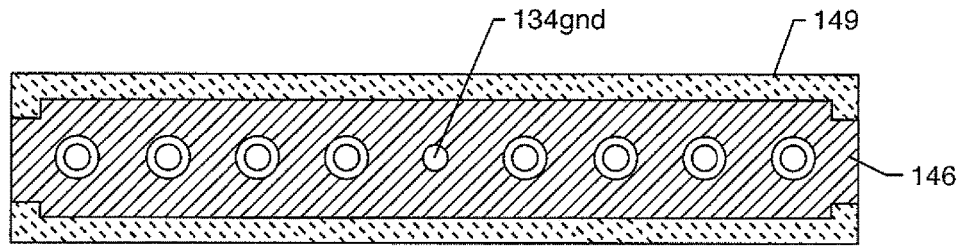
FIG. 29 is a sectional view of a ground electrode plate taken along lines 29-29 of FIG. 28.
Figure 30:
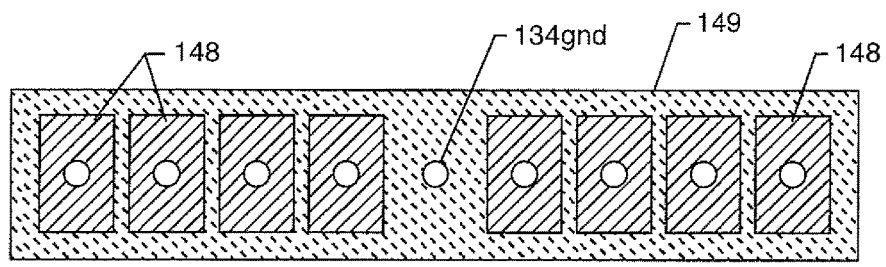
FIG. 30 is a sectional view of a ground electrode plate taken along lines 30-30 of FIG. 28.

FIG. 28 illustrates a hybrid feedthrough capacitor, which is best understood by looking at its ground electrode plates in FIG. 29 and its active electrode plates in FIG. 30. Ground electrode plate in FIG. 28, which is taken from section 29-29 from FIG. 28. This illustrates a ground electrode that is grounded to a center hole 111gnd and also at its ends, as illustrated. The ends of the capacitor ground electrodes are terminated in capacitor metallization 142. There are eight active electrodes forming eight different capacitors, as illustrated in FIG. 30. FIG. 30 is taken generally from section 30-30 from FIG. 28. The active electrodes 148 are all the same size, which would mean that all of the capacitances were of equal value. It is known to those skilled in the art to vary the active areas if different capacitance were required.

FIG. 31 illustrates a hermetic seal terminal subassembly 120 that has been prepared for mounting of the feedthrough capacitor of FIG. 28. One can see a center ground pin 111gnd, which is either laser welded to gold braze 150' to the ferrule structure 112. In addition, there are gold pad pockets 248, 250. On the left-hand side, these are shown as two discrete pockets and on the right-hand side, this is shown as one continuous pocket. The feedthrough capacitor 132 of FIG. 28 is defined herein as a hybrid internally grounded capacitor, in that, it has both an internal ground passageway and also grounded end metallizations. Hybrid capacitors are taught by U.S. Pat. No. 6,765,780, the contents of which is fully incorporated herein with this reference.

Referring back to FIG. 31, the gold pockets 250 are optional, in that, if the capacitor was made shorter, an electrical contact 152 could be made to the gold braze 150 of the hermetic seal. However, as illustrated, the gold pockets allow the capacitor to be a little longer and extend over complex ferrule areas, including ferrule capture areas 163. These multipart pins are taught by U.S. patent Ser. Nos. 15/844,683 and 15/603,521, the contents of which are incorporated herein fully be reference.

FIG. 32 illustrates the hybrid capacitor 132 of FIG. 28 mounted to the feedthrough hermetic seal subassembly 120 of FIG. 31. In accordance with the present invention and as illustrated in FIG. 32, the width of the feedthrough capacitor 268 overhangs the widest dimension of the ferrule 266. Also, in accordance with the present invention, the length of the feedthrough capacitor 272 is setback (it is shorter) from the overall length or the greatest length of the ferrule 270. Accordingly, the capacitor perimeter width surfaces 252 overhang the ferrule in accordance with the present invention.

Figure 33:
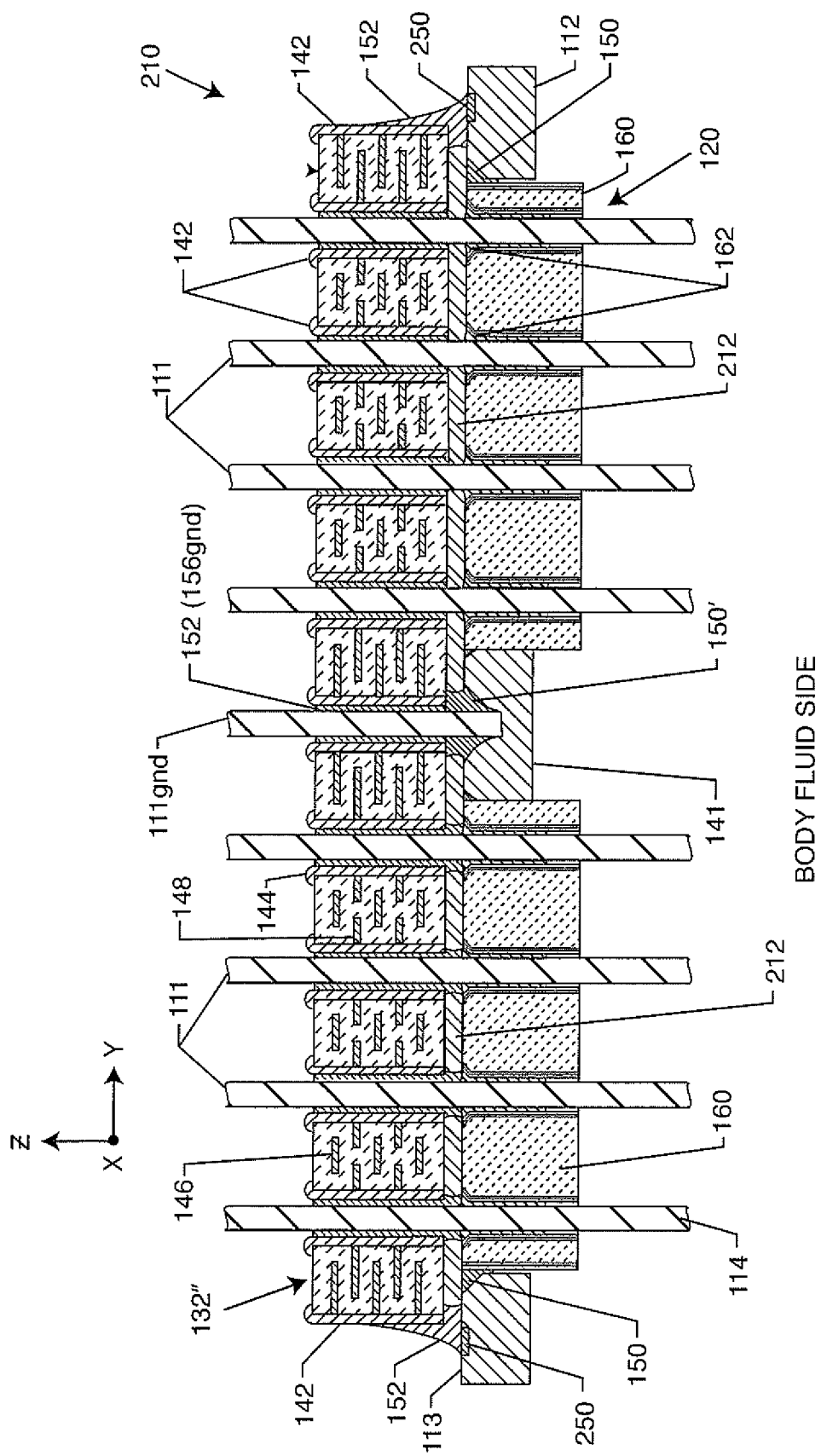
FIG. 33 is a sectional side view taken along lines 33-33 from FIG. 32.

FIG. 33 is taken from section 33-33 from FIG. 32 and shows the overhanging capacitor in sectional view. FIG. 33 is taken in the y-z plane and illustrates that the capacitor sets back (does not overhang) the widest dimensions of the ferrule 112. Referring once again to FIG. 33, one can clearly see the electrical connection 152 between the internally grounded hybrid feedthrough capacitor ground metallization 142 and gold pockets 250. In FIG. 33, one can also see ground pin 111gnd, which has been gold brazed 150' into ferrule bridge 141. This type of hybrid grounding, using both the end metallizations 142 and the ground pin 111gnd is very important, such that proper filter performance be maintained on every one of the active pins. This capacitor is too long to depend only on grounding by the centered pin 111gnd. Undue inductance and resistance could build up along the ground electrode plates, meaning that the furthest left and furthest right pins would have seriously degraded insertion loss (attenuation). In accordance with the hybrid concept, what results is a multi-point ground system, which means that each pin is an effective EMI filter. Hybrid internally grounded capacitors are taught by U.S. Pat. No. 6,765,780, the concepts of which are incorporated fully herein by reference.

Figure 34:
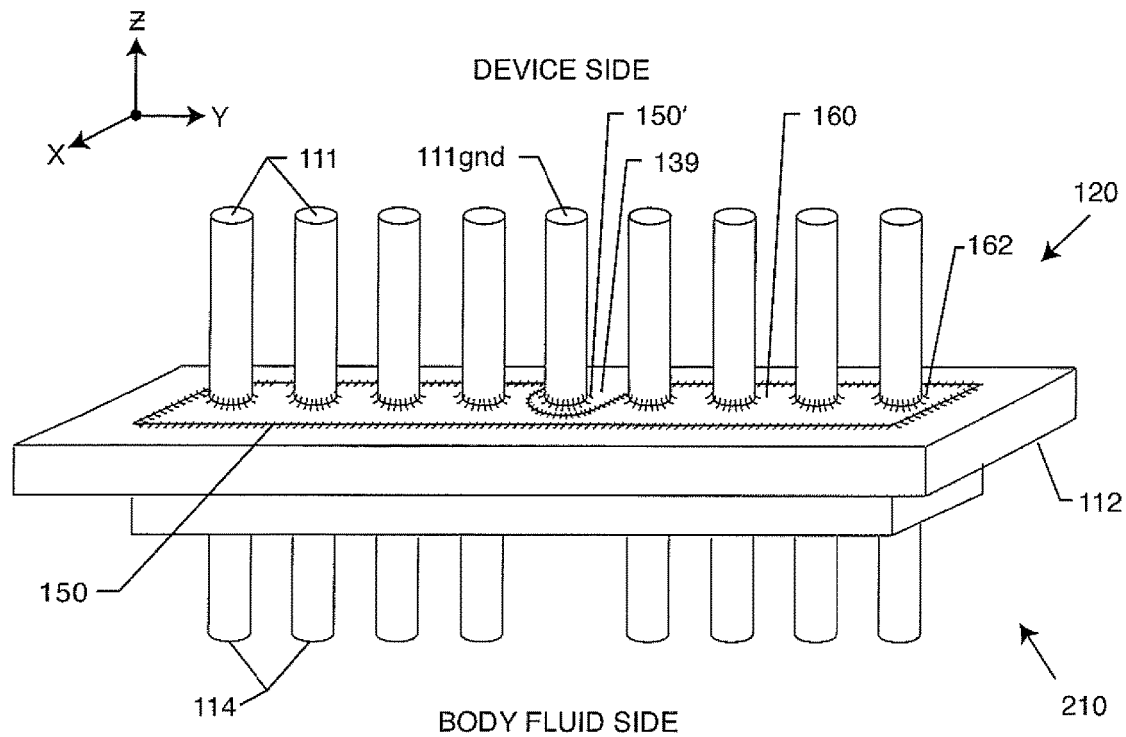
FIG. 34 illustrates an isometric view of a feedthrough assembly having a peninsula for an internal ground attachment and a gold pocket pad for an external ground attachment to use with the capacitor of the present invention.

Referring to FIG. 34, one will notice that the gold pockets 248, 250 have been eliminated. In this case, the capacitor length is aligned so that an electrical connection can be made from the capacitor ground metallization 142 directly to the gold braze of the hermetic seal between the insulator 160 and ferrule 112.

Figure 35:
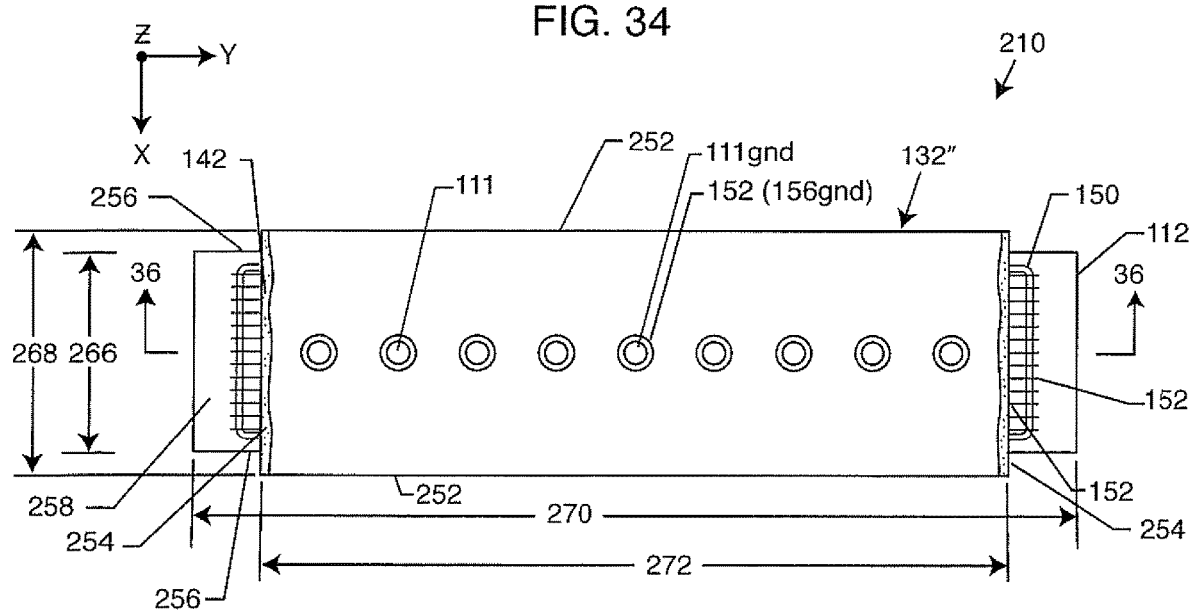
FIG. 35 is a top view of the structure of FIG. 34 taken along lines 35-35.

FIG. 35 is a top view of the capacitor mounted onto the hermetic terminal subassembly of FIG. 34. In accordance with the present invention, one can see that the overall length 272 of the hybrid internally grounded feedthrough capacitor 132" is shorter (has a setback) compared to the greatest overall length of the ferrule 270. Also, in accordance with the present invention is the hybrid internally grounded feedthrough capacitor 132" is wider in its width than the greatest width 266 of the ferrule 266. The greatest width 266 of the ferrule is also known as the furthermost width of the ferrule. As illustrated in FIG. 34, ferrules 112 often have irregular dimensions, so it is important that when we refer to capacitor overhang or capacitor setback, we are always referring to the greatest width or the greatest length of both an irregularly shaped ferrule and/or a regularly shaped (symmetrical) ferrule.

Figure 36:
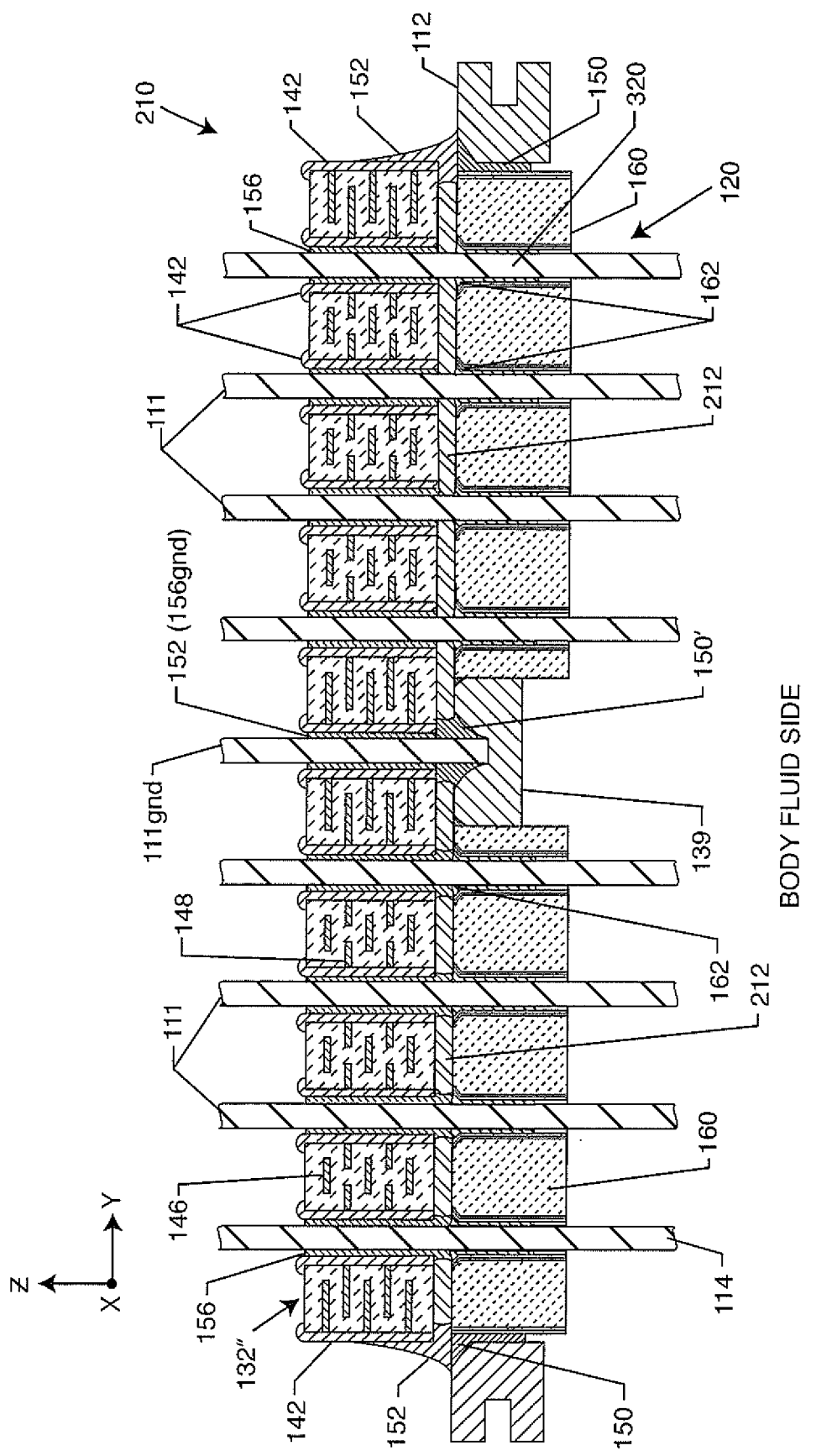
FIG. 36 is a sectional side view taken along lines 36-36 from FIG. 34.

FIG. 36 is a cross-sectional view taken from section 36-36 from FIG. 35. This illustrates the centered ground pin 111*gnd* which has been gold brazed or laser welded 150' into the ferrule peninsula structure 139. The hybrid ground connections are also shown in the capacitor ground terminations 142 are shown electrically connected 152 to ferrule gold braze 150. As previously described, this multi-point grounding system assures a high level of filtering performance for each of the active pins.

Figure 37:
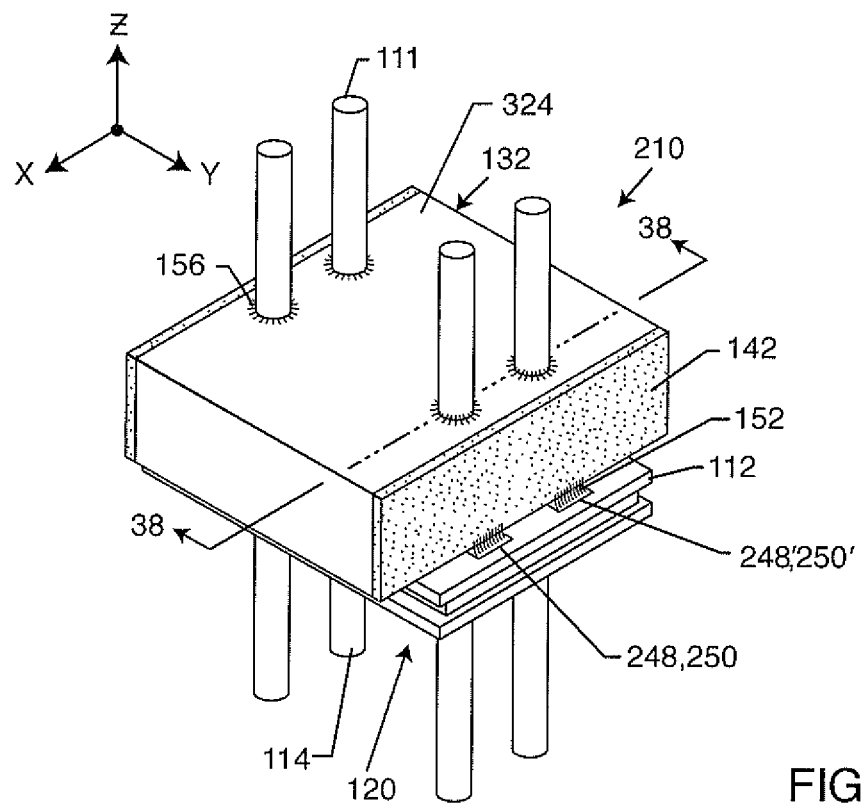
FIG. 37 is an isometric view of another embodiment of the present invention now having a leadwire comprised of different materials.
Figure 38:
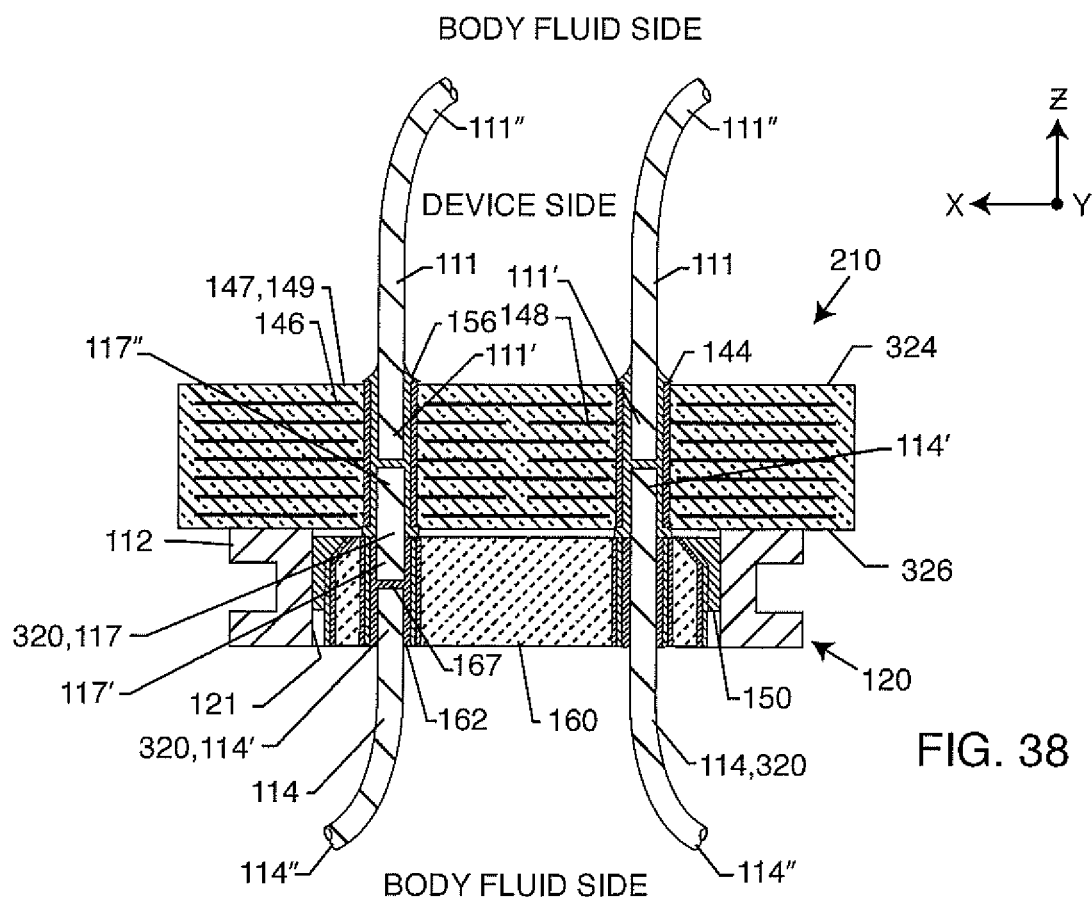
FIG. 38 is a sectional side view taken along lines 38-38 from FIG. 37.

FIG. 37 is a quadpolar capacitor somewhat similar to that illustrated in FIGS. 21 and 22. As illustrated, it has an overhang and also a setback in accordance with the present invention. Another distinguishing feature is revealed in FIG. 38, which is taken from section 38-38 from FIG. 37. On the left-hand side of the sectional view, one can see that the device side leadwire 111 has been segmented (complete wire segment 117). Leadwire segment 117 has been co-brazed along with body fluid side lead 114'. This is defined herein as a two-part pin. The right-hand side of FIG. 38 illustrates that the body fluid side pin 114 extends all the way through the hermetic insulator and half way through the feedthrough capacitor. In both the left and right-hand side embodiments, there is a low-cost pin 111, which is typically of tin copper, which is co-joined and soldered approximately half way through the feedthrough capacitor. This type of two-part or three-part pin construction greatly reduces cost because in the prior art, it was typical to take non-toxic and biocompatible leadwires, such as platinum or palladium leadwires and run them all the way through the structure. There is no need on the device side to have biocompatible materials.

Referring back to FIG. 38, on the left-hand side, we have a co-brazed pin, which is further described by U.S. patent application Ser. No. 15/603,521, the contents of which are incorporated herein fully by reference. On the right-hand side of FIG. 41, we have a two-part pin co-joined in the feedthrough capacitor that is described by U.S. patent application Ser. No. 15/844,683, the contents of which are also fully incorporated herein by reference.

Figure 38A:
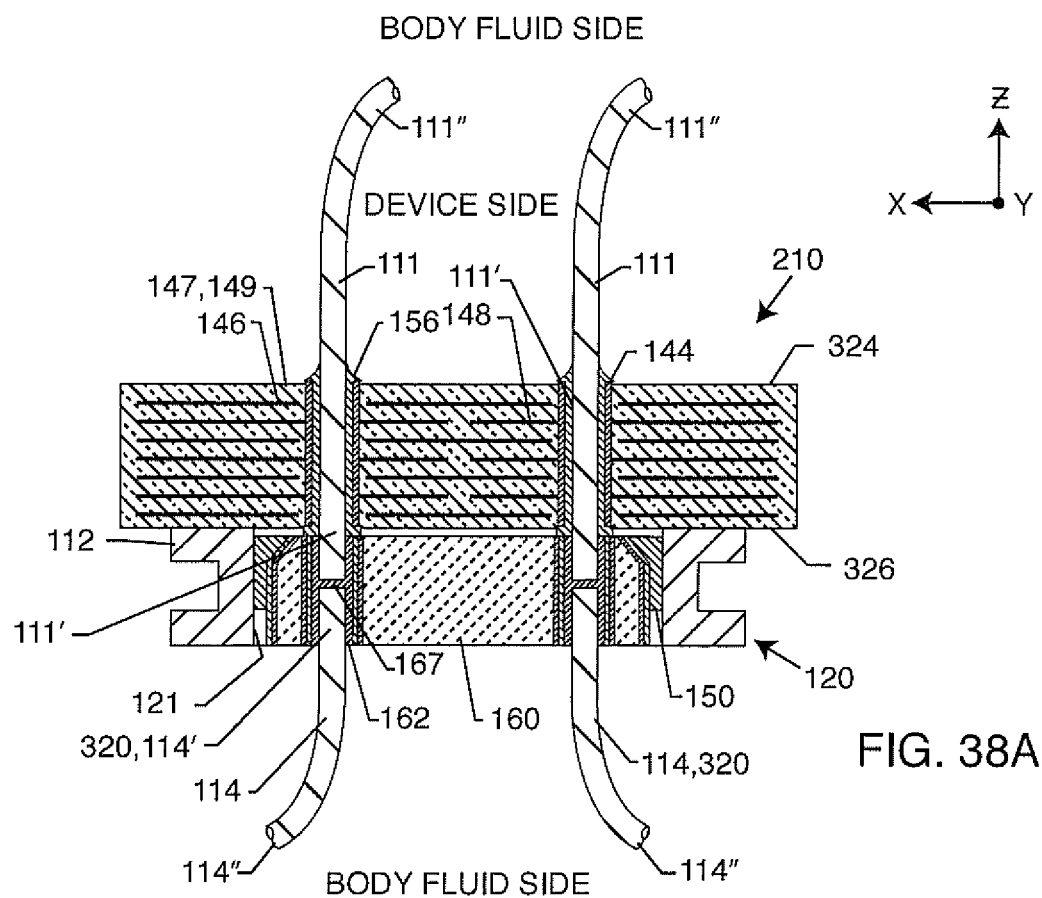
FIG. 38A is similar to FIG. 38 but is another embodiment of a leadwire comprised of different materials.

FIG. 38A is substantially the same as FIG. 38, except in this case, the two-part lead connection is disposed inside the inside insulator passageway, as illustrated. In this case, the two-part lead 111', 114 is joined by co-brazing the leads. Two-part pins, as illustrated in FIG. 38A, are more thoroughly described in U.S. Patent Pub. No. 2018/0126175 (application Ser. No. 15/603,521), the contents of which are herein incorporated by reference.

Figure 39:
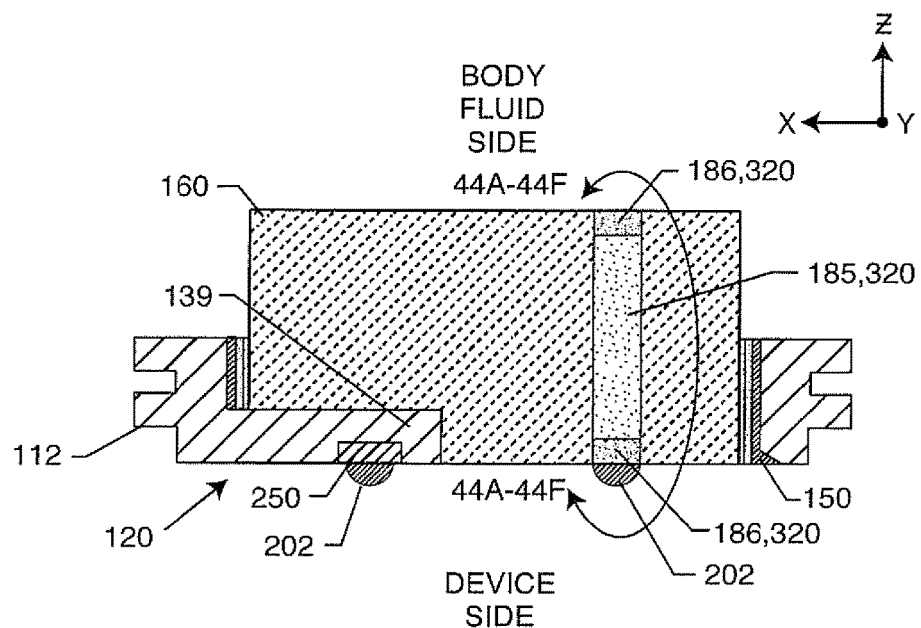
FIG. 39 is a sectional view of a feedthrough having a peninsula with a gold pocket pad for an internally ground capacitor.

FIG. 39 illustrates a cross-section of a hermetic terminal subassembly with a peninsula with a gold pocket. It also illustrates that instead of a leadwire pin, a conductive pathway passes through the insulator. In this case, the conductive pathway consists of a ceramic reinforced metal composite material 185 with pure platinum end caps 186. Referring to FIGS. 39-45, composite reinforced metal ceramic (CRMC) co-sintered vias are more fully described in U.S. patent application Ser. No. 15/863,194, the contents of which are incorporated herein fully be reference. CRMC vias are also described in U.S. Pat. Nos. 8,653,384; 8,938,309; 9,233,253; 9,352,150; 9,492,659; and 9,889,306, the contents of which are incorporated herein by reference.

FIG. 40 illustrates an internally grounded feedthrough capacitor 132' of the present invention mounted to the hermetic terminal and substantially overhanging the ferrule 112. This overhang is in the x-z axis. Not shown is the sectional view from the side showing the length of the feedthrough capacitor and the length of the ferrule, but it will be appreciated that the capacitor does not overhang in the y-z axis, but it is either setback or aligned with the ferrule edge as has been previously described.

Figure 41:
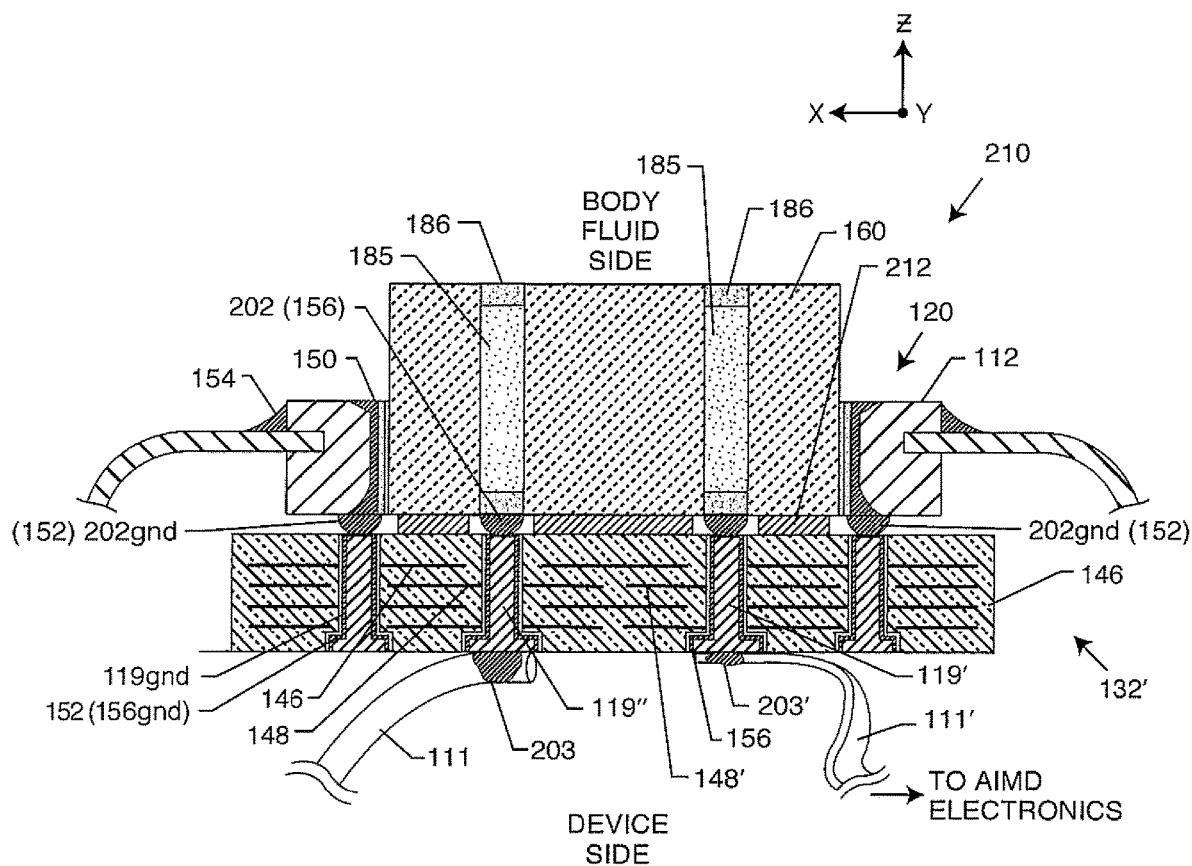
FIG. 41 is a sectional view similar to FIG. 40 now showing an internally grounded capacitor grounded the oxide-resistant gold braze hermetic seal.

FIG. 41 is substantially the same as FIG. 40, except in this case instead of gold pockets, the ground electrical connections from the two ground pins 119*gnd* are directly to the hermetic seal gold braze 150 by way of 202*gnd*, which can be a solder, a thermal-setting conductive adhesive, ACF film or the like. Again, in accordance with the present invention, the feedthrough capacitor 132' overhangs the ferrule in the x-z plane.

Figure 42:
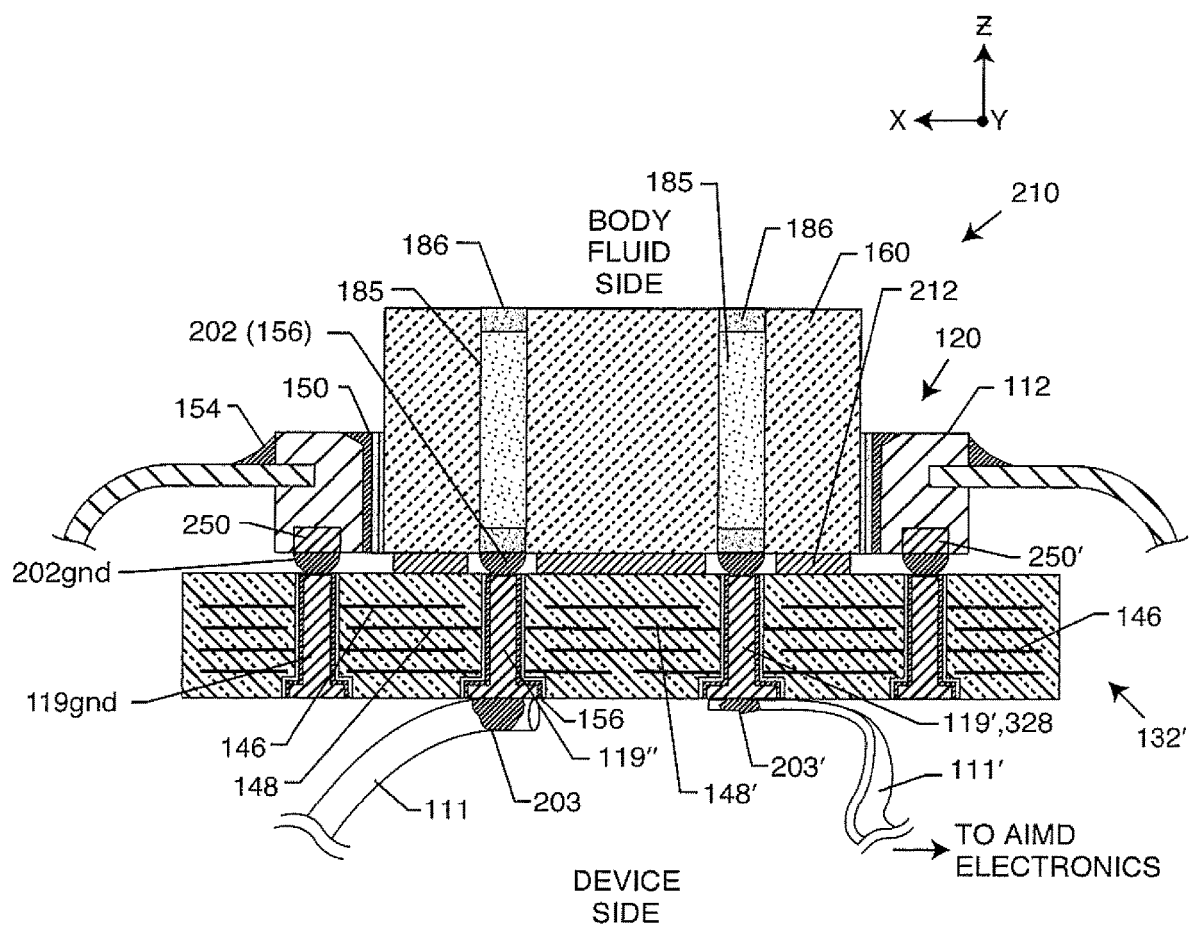
FIG. 42 illustrates a sectional side view of another embodiment of the present invention similar to FIG. 41 now having an internally grounded capacitor that is ground to a gold pocket pad along the ferrule perimeter.

FIG. 42 is similar to FIG. 40 illustrating the present invention with an internally grounded feedthrough capacitor 132' along with multiple connections to gold pockets 250 and 250' In accordance with the present invention, the internally grounded feedthrough capacitor 132 overhangs the widest width of the ferrule 112 in the x-z plane.

Figure 43:
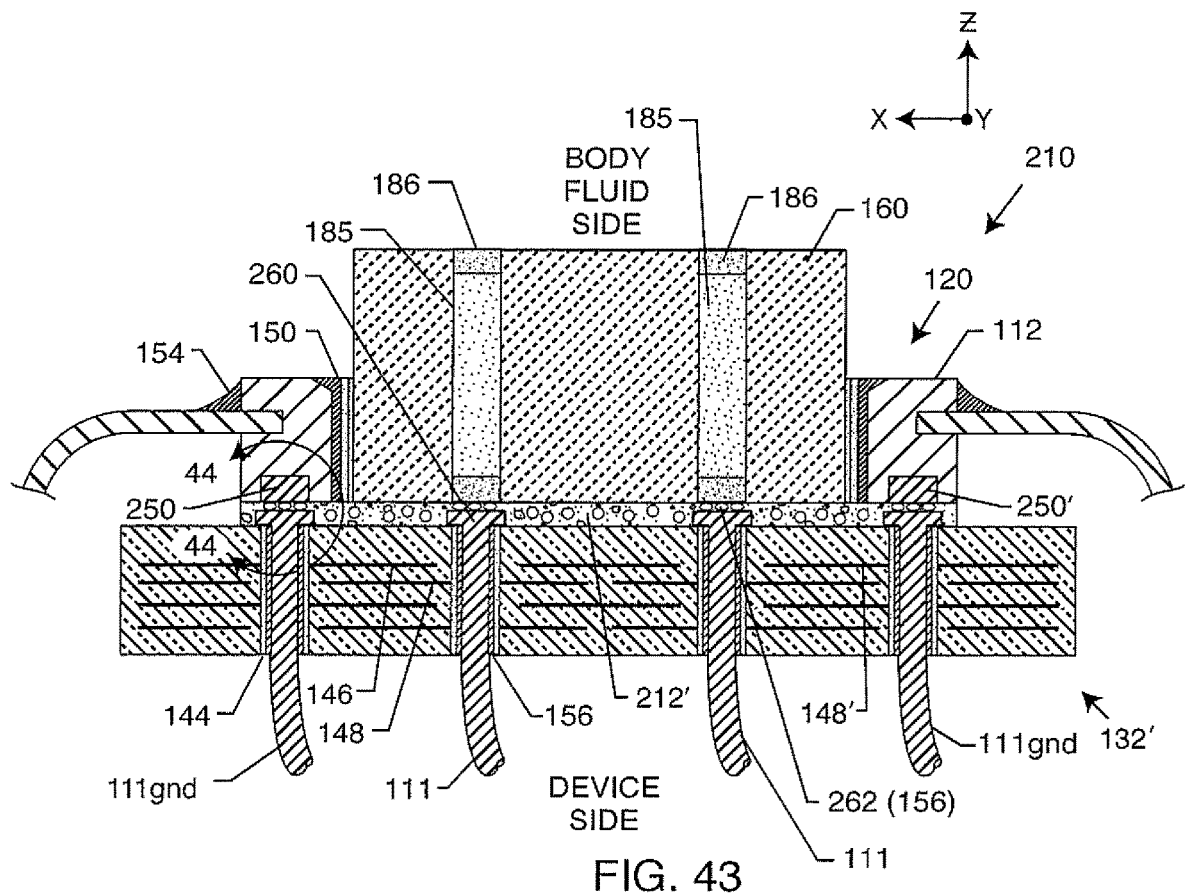
FIG. 43 is very similar to FIG. 42 but now uses an ACF film for making electrical connections.

FIG. 43 is very similar to FIGS. 41 and 42, except that in this case, ACF films are used to make the electrical connection 260 and a nail-headed ground leadwire 111*gnd*, as illustrated. It will be appreciated that in addition to ACF films, BGA solder bumps or BGA thermal-setting epoxy bumps could also be used.

Figure 44:
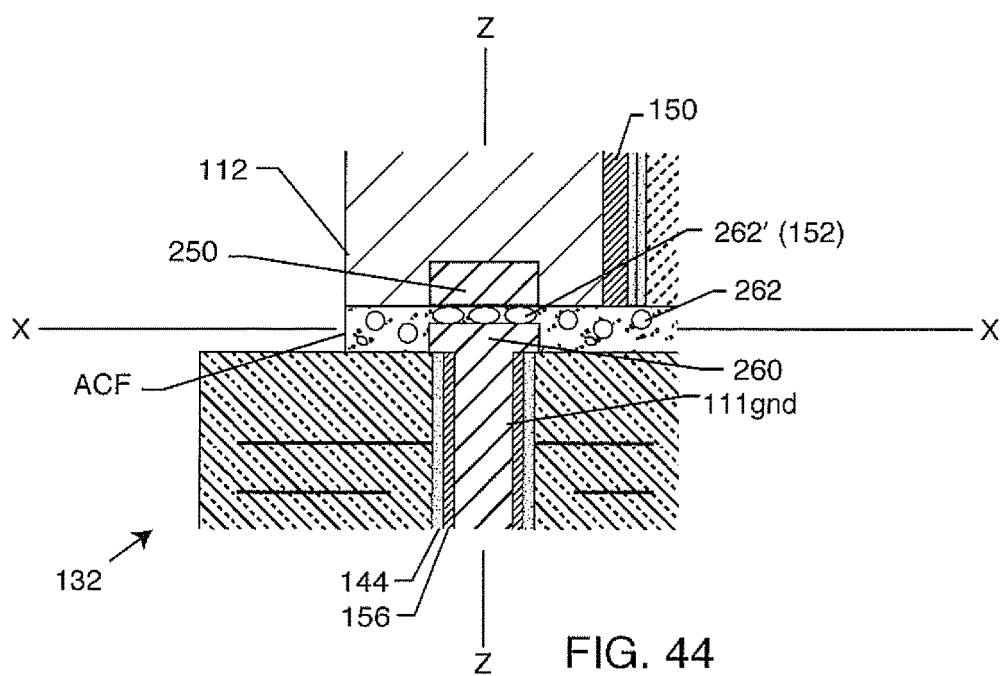
FIG. 44 is an enlarged view taken along lines 44-44 of FIG. 43.

FIG. 44 is a close-up taken from section 44-44 from FIG. 43 illustrating compression of the ACF film conductive particles 262' in the electrical connection area. The freely suspended particles 262 are insulated from each other providing conductivity only on the area of the nail head 111*gnd* nail head 260 and gold pocket area 250 of ferrule 112.

What is claimed is:

1. A filter feedthrough that is attachable to an active implantable medical device (AIMD), the filter feedthrough comprising:
    a) a feedthrough, comprising:
        i) an electrically conductive ferrule comprising a ferrule sidewall extending to a ferrule body fluid side end surface and a ferrule device side end surface, the ferrule sidewall further comprising a ferrule outermost surface and a ferrule inner surface defining a ferrule opening extending to the ferrule body fluid and device side end surfaces;
        ii) an insulator at least partially residing in the ferrule opening where the insulator is hermetically sealed to the ferrule, the insulator extending to an insulator body fluid side end surface and an insulator device side end surface, wherein, when the ferrule hermetically sealed to the insulator is attached to an opening in a housing of an AIMD, the ferrule and insulator body fluid side end surfaces and the ferrule and insulator device side end surfaces reside outside and inside the AIMD, respectively;
        iii) at least one active via hole extending through the insulator to the insulator body fluid and device side end surfaces; and
        iv) an active conductive pathway at least partially residing in and hermetically sealed to the insulator in the at least one active via hole; and b) a feedthrough capacitor disposed on or near the ferrule device side end surface or the insulator device side end surface, the feedthrough capacitor comprising:
   i) a capacitor dielectric having a capacitor dielectric outer sidewall extending to a capacitor dielectric first end surface and a capacitor dielectric second end surface;
   ii) at least one active electrode plate interleaved in a capacitive relationship with at least one ground electrode plate in the capacitor dielectric;
   iii) at least one active passageway extending through the capacitor dielectric to the capacitor dielectric first and second end surfaces;
   iv) a capacitor active metallization contacting the capacitor dielectric in the at least one active passageway and being electrically connected to the at least one active electrode plate; and
   v) a capacitor ground metallization electrically connected to the at least one ground electrode plate; and
c) a first electrical connection material electrically connecting the active conductive pathway residing in the at least one active via hole in the insulator to the capacitor active metallization electrically connected to the at least one active electrode plate of the feedthrough capacitor; and
d) a second electrical connection material electrically connecting the capacitor ground metallization electrically connected to the at least one ground electrode plate of the feedthrough capacitor to the ferrule,
e) wherein an imaginary projection aligned with the ferrule outermost surface and projected toward the capacitor dielectric second end surface defines:
   A) at least one capacitor dielectric first overhang portion extending laterally outwardly beyond the imaginary projection of the ferrule outermost surface; and
   B) a capacitor dielectric second overlay portion that is defined by the imaginary projection aligned with the ferrule outermost surface and overlays the ferrule and insulator device side end surfaces,
   C) wherein at least part of the capacitor dielectric outer sidewall in the capacitor dielectric second overlay portion is spaced inwardly from the imaginary projection aligned with the ferrule outermost surface, and wherein the at least one ground electrode plate at least partially resides in the capacitor dielectric second overlay portion.

2. The filter feedthrough of claim 1, wherein at least a portion of the capacitor ground metallization contacts the capacitor outer sidewall in the capacitor dielectric second overlay portion and is electrically connected to the ferrule by the second electrical connection material.

3. The filter feedthrough of claim 1, wherein the second electrical connection material electrically connects the capacitor ground metallization electrically connected to the at least one ground electrode plate of the feedthrough capacitor to at least one of the ferrule and a first gold braze hermetically sealing the insulator to the ferrule.

4. The filter feedthrough of claim 3, wherein:
a) the ferrule device side end surface is provided with at least one recessed pocket residing adjacent to the outer sidewall of the capacitor dielectric second overlay portion, the recessed pocket having a gold pocket-pad nested therein and being electrically connected to the ferrule, and
b) the second electrical connection material electrically connects the capacitor ground metallization electrically connected to the at least one ground electrode plate at least partially residing in the capacitor dielectric second overlay portion to the gold pocket-pad.

5. The filter feedthrough of claim 1, wherein:
a) the ferrule outermost surface comprises opposed ferrule first and second outermost surface portions meeting opposed ferrule third and fourth outermost surface portions and wherein respective ferrule first, second, third and fourth imaginary projections are aligned with the ferrule first, second, third and fourth outermost surface portions; and
b) the capacitor dielectric outer sidewall comprises opposed capacitor dielectric first and second outer sidewall portions meeting opposed capacitor dielectric third and fourth outer sidewall portions,
c) wherein imaginary projections aligned with the ferrule first, second, third and fourth outermost surface portions and projected toward the capacitor dielectric second end surface provide the ferrule first and second outermost surface portions intersecting the capacitor dielectric third and fourth outer sidewall portions to thereby provide:
   A) the capacitor dielectric first overhang portion comprising the capacitor dielectric first outer sidewall portion extending laterally outwardly beyond the imaginary projection aligned with the ferrule first outermost surface portion;
   B) the capacitor dielectric second overlay portion defined by the imaginary projections aligned with the ferrule first and second outermost surface portions and overlaying the ferrule and insulator device side end surfaces; and
   C) a capacitor dielectric third overhang portion comprising the capacitor dielectric second outer sidewall portion extending laterally outwardly beyond the imaginary projection of the ferrule second outermost surface portion, and
d) wherein the imaginary projections aligned with the ferrule third and fourth outermost surface portions do not intersect the respective capacitor dielectric third and fourth outer sidewall portions to thereby expose portions of the ferrule device side end surface adjacent to the capacitor dielectric third and fourth outer sidewall portions.

6. The filter feedthrough of claim 5,
wherein the ferrule first, second, third and fourth outermost surface portions are respective ferrule first, second, third and fourth planar outermost surface portions, and wherein the ferrule first and second planar outermost surface portions are longer than the ferrule third and fourth planar outermost surface portions to thereby provide the ferrule having a first rectangular shape in plan-view, and
wherein the capacitor dielectric first, second, third and fourth outer sidewall portions are respective capacitor dielectric first, second, third and fourth planar outer sidewall portions, and wherein the capacitor first and second planar outer sidewall portions are longer than the capacitor dielectric third and fourth planar outer sidewall portions to thereby provide the capacitor dielectric having a second rectangular shape in plan-view.

7. The filter feedthrough of claim 5, wherein the capacitor ground metallization contacts at least one of the capacitor dielectric third and fourth outer sidewall portions, and wherein the second electrical connection material electrically connects the capacitor ground metallization to the ferrule device side end surface, spaced inwardly from a corresponding one of at least one of the ferrule third and fourth outermost surface portions.

8. The filter feedthrough of claim 7, wherein the ferrule device side end surface is provided with at least one recessed pocket residing adjacent to at least one of the ferrule third and fourth outermost surface portions, the recessed pocket having a gold pocket-pad nested therein and being electrically connected to the ferrule, and wherein the capacitor ground metallization contacts at least one of the capacitor dielectric third and fourth outer sidewall portions with the second electrical connection material electrically connecting the capacitor ground metallization to the gold pocket-pad.

9. The filter feedthrough of claim 1, wherein:
 a) the ferrule outermost surface comprises opposed ferrule first and second outermost surface portions meeting opposed ferrule third and fourth outermost surface portions, and wherein respective ferrule first, second, third and fourth imaginary projections are aligned with the ferrule first, second, third and fourth outermost surface portions, the ferrule first and second outermost surface portions being planar and the ferrule third and fourth outermost surface portions having a radiused shape to thereby provide the ferrule having a first oval shape in plan-view; and
 b) the capacitor dielectric outer sidewall comprises opposed capacitor dielectric first and second outer sidewall portions meeting opposed capacitor dielectric third and fourth outer sidewall portions, the capacitor dielectric first and second outer sidewall portions being planar and the capacitor dielectric third and fourth outer sidewall portions having a radiused shape to thereby provide the capacitor dielectric having a second oval shape in plan-view,
 c) wherein imaginary projections aligned with the ferrule first, second, third and fourth outermost surface portions and projected toward the capacitor dielectric second end surface provide the ferrule first and second outermost surface portions intersecting the capacitor dielectric third and fourth outer sidewall portions to thereby provide:
  A) the capacitor dielectric first overhang portion comprising the capacitor dielectric first outer sidewall portion extending laterally outwardly beyond the imaginary projection of the ferrule first planar outermost surface portion;
  B) the capacitor dielectric second overlay portion defined by the imaginary projections aligned with the ferrule first and second planar outermost surface portions overlaying the ferrule and insulator device side end surfaces; and
  C) a capacitor dielectric third overhang portion comprising the capacitor dielectric second outer sidewall portion extending laterally outwardly beyond the imaginary projection of the ferrule second planar outermost surface portion, and
 d) wherein the imaginary projections aligned with the ferrule third and fourth radiused outermost surface portions do not intersect the respective capacitor dielectric third and fourth outer sidewall portions to thereby expose portions of the ferrule device side end surface adjacent to the capacitor dielectric third and fourth outer sidewall portions.

10. The filter feedthrough of claim 9, wherein the capacitor ground metallization contacts at least one of the capacitor dielectric third and fourth outer sidewall portions, and wherein the second electrical connection material electrically connects the capacitor ground metallization to the ferrule device side end surface, spaced inwardly from at least one of the ferrule third and fourth outermost surface portions.

11. The filter feedthrough of claim 10, wherein the ferrule device side end surface is provided with at least one recessed pocket residing adjacent to at least one of the ferrule third and fourth outermost surface portions, the recessed pocket having a gold pocket-pad nested therein and being electrically connected to the ferrule, and wherein the capacitor ground metallization contacts at least one of the capacitor dielectric third and fourth outer sidewall portions with the second electrical connection material electrically connecting the capacitor ground metallization to the gold pocket-pad.

12. The filter feedthrough of claim 1, further comprising:
 a) at least one ground passageway extending through the capacitor dielectric to the capacitor dielectric first and second end surfaces, the capacitor ground metallization residing in the ground passageway and being electrically connected to the at least one ground electrode plate;
 b) a peninsula extending from the ferrule inner surface inwardly into the ferrule opening, wherein the second electrical connection material electrically connects the capacitor ground metallization electrically connected to the at least one ground electrode plate of the feedthrough filter to the ferrule peninsula, and
 c) wherein the ferrule outermost surface comprises opposed ferrule first and second outermost surface portions meeting opposed ferrule third and fourth outermost surface portions; and
 d) the capacitor dielectric outer sidewall comprises opposed capacitor dielectric first and second outer sidewall portions meeting opposed capacitor dielectric third and fourth outer sidewall portions,
 e) wherein the imaginary projection aligned with the ferrule outermost surface and projected toward the capacitor dielectric second end surface provides:
  A) the ferrule first and second outermost surface portions intersecting the capacitor dielectric third and fourth outer sidewall portions to thereby provide the capacitor dielectric first overhang portion comprising the capacitor dielectric first outer sidewall portion extending laterally outwardly beyond the imaginary projection of the ferrule first outermost surface portion;
  B) the capacitor dielectric second overlay portion defined by the imaginary projections aligned with the ferrule first and second outermost surface portions and overlaying the ferrule and insulator device side end surfaces; and
  C) a capacitor dielectric third overhang portion comprising the capacitor dielectric second outer sidewall portion extending laterally outwardly beyond the imaginary projection of the ferrule second outermost surface portion, and
 f) wherein the imaginary projections aligned with the ferrule third and fourth outermost surface portions do not intersect the respective capacitor dielectric third and fourth outer sidewall portions to thereby expose portions of the ferrule device side end surface adjacent to the capacitor dielectric third and fourth outer sidewall portions, and
 g) wherein the capacitor ground metallization also contacts the capacitor dielectric third and fourth outer sidewall portions, and wherein the second electrical connection material also electrically connects the capacitor ground metallization to the ferrule device side end surface, spaced inwardly from the ferrule third and fourth outermost surface portions.

13. The filter feedthrough of claim 12, wherein the ferrule first and second outermost surface portions are longer than the ferrule third and fourth outermost surface portions, and the capacitor dielectric first and second outer sidewall portions are longer than the capacitor dielectric third and fourth outer sidewall portions.

14. The filter feedthrough of claim 1, wherein the active conductive pathway in the insulator comprises a metallic leadwire residing in the at least one active via hole where a gold braze hermetically seals the leadwire to the insulator.

15. The filter feedthrough of claim 14, wherein the leadwire extends to a leadwire body fluid side portion extending outwardly beyond the insulator body fluid side end surface and a leadwire device side portion extending outwardly beyond the insulator device side end surface, the leadwire device side portion residing in the at least one active passageway in the capacitor dielectric where the leadwire is electrically connected to the at least one active electrode plate of the feedthrough capacitor.

16. The filter feedthrough of claim 1, wherein the at least one active via hole in the insulator is defined by an active via hole inner surface extending along a longitudinal axis to the insulator body fluid and device side end surfaces, and wherein the active conductive pathway residing in the at least one active via hole comprises:
   a) a layer of a ceramic reinforced metal composite (CRMC) comprising a mixture of alumina and platinum that contacts the active via hole inner surface, the layer of CRMC extending from a CRMC first end residing at or adjacent to the insulator device side end surface to a CRMC second end residing at or adjacent to the insulator body fluid side end surface, wherein an inner surface of the CRMC is spaced toward the longitudinal axis with respect to the via hole inner surface; and
   b) a substantially pure platinum material that contacts the CRMC inner surface, the substantially pure platinum material extending from a substantially pure platinum material first end residing at or adjacent to the insulator device side end surface to a substantially pure platinum material second end residing at or adjacent to the insulator body fluid side end surface.

17. The filter feedthrough of claim 16, wherein the CRMC first and second ends and the substantially pure platinum material first and second ends extend to the respective insulator body fluid and device side end surfaces.

18. The filter feedthrough of claim 16, wherein at least one of the CRMC first and second ends is recessed inwardly into the active via hole from the respective insulator body fluid and device side end surfaces, and wherein the substantially pure platinum material extends to the insulator body fluid and device side end surfaces.

19. The filter feedthrough of claim 16, wherein at least one of the CRMC first and second ends is recessed inwardly into the active via hole in the insulator from the respective insulator body fluid and device side end surfaces, and wherein a corresponding at least one of the substantially pure platinum material first and second ends is recessed inwardly into the active via hole from the respective insulator body fluid and device side end surfaces, and wherein a metallic end cap extends from the at least one recessed CRMC first and second end and the correspondingly recessed substantially pure platinum material first and second end to the corresponding insulator body fluid and device side end surface.

20. The filter feedthrough of claim 19, wherein the metallic end cap comprises platinum.

21. The filter feedthrough of claim 16, wherein the substantially pure platinum material is a platinum wire.

22. The filter feedthrough of claim 21, wherein the platinum wire is exposed at the insulator device side end surface.

23. The filter feedthrough of claim 16, wherein a platinum wire extends through the substantially pure platinum material to the insulator body fluid and device side end surfaces, the platinum wire being spaced from the layer of CRMC contacting the active via hole inner surface in the insulator.

24. A filter feedthrough that is attachable to an active implantable medical device (AIMD), the filter feedthrough comprising:
   a) a feedthrough, comprising:
      i) an electrically conductive ferrule comprising:
         A) a ferrule sidewall extending to a ferrule body fluid side end surface and a ferrule device side end surface, the ferrule sidewall further comprising a ferrule outermost surface and a ferrule inner surface defining a ferrule opening extending to the ferrule body fluid and device side end surfaces with a peninsula extending from the ferrule sidewall inwardly into the ferrule opening,
         B) wherein the ferrule outermost surface comprises opposed ferrule first and second outermost surface portions meeting opposed ferrule third and fourth outermost surface portions;
      ii) an insulator at least partially residing in the ferrule opening where the insulator is hermetically sealed to the ferrule, the insulator extending to an insulator body fluid side end surface and an insulator device side end surface located adjacent to the ferrule body fluid and device side end surfaces, respectively, wherein, when the ferrule hermetically sealed to the insulator is attached to an opening in a housing of an AIMD, the ferrule and insulator body fluid side end surfaces and the ferrule and insulator device side end surfaces reside outside and inside the AIMD, respectively;
      iii) at least one active via hole extending through the insulator to the insulator body fluid and device side end surfaces; and
      iv) an active conductive pathway at least partially residing in and hermetically sealed to the insulator in the at least one active via hole; and
   b) a feedthrough capacitor disposed on the device side of the ferrule, the feedthrough capacitor comprising:
      i) a capacitor dielectric having a capacitor dielectric outer sidewall extending to a capacitor dielectric first end surface and a capacitor dielectric second end surface, wherein the capacitor dielectric outer sidewall comprises opposed capacitor dielectric first and second outer sidewall portions meeting opposed capacitor dielectric third and fourth outer sidewall portions;
      ii) at least one active electrode plate interleaved in a capacitive relationship with at least one ground electrode plate in the capacitor dielectric;
      iii) at least one active passageway extending through the capacitor dielectric to the capacitor dielectric first and second end surfaces;
      iv) a capacitor active metallization contacting the capacitor dielectric in the at least one active passageway and being in an electrically conductive relation with the at least one active electrode plate;

v) at least one ground passageway extending through the capacitor dielectric to the capacitor dielectric first and second end surfaces;
vi) a capacitor ground metallization first portion contacting the capacitor dielectric outer sidewall and being in an electrically conductive relation with the at least one ground electrode plate; and
vii) a capacitor ground metallization second portion residing in the at least one ground passageway and being in an electrically conductive relation with the at least one ground electrode plate; and
c) a first electrical connection material electrically connecting the active conductive pathway residing in the at least one active via hole in the insulator to the active metallization electrically connected to the at least one active electrode plate of the feedthrough capacitor;
d) a second electrical connection material first portion electrically connecting the capacitor ground metallization first portion electrically connected to the at least one ground electrode plate at the capacitor dielectric outer sidewall to the ferrule, and a second electrical connection material second portion electrically connecting the capacitor ground metallization second portion electrically connected to the at least one ground electrode plate in the at least one ground passageway of the feedthrough capacitor to the ferrule peninsula;
e) wherein imaginary projections aligned with the ferrule outermost surface and projected toward the capacitor dielectric second end surface provide the ferrule first and second outermost surface portions intersecting the capacitor dielectric third and fourth outer sidewall portions to thereby define:
A) a capacitor dielectric first overhang portion comprising the capacitor dielectric first outer sidewall portion extending laterally outwardly beyond the imaginary projection of the ferrule first outermost surface portion;
B) a capacitor dielectric second overlay portion defined by the imaginary projections aligned with the ferrule first and second outermost surface portions and overlaying the ferrule and insulator device side end surfaces, wherein at least one of the capacitor dielectric third and fourth outer sidewall portions in the capacitor dielectric second overlay portion is spaced inwardly from the ferrule outermost surface, and wherein the at least one ground electrode plate at least partially resides in the capacitor dielectric second overlay portion; and
C) wherein the capacitor ground metallization first portion contacting at least one of the capacitor dielectric third and fourth outer sidewall portions in the capacitor dielectric second overlay portion is electrically connected to the ferrule device side end surface by the second electrical connection material first portion, spaced inwardly from a corresponding one of the at least one of the ferrule third and fourth outermost surface portions.

25. The filter feedthrough of claim 24, wherein the ferrule device side end surface is provided with at least one recessed pocket residing adjacent to at least one of the ferrule third and fourth outermost surface portions, the recessed pocket having a gold pocket-pad nested therein and being electrically connected to the ferrule, and wherein the second electrical connection material first portion contacting at least one of the capacitor dielectric third and fourth outer sidewall portions and being in an electrically conductive relation with the at least one ground electrode plate electrically connects the capacitor ground metallization first portion to the gold pocket-pad.

26. The filter feedthrough of claim 24, wherein a capacitor dielectric third overhang portion comprises the capacitor dielectric second outer sidewall portion extending laterally outwardly beyond the imaginary projection of the ferrule second outermost surface portion.

27. The filter feedthrough of claim 24, wherein the ferrule first and second outermost surface portions are longer than the ferrule third and fourth outermost surface portions, and wherein the capacitor dielectric first and second outer sidewall portions are longer than the capacitor dielectric third and fourth outer sidewall portions.

28. A filter feedthrough configured to be installed in an opening of a housing of an active implantable medical device (AIMD), the filter feedthrough comprising:
a) an electrically conductive ferrule comprising a ferrule sidewall defining a ferrule opening extending to a ferrule body fluid side opposite a ferrule device side;
b) an insulator hermetically sealing the ferrule opening, the insulator extending to an insulator body fluid side and an insulator device side, wherein, when the ferrule hermetically sealed to the insulator is attached to an opening in a housing of an AIMD, the ferrule and insulator body fluid sides and the ferrule and insulator device sides reside outside and inside the AIMD, respectively;
c) at least one conductive pathway hermetically sealed to and disposed through the insulator between the insulator body fluid and device sides, the at least one conductive pathway being in non-electrically conductive relation with the ferrule; and
d) a feedthrough capacitor disposed on or adjacent to the insulator device side,
e) wherein at least a first edge of the feedthrough capacitor extends outwardly beyond a first outermost edge of the ferrule, and
f) wherein at least a second edge of the feedthrough capacitor does not extend outwardly beyond a second outermost edge of the ferrule.

29. A filter feedthrough configured to be installed in an opening of a housing of an active implantable medical device (AIMD), the filter feedthrough comprising:
a) an electrically conductive ferrule comprising a ferrule sidewall defining a ferrule opening extending to a ferrule body fluid side opposite a ferrule device side;
b) an insulator hermetically sealing the ferrule opening by at least one of a first gold braze, a ceramic seal, a glass seal, and a glass-ceramic, the insulator extending to an insulator body fluid side and an insulator device side, wherein, when the ferrule hermetically sealed to the insulator is attached to an opening in a housing of an AIMD, the ferrule and insulator body fluid sides and the ferrule and insulator device sides reside outside and inside the AIMD, respectively;
c) at least one conductive pathway hermetically sealed to and disposed through the insulator between the insulator body fluid and device sides, the at least one conductive pathway being in an electrically non-conductive relation with the ferrule; and
d) a feedthrough capacitor disposed on or adjacent to the ferrule and insulator device sides, the feedthrough capacitor comprising:
i) at least one active electrode plate disposed parallel and spaced from at least one ground electrode plate, wherein the at least one active and ground electrode plates are disposed within a capacitor dielectric;
ii) a capacitor active metallization electrically connected to the at least one active electrode plate and in an electrically non-conductive relation with the at least one ground electrode plate; and
iii) a capacitor ground metallization electrically connected to the at least one ground electrode plate and in an electrically non-conductive relation with the at least one active electrode plate,
e) wherein the capacitor active metallization is electrically connected to the at least one conductive pathway, and
f) wherein the capacitor ground metallization is electrically connected to the ferrule, and
g) wherein at least a first edge of the feedthrough capacitor extends outwardly beyond a first outermost edge of the ferrule, and
h) wherein an imaginary lane aligned with at least a second edge of the feedthrough capacitor and projected toward the ferrule is either aligned with or set back from a second outermost edge of the ferrule, and
i) wherein the ferrule has a rectangular shape with the first and second outermost edges forming at least part of the rectangular shape, and
j) wherein the first outermost edge of the ferrule is perpendicularly disposed in relation to the second outermost edge.

* * * * *

UNITED STATES PATENT AND TRADEMARK OFFICE
CERTIFICATE OF CORRECTION

PATENT NO. : 10,912,945 B2
APPLICATION NO. : 16/360372
DATED : February 9, 2021
INVENTOR(S) : Robert A. Stevenson, Christine A. Frysz and Jason Woods It is certified that error appears in the above-identified patent and that said Letters Patent is hereby corrected as shown below:

In the Claims

Column 41, Line 19 (Claim 29, Column 41, Line 18) delete "lane" and insert --plane--

Signed and Sealed this
Fourteenth Day of March, 2023

Katherine Kelly Vidal
*Director of the United States Patent and Trademark Office*